US011891591B2

(12) United States Patent
Borch et al.

(10) Patent No.: US 11,891,591 B2
(45) **Date of Patent: *Feb. 6, 2024**

(54) LIPASE VARIANTS AND COMPOSITIONS COMPRISING SURFACTANT AND LIPASE VARIANT

(71) Applicant: NOVOZYMES A/S, Bagsvaerd (DK)

(72) Inventors: Kim Borch, Birkerød (DK); Carsten Hørslev Hansen, Vaerloese (DK); Jesper Vind, Vaerloese (DK); Marco Malten, Copenhagen NV (DK); Svend Gunnar Kaasgaard, Skovlunde (DK)

(73) Assignee: NOVOZYMES A/S, Bagsvaerd (DK)

( * ) Notice: Subject to any disclaimer, the term of this patent is extended or adjusted under 35 U.S.C. 154(b) by 9 days.

This patent is subject to a terminal disclaimer.

(21) Appl. No.: 17/518,019

(22) Filed: Nov. 3, 2021

(65) Prior Publication Data

US 2022/0049193 A1 Feb. 17, 2022

Related U.S. Application Data

(62) Division of application No. 16/311,085, filed as application No. PCT/EP2017/065705 on Jun. 26, 2017, now Pat. No. 11,203,732.

(30) Foreign Application Priority Data

Jun. 30, 2016 (EP) .................................... 16177097

(51) Int. Cl.

| | |
|---|---|
| ***C11D 3/386*** | (2006.01) |
| ***C11D 1/14*** | (2006.01) |
| ***C11D 1/22*** | (2006.01) |
| ***C11D 1/83*** | (2006.01) |
| ***C11D 3/33*** | (2006.01) |
| ***C11D 3/50*** | (2006.01) |
| ***C11D 11/00*** | (2006.01) |
| ***C12N 9/20*** | (2006.01) |
| ***C11D 1/72*** | (2006.01) |

(52) U.S. Cl.

CPC ............ *C11D 3/38627* (2013.01); *C11D 1/14* (2013.01); *C11D 1/22* (2013.01); *C11D 1/83* (2013.01); *C11D 3/33* (2013.01); *C11D 3/38609* (2013.01); *C11D 3/38618* (2013.01); *C11D 3/50* (2013.01); *C11D 11/0017* (2013.01); *C12N 9/20* (2013.01); *C11D 1/72* (2013.01)

(58) Field of Classification Search

CPC ........ C12N 9/20; C11D 3/38627; C11D 1/83; C11D 11/0017; C11D 3/38609

See application file for complete search history.

(56) References Cited

U.S. PATENT DOCUMENTS

| | | | | |
|---|---|---|---|---|
| 6,624,129 | B1 | 9/2003 | Borch et al. | |
| 10,669,511 | B2 * | 6/2020 | Borch ...................... | C12N 9/20 |
| 2012/0045817 | A1 | 2/2012 | Estell et al. | |
| 2015/0132831 | A1 | 5/2015 | Olinski et al. | |

FOREIGN PATENT DOCUMENTS

| | | | |
|---|---|---|---|
| CN | 103923895 | A | 7/2014 |
| CN | 104302753 | A | 1/2015 |
| EP | 0746618 | B1 | 12/1996 |
| WO | 92/05249 | A1 | 4/1992 |
| WO | 94/25577 | A1 | 10/1994 |
| WO | 97/04079 | A1 | 2/1997 |
| WO | 99/42566 | A1 | 8/1999 |
| WO | 2000/60063 | A1 | 10/2000 |
| WO | 2014186464 | A1 | 11/2014 |
| WO | 2015/010009 | A2 | 1/2015 |
| WO | 2016/102356 | A1 | 6/2016 |

* cited by examiner

*Primary Examiner* — Iqbal H Chowdhury
(74) *Attorney, Agent, or Firm* — Yoshimi D. Barron

(57) ABSTRACT

The present invention relates to lipase variants and compositions comprising (i) at least one surfactant and (ii) at least one lipase variant of the invention. Furthermore, the present invention relates to methods of using the compositions.

13 Claims, No Drawings

Specification includes a Sequence Listing.

SEQUENCE LISTING

```
<160> NUMBER OF SEQ ID NOS: 6

<210> SEQ ID NO 1
<211> LENGTH: 269
<212> TYPE: PRT
<213> ORGANISM: Humicola lanuginosa

<400> SEQUENCE: 1

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140
```

His Ser Leu Gly Gly Ala Leu Ala Thr Val Ala Gly Ala Asp Leu Arg
145 150 155 160

Gly Asn Gly Tyr Asp Ile Asp Val Phe Ser Tyr Gly Ala Pro Arg Val
165 170 175

Gly Asn Arg Ala Phe Ala Glu Phe Leu Thr Val Gln Thr Gly Gly Thr
180 185 190

Leu Tyr Arg Ile Thr His Thr Asn Asp Ile Val Pro Arg Leu Pro Pro
195 200 205

Arg Glu Phe Gly Tyr Ser His Ser Ser Pro Glu Tyr Trp Ile Lys Ser
210 215 220

Gly Thr Leu Val Pro Val Thr Arg Asn Asp Ile Val Lys Ile Glu Gly
225 230 235 240

Ile Asp Ala Thr Gly Gly Asn Asn Gln Pro Asn Ile Pro Asp Ile Pro
245 250 255

Ala His Leu Trp Tyr Phe Gly Leu Ile Gly Thr Cys Leu
260 265

<210> SEQ ID NO 2
<211> LENGTH: 485
<212> TYPE: PRT
<213> ORGANISM: Artificial sequence
<220> FEATURE:
<223> OTHER INFORMATION: Synthetic construct

<400> SEQUENCE: 2

His His Asp Gly Thr Asn Gly Thr Ile Met Gln Tyr Phe Glu Trp Asn
1 5 10 15

Val Pro Asn Asp Gly Gln His Trp Asn Arg Leu His Asn Asn Ala Gln
20 25 30

Asn Leu Lys Asn Ala Gly Ile Thr Ala Ile Trp Ile Pro Pro Ala Trp
35 40 45

Lys Gly Thr Ser Gln Asn Asp Val Gly Tyr Gly Ala Tyr Asp Leu Tyr
50 55 60

Asp Leu Gly Glu Phe Asn Gln Lys Gly Thr Val Arg Thr Lys Tyr Gly
65 70 75 80

Thr Lys Ala Glu Leu Glu Arg Ala Ile Arg Ser Leu Lys Ala Asn Gly
85 90 95

Ile Gln Val Tyr Gly Asp Val Val Met Asn His Lys Gly Gly Ala Asp
100 105 110

Phe Thr Glu Arg Val Gln Ala Val Glu Val Asn Pro Gln Asn Arg Asn
115 120 125

Gln Glu Val Ser Gly Thr Tyr Gln Ile Glu Ala Trp Thr Gly Phe Asn
130 135 140

Phe Pro Gly Arg Gly Asn Gln His Ser Ser Phe Lys Trp Arg Trp Tyr
145 150 155 160

His Phe Asp Gly Thr Asp Trp Asp Gln Ser Arg Gln Leu Ala Asn Arg
165 170 175

Ile Tyr Lys Phe Arg Gly Asp Gly Lys Ala Trp Asp Trp Glu Val Asp
180 185 190

Thr Glu Asn Gly Asn Tyr Asp Tyr Leu Met Tyr Ala Asp Val Asp Met
195 200 205

Asp His Pro Glu Val Ile Asn Glu Leu Asn Arg Trp Gly Val Trp Tyr
210 215 220

Ala Asn Thr Leu Asn Leu Asp Gly Phe Arg Leu Asp Ala Val Lys His
225 230 235 240

Ile Lys Phe Ser Phe Met Arg Asp Trp Leu Gly His Val Arg Gly Gln
245 250 255

Thr Gly Lys Asn Leu Phe Ala Val Ala Glu Tyr Trp Lys Asn Asp Leu
260 265 270

Gly Ala Leu Glu Asn Tyr Leu Ser Lys Thr Asn Trp Thr Met Ser Ala
275 280 285

Phe Asp Val Pro Leu His Tyr Asn Leu Tyr Gln Ala Ser Asn Ser Ser
290 295 300

Gly Asn Tyr Asp Met Arg Asn Leu Leu Asn Gly Thr Leu Val Gln Arg
305 310 315 320

His Pro Ser His Ala Val Thr Phe Val Asp Asn His Asp Thr Gln Pro
325 330 335

Gly Glu Ala Leu Glu Ser Phe Val Gln Gly Trp Phe Lys Pro Leu Ala
340 345 350

Tyr Ala Thr Ile Leu Thr Arg Glu Gln Gly Tyr Pro Gln Val Phe Tyr
355 360 365

Gly Asp Tyr Tyr Gly Ile Pro Ser Asp Gly Val Pro Ser Tyr Arg Gln
370 375 380

Gln Ile Asp Pro Leu Leu Lys Ala Arg Gln Gln Tyr Ala Tyr Gly Thr
385 390 395 400

Gln His Asp Tyr Leu Asp Asn Gln Asp Val Ile Gly Trp Thr Arg Glu
405 410 415

Gly Asp Ser Ala His Ala Gly Ser Gly Leu Ala Thr Val Met Ser Asp
420 425 430

Gly Pro Gly Gly Ser Lys Thr Met Tyr Val Gly Thr Ala His Ala Gly
435 440 445

Gln Val Phe Lys Asp Ile Thr Gly Asn Arg Thr Asp Thr Val Thr Ile
450 455 460

Asn Ser Ala Gly Asn Gly Thr Phe Pro Cys Asn Gly Gly Ser Val Ser
465 470 475 480

Ile Trp Val Lys Gln
485

<210> SEQ ID NO 3
<211> LENGTH: 269
<212> TYPE: PRT
<213> ORGANISM: Bacillus lentus

<400> SEQUENCE: 3

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Ser Gly Ser Val Ser Ser Ile Ala Gln Gly Leu Glu Trp Ala
100 105 110

Gly Asn Asn Gly Met His Val Ala Asn Leu Ser Leu Gly Ser Pro Ser

```
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 4
<211> LENGTH: 300
<212> TYPE: PRT
<213> ORGANISM: B. amyloliquefacience

<400> SEQUENCE: 4

Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45

Tyr Asn Leu Pro Gly Thr Leu Val Ser Ser Thr Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
        195                 200                 205

Asn Phe Lys Asn Tyr Lys Asn Leu Pro Asn Thr Asp Ala Gly Asp Tyr
    210                 215                 220
```

```
Gly Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
                245                 250                 255

Ala Leu Thr Val Tyr Leu Thr Pro Ser Ser Thr Phe Lys Asp Ala Lys
            260                 265                 270

Ala Ala Leu Ile Gln Ser Ala Arg Asp Leu Tyr Gly Ser Gln Asp Ala
        275                 280                 285

Ala Ser Val Glu Ala Ala Trp Asn Ala Val Gly Leu
    290                 295                 300


<210> SEQ ID NO 5
<211> LENGTH: 300
<212> TYPE: PRT
<213> ORGANISM: B. subtilis

<400> SEQUENCE: 5

Ala Ala Ala Thr Gly Ser Gly Thr Thr Leu Lys Gly Ala Thr Val Pro
1               5                   10                  15

Leu Asn Ile Ser Tyr Glu Gly Gly Lys Tyr Val Leu Arg Asp Leu Ser
            20                  25                  30

Lys Pro Thr Gly Thr Gln Ile Ile Thr Tyr Asp Leu Gln Asn Arg Gln
        35                  40                  45

Ser Arg Leu Pro Gly Thr Leu Val Ser Ser Thr Thr Lys Thr Phe Thr
    50                  55                  60

Ser Ser Ser Gln Arg Ala Ala Val Asp Ala His Tyr Asn Leu Gly Lys
65                  70                  75                  80

Val Tyr Asp Tyr Phe Tyr Ser Asn Phe Lys Arg Asn Ser Tyr Asp Asn
                85                  90                  95

Lys Gly Ser Lys Ile Val Ser Ser Val His Tyr Gly Thr Gln Tyr Asn
            100                 105                 110

Asn Ala Ala Trp Thr Gly Asp Gln Met Ile Tyr Gly Asp Gly Asp Gly
        115                 120                 125

Ser Phe Phe Ser Pro Leu Ser Gly Ser Leu Asp Val Thr Ala His Glu
    130                 135                 140

Met Thr His Gly Val Thr Gln Glu Thr Ala Asn Leu Ile Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Asn Gln Pro Asp
        195                 200                 205

Asn Tyr Ala Asn Tyr Arg Asn Leu Pro Asn Thr Asp Glu Gly Asp Tyr
    210                 215                 220

Gly Gly Val His Thr Asn Ser Gly Ile Pro Asn Lys Ala Ala Tyr Asn
225                 230                 235                 240

Thr Ile Thr Lys Leu Gly Val Ser Lys Ser Gln Gln Ile Tyr Tyr Arg
                245                 250                 255

Ala Leu Thr Thr Tyr Leu Thr Pro Ser Ser Thr Phe Lys Asp Ala Lys
            260                 265                 270

Ala Ala Leu Ile Gln Ser Ala Arg Asp Leu Tyr Gly Ser Thr Asp Ala
        275                 280                 285

Ala Lys Val Glu Ala Ala Trp Asn Ala Val Gly Leu
    290                 295                 300
```

<210> SEQ ID NO 6
<211> LENGTH: 311
<212> TYPE: PRT
<213> ORGANISM: Bacillus species

<400> SEQUENCE: 6

```
Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Ser Gly Ile Lys Val Ala
            20                  25                  30

Val Leu Asp Thr Gly Val Tyr Thr Ser His Leu Asp Leu Ala Gly Ser
        35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ala Ile Arg His Val Ala Asp Glu Ala
        115                 120                 125

Ser Arg Thr Gly Ser Lys Val Val Ile Asn Met Ser Leu Gly Ser Ser
    130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Ser Gly Ser Gly Ser Asn
                165                 170                 175

Thr Ile Gly Phe Pro Gly Gly Leu Val Asn Ala Val Ala Val Ala Ala
            180                 185                 190

Leu Glu Asn Val Gln Gln Asn Gly Thr Tyr Arg Val Ala Asp Phe Ser
        195                 200                 205

Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Thr Gly Asp Asp Tyr Ala Ser Gly
    290                 295                 300

Phe Gly Tyr Pro Arg Val Lys
305                 310
```

LIPASE VARIANTS AND COMPOSITIONS COMPRISING SURFACTANT AND LIPASE VARIANT

CROSS-REFERENCE TO RELATED APPLICATIONS

This application is a divisional of U.S. application Ser. No. 16/311,085 filed on Dec. 18, 2018 (now pending) which is an 35 U.S.C. 371 national application of international application no. PCT/EP2017/065705 filed Jun. 26, 2017, which claims priority or the benefit under 35 U.S.C. 119 of European application no. 16177097.9 filed Jun. 30, 2016, the contents of which are fully incorporated herein by reference.

REFERENCE TO A SEQUENCE LISTING

This application comprises a Sequence Listing in computer readable form, which is incorporated herein by reference.

BACKGROUND OF THE INVENTION

Field of the Invention

The present invention relates to lipase variants and compositions comprising lipase variants of the invention and one or more surfactants, preferably an anionic surfactant, wherein the variants comprise modifications relative to the parent lipase, and optionally, exhibit altered properties, such as activity in the wash process, wash performance, detergent stability and/or storage stability as compared to the parent lipase. The compositions of the invention are suitable as e.g. cleaning or detergent compositions, such as laundry detergent compositions and including adjunct compositions used in combination with such detergent compositions. The compositions may be in any form, such as liquid, gel, or powder form.

Description of the Related Art

Enzymes have been used within the detergent industry as part of washing formulations for many decades. Lipases are important biocatalysts which have shown to be useful for various applications and a large number of different lipases have been identified and many commercialized.

Lipases have been employed in compositions for the removal of lipid stains by hydrolyzing triglycerides to generate fatty acids. Current cleaning and/or fabric care compositions comprise many active ingredients which are interfering with the ability of lipases to remove lipid stains. Thus, the need exists for lipases that can function in the harsh environment of compositions used for cleaning. It is the object of the present application to provide lipases that has advantageous characteristics, such as improved performance when applied in cleaning compositions.

Detergent compositions have been described, but there is a continued need for improved detergent compositions, wherein the enzymes maintain the activity and stability within the detergent compositions in the presence of the detergent component, such as a surfactant in high concentrations. Also there is a need for improved detergent compositions wherein the combined action of the enzymes and detergent components results in an improved performance. Thus, it is an objective of the present invention to provide such enzymes and compositions.

SUMMARY OF THE INVENTION

The present invention relates to lipase variants and compositions comprising one or more surfactants and a lipase variant of the invention.

The inventors have surprising found lipase variants having improved lipase activity in the presence of anionic surfactants, in particular alcohol ether sulfate (AEOS) or linear alkylbenzene sulfonate (LAS), respectively, compared to the parent lipase shown as SEQ ID NO: 1 (LIPOLASE™) The inventors also surprisingly found lipase variants having increased lipase activity in the presence of linear alkylbenzene sulfonate (LAS) and alcohol ethoxylate (AEO) and optionally with a chelating agent or low water hardness, typically below 8° dH.

Therefore, in the first aspect the present invention relates a lipase variant of a parent lipase, wherein said variant (a) comprises a modification in at least one position corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1;

(b) has a sequence identity of at least 75% but less than 100% to SEQ ID NO: 1;

(c) has lipase activity.

A lipase variant of the invention has increased relative activity (i.e., above 1.00) compared to the parent lipase, in particular the lipase shown as SEQ ID NO: 1 (See Example 4).

The relative activity is determined as described in Example 4 and is in a preferred embodiment above 1.10, preferably above 1.50, preferably above 2.00, preferably above 2.50, preferably above 3.00, more preferably above 3.50, in particular above 4.00, in particular above 5.00, in particular above 6.00, in particular above 7.00, in particular above 8.00, in particular above 9.00, in particular above 10.00, in particular above 11.00, in particular above 12.00, in particular above 13.00, in particular above 14.00, in particular above 15.00, in particular above 16.00, in particular above 17.00, in particular above 18.00, in particular above 19.00, in particular above 20.00, in particular above 21.00, in particular above 22.00, in particular above 23.00, in particular above 24.00, in particular above 25.00, such as in the range between 1.10 and 25, such as between 1.50 and 20.00, such as between 2.00 and 15.00, such as between 3.00 and 10.00.

In an embodiment the relative activity is determined in the presence of one or more anionic surfactants. In an embodiment the relative activity is determined in the presence of one or more nonionic surfactants. In an embodiment the relative activity is determined in the presence of one or more anionic surfactants and one or more nonionic surfactants. In an embodiment a chelating agent may further be present.

In an embodiment the relative activity is determined in the presence of LAS.

In an embodiment the relative activity is determined in the presence of AEOS.

In an embodiment the relative activity is determined in the presence of LAS and AEO.

In an embodiment the relative activity is determined in the presence of LAS, AEO and a cleating agent, such as EDTA.

In an embodiment the relative activity is determined in surfactant solution A in Example 4.

In an embodiment the relative activity is determined in surfactant solution B in Example 4.

In an embodiment the relative activity is determined in surfactant solution C in Example 4.

In an embodiment the relative activity is determined in surfactant solution D in Example 4.

In an embodiment the relative activity is determined in surfactant solution E in Example 4.

In an embodiment the relative activity is determined in surfactant solution F in Example 4.

In an embodiment the relative activity is determined in surfactant solution G in Example 4.

The present invention also relates to a composition comprising (i) a surfactant and (ii) a lipase variant of a parent lipase, wherein said variant.

(a) comprises a modification in at least one position corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1;

(b) has a sequence identity of at least 75% but less than 100% to SEQ ID NO: 1;

(c) has lipase activity; and (d) has an improved activity as compared to the parent lipase.

The present invention also relates also to use of the composition according to any one of the disclosed embodiments in laundry, or industrial cleaning.

The present invention relates also to a method of laundering, comprising laundering a fabric with a detergent composition according to any one of the disclosed embodiments, preferably at a temperature of 50° C. or less, or more preferably at a temperature of 40° C. or less, or more preferably at a temperature of 30° C. or less, or even more preferably at a temperature of 20° C. or less.

Overview of Sequences Listing

SEQ ID NO: 1 is the amino acid sequence of a lipase (Lipolase™)

SEQ ID NO: 2 is the amino acid sequence of a fusion alpha-amylase (LABM)

SEQ ID NO: 3 is the amino acid sequence of a protease (Savinase®)

SEQ ID NO: 4 is the amino acid sequence of a protease (Neutrase™)

SEQ ID NO: 5 is the amino acid sequence of a protease (Metalloprotease)

SEQ ID NO: 6 is the amino acid sequence of a protease (TY145)

Definitions

The term “lipase”, “lipase enzyme”, “lipolytic enzyme”, “lipid esterase”, “lipolytic polypeptide”, and “lipolytic protein” as used herein, refers to an enzyme in class EC 3.1,1 as defined by Enzyme Nomenclature. It may have lipase activity (triacylglycerol lipase, EC 3.1.1.3), cutinase activity (EC 3.1.1.74), sterol esterase activity (EC 3.1.1.13) and/or wax-ester hydrolase activity (EC 3.1.1.50). For purposes of the present invention, lipase activity is activity of the refolded lipase and determined according to the procedure described in the Examples section (Lipase assay: Hydrolytic activity on fatty acids pNP esters). In one aspect, the polypeptides of the present invention have at least 20%, e.g., at least 25%, at least 30%, at least 35%, at least 40%, at least 45%, at least 50%, at least 55%, at least 60%, at least 65%, at least 70%, at least 80%, at least 85%, at least 90%, at least 95%, or at least 100% of the lipase activity of the polypeptide of SEQ ID NO: 1.

The term “parent” or “parent lipase” as used herein, refers to a lipase to which a substitution is made to produce the lipase variants of the present invention. The parent may be a naturally occurring (wild-type) polypeptide or a variant or fragment thereof.

The term “corresponding to” as used herein, refers to a way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 1, or any other sequence listed herein, has been described elsewhere herein. Alternative alignment methods may be used, and are well-known for the skilled person in the art.

The term “sequence identity” as used herein, refers to the relatedness between two amino acid sequences or between two nucleotide sequences is described by the parameter “sequence identity”.

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used may be gap open penalty of 10, gap extension penalty of 0.5, and the EBLOSUM62 (EMBOSS version of BLOSUM62) substitution matrix. The output of Needle labeled “longest identity” (obtained using the –nobrief option) is used as the percent identity and is calculated as follows:

(Identical Residues×100)/(Length of Alignment−Total Number of Gaps in Alignment)

Alternatively, the parameters used may be gap open penalty of 10, gap extension penalty of 0.5, and the EDNAFULL (EMBOSS version of NCBI NUC4.4) substitution matrix. The output of Needle labeled “longest identity” (obtained using the –nobrief option) is used as the percent identity and is calculated as follows:

(Identical Deoxyribonucleotides×100)/(Length of Alignment−Total Number of Gaps in Alignment)

The term “surfactant” as used herein, refers to any conventional understanding of a surfactant within the art, which may be anionic and/or non-ionic and/or semi-polar and/or zwitterionic and/or cationic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant of the present invention may preferably be present in concentrations such that it exists mainly in micellar form, i.e. at concentrations above the critical micelle concentration in the main wash. The term “critical micelle concentration” as used herein, refers to a micelle concentration of a surfactant or blend of surfactants and is determined by a number of factors such as pH, temperature, ionic strength etc. To determine whether a surfactant or blend of surfactants is present in the main wash solution in concentrations at or above the critical micelle concentration a number of different methods may be used.

The term "micelle" as used herein, refers to a spontaneously and reversibly formation of water-soluble aggregates of amphiphilic molecules, such as surfactants, in an aqueous solution.

The term "improved property" when referring to a lipase variant herein, refers to a characteristic associated with a lipase variant that is improved compared to the parent lipase, e.g. a parent lipase having the sequence of SEQ ID NO: 1, or compared to a lipase having the identical amino acid sequence of said variant but not having the alteration at one or more of said specified positions. Such improved properties include, but are not limited to, wash performance, lipase activity, malodor reduction, thermal activity profile, thermostability, pH activity profile, pH stability, substrate specificity, improved surface properties, product specificity, increased stability including stability during the main wash process, improved stability under storage conditions, and chemical stability.

The term "improved lipase activity" is defined herein as an enzyme's ability to hydrolyze fatty acyl esters including triglycerides, diglycerides, monoglycerides. This will facilitate removal of lipid or lipid-containing stains present on the object to be cleaned by conversion of the hydrophobic triglycerides to more hydrophilic and water soluble reaction products catalyzed by the lipase. The wash performance may be quantified by calculating the so-called G/Int value defined in the description of AMSA in the Methods section below. The term "wash performance" includes cleaning in general e.g. hard surface cleaning, but also wash performance on textiles such as laundry, and also industrial and institutional cleaning.

The term "cleaning" covers all types of cleaning including laundry washing, hard surface cleaning, industrial cleaning, and institutional cleaning.

The term "improved wash performance" as used herein, refers to an enzyme's ability to facilitate removal of lipid or lipid-containing stains present on the object to be cleaned.

The term "stability" includes storage stability and stability during use, e.g. during a wash process and reflects the stability of the lipase variant according to the invention as a function of time e.g. how much activity is retained when the lipase variant is kept in solution in particular in a detergent solution. The stability is influenced by many factors e.g. pH, temperature, detergent composition e.g. amount of builder, surfactants etc.

The term "improved stability" or "increased stability" is defined herein as a variant being a lipase variant displaying an increased stability in solutions, relative to the stability of the parent lipase, relative to a lipase having the identical amino acid sequence of said variant but not having the alterations at one or more of said specified positions or relative to SEQ ID NO: 1. The terms "improved stability" and "increased stability" includes "improved chemical stability", "detergent stability" or "improved detergent stability". Enzyme stability may be measured as described in the Examples.

The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants being more able to catalyze a reaction in the presence of such chemicals. In a particular aspect of the invention the improved chemical stability is an improved stability in a detergent, in particular in a liquid detergent. The term "detergent stability" or "improved detergent stability" is in particular an improved stability of the enzyme activity when a enzyme variant is mixed into a liquid detergent formulation, especially into a liquid detergent formulation according to table 1 and then stored at temperatures between 15 and 50° C., e. g. 20° C., 30° C. or 40° C. for at least one week.

The term "improved thermal activity" means a variant displaying an altered temperature-dependent activity profile at a specific temperature relative to the temperature-dependent activity profile of the parent or relative to a lipase of SEQ ID NO: 1. The thermal activity value provides a measure of the variant's efficiency in enhancing catalysis of a hydrolysis reaction over a range of temperatures.

The term "improved wash performance" is defined herein as a variant displaying an improved wash performance relative to the wash performance of the parent enzyme, relative to a polypeptide of SEQ ID NO: 1, or relative to an enzyme having the identical amino acid sequence of said variant but not having the alterations at one or more of said specified positions e.g. by increased stain removal. The term "wash performance" includes wash performance in laundry. The wash performance may be quantified as described under the definition of "wash performance" herein.

The term "anionic surfactant" as used herein, refers to the non-limiting examples of anionic surfactants including sulfates and sulfonates, in particular, linear alkylbenzene sulfonates (LAS), isomers of LAS, branched alkylbenzene sulfonates (BABS), phenylalkane sulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ether sulfates (AES or AEOS or FES, also known as alcohol ethoxy sulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

The term "a mix of two or more surfactants" as used herein, refers to the combination of at least two surfactants which may be of the same group of surfactants, such as a combination of one anionic surfactant and second anionic surfactant, or it may be a combination of surfactants of different groups, such as one anionic surfactant and one non-ionic surfactant.

The term "non-ionic surfactant" as used herein, refers to the non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

The term "fabric" or "garment" as used herein, refers to any textile material. Thus, it is intended that the term encompass garments, as well as fabrics, yarns, fibers, non-woven materials, natural materials, synthetic materials, and any other textile material.

The term "textile" as used herein, refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "non-fabric detergent compositions" include non-textile surface detergent compositions, including but not limited to compositions for hard surface cleaning, such as oral detergent compositions, denture detergent compositions, and personal cleansing compositions.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a variant refers to the quantity of variant described hereinbefore that achieves a desired level of enzymatic activity, e.g., in a defined detergent composition.

The term "water hardness" or "degree of hardness" or "dH" or "° dH" as used herein refers to German degrees of hardness. One degree is defined as 10 milligrams of calcium oxide per litre of water.

The term "resulting water hardness" as used herein, refers to the water hardness measured in the wash water during a wash cycle. A wash cycle may be a wash cycle of a laundering process. The wash cycle refers to the part of a process, such as a laundering process, where the water is supplemented with the composition, such as detergent composition.

The term "relevant washing conditions" is used herein to indicate the conditions, particularly washing temperature, time, washing mechanics, detergent concentration, type of detergent and water hardness, actually used in households in a detergent market segment.

The term "stain removing enzyme" as used herein, describes an enzyme that aids the removal of a stain or soil from a fabric or a hard surface. Stain removing enzymes act on specific substrates, e.g., protease on protein, amylase on starch, lipase and cutinase on lipids (such as acyl esters in fats and oils from animal or plant materials), pectinase on pectin and hemicellulases on hemicellulose. Stains are often depositions of complex mixtures of different components which either results in a local discolouration of the material by itself or which leaves a sticky surface on the object which may attract soils dissolved in the washing liquor thereby resulting in discolouration of the stained area. When an enzyme acts on its specific substrate present in a stain the enzyme degrades or partially degrades its substrate thereby aiding the removal of soils and stain components associated with the substrate during the washing process. For example, when a protease acts on a grass stain it degrades the protein components in the grass and allows the green/brown colour to be released during washing.

The term "reduced amount" means in this context that the amount of the component is smaller than the amount which would be used in a reference process under otherwise the same conditions. In a preferred embodiment the amount is reduced by, e.g., at least 5%, such as at least 10%, at least 15%, at least 20% or as otherwise herein described.

The term "low detergent concentration" system includes detergents where less than about 800 ppm of detergent components is present in the wash water. Asian, e.g., Japanese detergents are typically considered low detergent concentration systems.

The term "medium detergent concentration" system includes detergents wherein between about 800 ppm and about 2000 ppm of detergent components is present in the wash water. North American detergents are generally considered to be medium detergent concentration systems.

The term "high detergent concentration" system includes detergents wherein greater than about 2000 ppm of detergent components is present in the wash water. European detergents are generally considered to be high detergent concentration systems.

The term "additional enzymes" as used herein, refers to a second or a further enzyme to be included in the composition. The additional enzyme may be any enzyme of another enzyme class than lipase, but it may also comprise a second/further lipase, i.e. the composition according to the invention comprises more than one lipase, such as two or more lipases.

The terms "alpha-amylase" and "amylase" may be used interchangeably and constitute the same meaning and purpose within the scope of the present invention.

The term "alpha-amylase variant" as used herein, refers to an alpha-amylase having alpha-amylase activity comprising an alteration, i.e., a substitution, insertion, and/or deletion, at one or more (e.g., several) positions as compared to a "parent alpha-amylase". A substitution means a replacement of an amino acid occupying a position with a different amino acid; a deletion means removal of an amino acid occupying a position; and an insertion means adding amino acids e.g. 1 to 10 amino acids, preferably 1 to 3 amino acids adjacent to an amino acid occupying a position. Amino acid substitutions may exchange a native amino acid for another naturally-occurring amino acid, or for a non-naturally-occurring amino acid derivative. The alpha-amylase variants have at least 20%, e.g., at least 40%, at least 50%, at least 60%, at least 70%, at least 80%, at least 90%, at least 95%, or at least 100% of the alpha-amylase activity of the mature parent alpha-amylase from which they have been derived.

The term "alpha-amylase activity" as used herein, refers to the activity of alpha-1,4-glucan-4-glucanohydrolases, E.C. 3.2.1.1, which constitute a group of enzymes, catalyzing hydrolysis of starch and other linear and branched 1,4-glucosidic oligo- and polysaccharides. Thus, the term "alpha-amylase" as used herein, refers to an enzyme that has alpha-amylase activity (Enzyme Class; EC 3.2.1.1) that hydrolyses alpha bonds of large, alpha-linked polysaccharides, such as starch and glycogen, yielding glucose, maltose, and short chained oligosaccharides. For purposes of the present invention, alpha-amylase activity is determined according to the procedure described in the Examples. In one embodiment, the variants of the present invention have at least 20%, e.g., at least 40%, at least 50%, at least 60%, at least 70%, at least 80%, at least 90%, at least 95%, or at least 100% of the alpha-amylase activity of the polypeptide of SEQ ID NOs: 2.

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The term "subtilases" refer to a sub-group of serine protease according to Siezen et al., *Protein Engng.* 4 (1991) 719-737 and Siezen et al. *Protein Science* 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Proteases of the invention are endopeptidases (EC 3.4.21). For purposes of the present invention, protease activity is determined according to the procedure described in Example 1 below. The protease variants described herein have at least 20%, e.g., at least 40%, at least 50%, at least 60%, at least 70%, at least 80%, at least 90%, at least 95%, or at least 100% of the protease activity of the mature polypeptide with SEQ ID NO: 3, 4, 5, or 6.

The term "protease activity" as used herein, refers to the activity of hydrolysis of peptide bonds. For purposes of the present invention, protease activity is determined according to the procedure described in the Examples. In one embodiment, the variants of the present invention have at least 20%, e.g., at least 40%, at least 50%, at least 60%, at least 70%, at least 80%, at least 90%, at least 95%, or at least 100% of the protease activity of the polypeptide of SEQ ID NOs: 3, 4, 5, or 6.

The term "protease variant" as used herein, refers to a protease having protease activity comprising an alteration, i.e., a substitution, insertion, and/or deletion, preferably substitution, at one or more (or one or several) positions compared to its parent which is a protease having the identical amino acid sequence of said variant but not having the alterations at one or more of said specified positions.

The term "modification" is described elsewhere herein. The term is a overall designation of the terms "substitution", "insertion", and "deletion" as described herein.

The term "chelating agents" or "chelators" as used herein, refers to chemicals which form molecules with certain metal ions, inactivating the ions so that they cannot react with other elements thus a binding agent that suppresses chemical activity by forming chelates. Chelation is the formation or presence of two or more separate bindings between a ligand and a single central atom. The ligand may be any organic compound, a silicate or a phosphate. In the present context the term "chelating agents" comprises chelants, chelating agent, chelating agents, complexing agents, or sequestering agents that forms water-soluble complexes with metal ions such as calcium and magnesium. The chelate effect describes the enhanced affinity of chelating ligands for a metal ion compared to the affinity of a collection of similar nonchelating ligands for the same metal. Chelating agents having binding capacity with metal ions, in particular calcium ($Ca^{2+}$) ions, and has been used widely in detergents and compositions in general for wash, such as laundry or dish wash. Chelating agents have however shown themselves to inhibit enzymatic activity. The term chelating agent is used herein interchangeably with "complexing agent" or "chelating agent" or "chelant".

The activity of many lipases are calcium sensitive. The presence of chelating agents may impair the enzyme activity. The effect of chelating agents on lipase activity can be through removal of calcium ions from the lipase having calcium bound at a position important for stability and/or activity. Alternatively, chelating agents can affect lipase activity indirectly, e.g., by affecting the interactions between calcium ions and free fatty acids produced or interaction between calcium and surfactant ions or a combination thereof. The calcium sensitivity of a lipase can be determined by testing the activity of a given lipase in the presence of a strong chelating agent.

Characterizing chelating agents: As mentioned the chelate effect or the chelating effect describes the enhanced affinity of chelating ligands for a metal ion compared to the affinity of a collection of similar nonchelating ligands for the same metal. However, the strength of this chelate effect can be determined by various types of assays or measure methods thereby differentiating or ranking the chelating agents according to their chelating effect (or strength).

In a preferred assay the chelating agents may be characterized by their ability to reduce the concentration of free calcium ions ($Ca^{2+}$) from 2.0 mM to 0.10 mM or less at pH 8.0, e.g. by using a test based on the method described by M. K. Nagarajan et al., JAOCS, Vol. 61, no. 9 (September 1984), pp. 1475-1478. An example of characterization of chelating agents using the Nagarajan et. al. based method is described in Example 1. Preferably, a the chelating agent in context of the invention encompasses chelating agents able to reduce the concentration of free calcium ions from 2.0 mM to 0.1 mM or less at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, preferably below 4 mM, preferably below 3.5 mM, preferably below 3 mM, preferably below 2.5 mM, preferably below 2 mM, preferably below 1.5 mM or preferably below 1 mM, when measured in pH 8.0 at 21° C.

Preferably, the chelating agent encompasses chelating agents able to reduce the concentration of free calcium ions from 2.0 mM to 0.1 mM at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM, when measured in 80 mM potassium chloride and 49 mM EPPS ((4-(2-hydroxyethyl)piperazine-1-propanesulfonic acid)), at pH 8 at 21° C. In a particular preferred embodiment the chelating agent is able to reduce the concentration of free calcium ions from 2.0 mM to 0.1 mM when measured in 80 mM potassium chloride and 49 mM EPPS, at pH 8 and 21° C. and using a calcium ion selective electrode for the determination of the free calcium concentration, as described in Example 1. Thus preferably, the chelating agents encompass chelating agents which are able to reduce the concentration of free calcium ions from 2.0 mM to 0.10 mM at a concentration below 10 mM, preferably below 9.5 mM, preferably below 9.0 mM, preferably below 8.5 mM, preferably below 8.0 mM, preferably below 7.5 mM, preferably below 7.0 mM, preferably below 6.5 mM, preferably below 6.0 mM, preferably below 5.5 mM, preferably, preferably below 5.0 mM, preferably below 4.5 mM, below 4.0 mM, preferably below 3.5 mM, preferably below 3.0 mM, preferably below 2.5 mM, preferably below 2.0 mM, preferably below 1.5 mM or preferably below 1.0 mM when tested at pH 8.0 and 21° C., as described in Example 1.

Examples of typical chelating agents and their ability to reduce the concentration of free calcium ions from 2.0 mM to 0.1 mM at pH 8.0 in 49 mM EPPs buffer and 80 mM potassium chloride are shown below. The concentration of chelating agent required to reduce the concentration of free calcium ions from 2.0 mM to 0.1 mM were determined following the procedure described in Example 1: "Assay for measurement of free calcium":

| | mM | Relative to citrate |
|---|---|---|
| Citrate | 8.36 | 1.00 |
| EGTA | 2.60 | 0.33 |
| EDTA | 1.90 | 0.21 |
| HEDP | 1.60 | 0.20 |
| DTPA | 1.87 | 0.24 |
| DTPMP | 1.17 | 0.15 |
| MGDA | 2.56 | 0.33 |

In a particularly preferred embodiment the chelating agents is able to reduce the concentration of free calcium ions from 2.0 mM to 0.10 mM when measured in 80 mM potassium chloride and 49 mM EPPS at pH 8 and 21° C. at a concentration of 9 mM to 0.5 mM, preferably 9 mM to 1 mM, preferably 8 mM to 1 mM, preferably 7 mM to 1 mM, preferably 6 mM to 1 mM, preferably 5 mM to 1 mM, preferably 4 mM to 1 mM, preferably 3 mM to 1 mM, preferably 2 mM to 1 mM, preferably 9.0 mM to 1.5 mM, preferably 8.0 mM to 1.5 mM, preferably 7.0 mM to 1.5 mM, preferably 6.0 mM to 1.5 mM, preferably 5.0 mM to 1.5 mM, preferably 4.0 mM to 1.5 mM, preferably 3.0 to 1.5 mM, preferably 2.5 mM to 1.0 mM, preferably 2.0 mM to 1.1 mM, preferably 1.85 mM to 1.0 mM.

The reduction in free calcium ion concentration from 2.0 mM $Ca^{2+}$ to 0.10 mM, corresponds to reducing the water hardness from 200 ppm (as $CaCO_3$, in the form of $Ca(HCO_3)_2$ in the presence of acidic $CO_2$) to 10 ppm. The minimum builder level is calculated from the sodium salt of the chelant and on a 100% dry chelant basis.

The chelating effect of the chelating agent can also be measured relative to citrate. The concentration of the citrate able to reduce the amount of free calcium ion concentration from 2.0 mM to 0.10 mM is assigned the value of 1 and the results of the chelating agents are compared to this value. The preferred chelating agent according to the invention is capable of reducing the free calcium concentration from 2.0 mM to 0.10 mM at a concentration below 0.9, such as below 0.8, such as below 0.7, such as below 0.6, such as below 0.5, such as below 0.4, such as below 0.3, such as below 0.2, such as below 0.1 times lower compared to the concentration of citrate, when measured at pH 8.0 and 21° C. The preferred chelating agent according to the invention is capable of reducing the free calcium concentration from 2.0 mM to 0.10 mM at a concentration below 0.9, such as below 0.8, such as below 0.7, such as below 0.6, such as below 0.5, such as below 0.4, such as below 0.3, such as below 0.2, such as below 0.1 times lower compared to the concentration of citrate, when measured in pH 8.0 at 21° C. using a calcium ion selective electrode for the determination of the free calcium concentration when measured in 80 mM potassium chloride and 49 mM EPPS at 21° C. and pH 8.0.

In a particularly preferred embodiment the chelating agent is able to reduce the concentration of free calcium ions from 2.0 mM to 0.10 mM at a chelating agent concentration below 1.0 to 0.1, such as below 0.9 to 0.1, such as below 0.8 to 0.1, such as below 0.7 to 0.1, such as below 0.6 to 0.1, such as below 0.5 to 0.1, such as below 0.4 to 0.1, such as below 0.35 to 0.1, such as below 0.3 to 0.1 times lower compared to the concentration of citrate able to reduce the concentration of free calcium ions from 2.0 mM to 0.10 mM, when measured at pH 8.0 and 21° C. The term "builder" may be classified by the test described by M. K. Nagaraja et al., JAOCS, Vol. 61, no. 9 (September 1984), pp. 1475-1478 to determine the minimum builder level required to lower the water hardness at pH 8 from 2.0 mM (as $CaCO_3$) to 0.10 mM in a solution. The builder may particularly be a chelating agent that forms water-soluble complexes with e.g. calcium and magnesium ions. The term "adjunct composition" as used herein, refers to any composition which is not considered be encompassed in the term "detergent composition". Accordingly, an adjunct composition may be a "pre-treatment composition", i.e. a composition applied to the material to be cleaned before the main wash, a "soaking composition", i.e. a composition used for a pretreatment by soaking before the main wash or a "boosting composition", i.e. a composition used to boost the wash performance of the detergent used in the main wash. The term "adjunct composition" means any liquid, solid or gaseous material selected for the particular type of detergent composition desired and the form of the product (e.g., liquid, granule, powder, bar, paste, spray, tablet, gel, or foam composition), which materials are also preferably compatible with the enzymes used in the composition. In some embodiments, granular compositions are in "compact" form, while in other embodiments, the liquid compositions are in a "concentrated" form.

The term "main wash" as used herein refers to one of the steps of the of the entire wash cycle, which typically consists of the following steps: pretreatment, prewash, main wash, rinse and drying. In some cases a pretreatment or prewashing step is not required. The ancillary composition is mainly used in the pretreatment, prewashing or main washing step. The detergent composition for laundry is normally added in the main washing step. When evaluating wash performance, the evaluation is most often done after washing, rinsing, and drying steps.

Conventions for Designation of Variants

For purposes of the present invention, the polypeptides disclosed in SEQ ID NO: 1, 2, 3, 4, 5, and 6 may be used to determine the corresponding amino acid residue in another polypeptide. The amino acid sequence of another polypeptide is aligned with the polypeptide disclosed in SEQ ID NO: 1, 2, 3, 4, 5, or 6 depending on whether it is a lipase, an alpha-amylase, or a protease, and based on the alignment, the amino acid position number corresponding to any amino acid residue in the polypeptide disclosed in SEQ ID NO: 1, 2, 3, 4, 5, or 6 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another enzyme may be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 1, 2, 3, 4, 5, or 6 such that traditional sequence-based comparison fails to detect their relationship (Lindahl and Elofsson, 2000, *J. Mol. Biol.* 295: 613-615), other pairwise sequence comparison algorithms may be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP super families of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

It is within the knowledge of the skilled person to determine which alignment tool to use when corresponding amino acid positions must be identified. Therefore, it is contemplated that any available alignment tool that the skilled person find suitable may be used in the context of the present invention.

In describing the enzyme variants described herein, the nomenclature described below is adapted for ease of reference. The accepted IUPAC single letter or three letters amino acid abbreviations are employed. Amino acid positions are indicated with H1, G109, etc.

Variants described herein comprises one or more modifications as compared to the parent polypeptide. Accordingly, variants may comprise conservative modifications, in particular, such conservative modifications may be conservative substitutions. Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Asn/Gln, Thr/Ser, Ala/Gly, Ala/Thr, Ser/Asn, Ala/Val, Ser/Gly, Tyr/Phe, Ala/Pro, Lys/Arg, Asp/Asn, Glu/Gln, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Substitutions: For an amino acid substitution, the following nomenclature is used: Original amino acid, position, substituted amino acid. Accordingly, the substitution of glycine at position G109 with alanine is designated as "Gly109Ala" or "G109A". Multiple mutations are separated by addition marks ("+") or by commas (","), e.g., "Gly109Ala+Leu173Pro" or "G109A,L173P", representing substitutions at positions 109 and 173 of glycine (G) with alanine (A) and leucine (L) with proline (P), respectively. If more than one amino acid may be substituted in a given position these are listed or divided by slash, such as /. Thus, if both Ala and Pro according to the invention may be substituted instead of the amino acid occupying at position 109 this is indicated as X109A/P where the X in the present example indicates that different enzymes may be parent e.g. such as an alpha-amylase with SEQ ID NO: 1 or an alpha-amylase having at least 75% identity hereto. Thus, in some cases the variants are represented as 109A/P or X109A/P indicating that the amino acids to be substituted vary depending on the parent enzyme.

Deletions: For an amino acid deletion, the following nomenclature is used: Original amino acid, position, *. Accordingly, the deletion of arginie at position 181 is designated as "Arg181*" or "R181*". Multiple deletions are separated by addition marks ("+") or commas, e.g., "Arg181*+Gly182*" or "R181*+G182*" or "R181*, G182*".

Insertions: The insertion of an additional amino acid residue such as e.g. a lysine after $G\#_1$ may be indicated by: $Gly\#_1$GlyLys or $G\#_1$GK. Alternatively insertion of an additional amino acid residue such as lysine after G109 may be indicated by: *109aL. When more than one amino acid residue is inserted, such as e.g. a Lys, and Ala after 109 this may be indicated as: Gly109GlyLysAla or G109GKA. In such cases, the inserted amino acid residue(s) may also be numbered by the addition of lower case letters to the position number of the amino acid residue preceding the inserted amino acid residue(s), in this example: *109aK *109bA.

Collectively, substitutions, deletions, and insertions may herein termed "modifications". Thus, it is to be understood that any variant described herein comprises modifications, such as substitutions, deletions and/or insertions unless otherwise indicated by context.

Multiple modifications: Variants comprising multiple modifications are separated by addition marks ("+"), slash marks ("/"), or by commas (","), e.g., "Gly109Pro+Lys391Ala" or "G109P, K391A" representing a substitution of glycine at position 109 and lysine at position 391 with proline and alanine, respectively as described above.

Different modifications: Where different modifications can be introduced at a position, the different modifications are separated by a division ("/"), or by a comma (","), e.g., "Gly109Pro,Lys" or "G109P,K" represents a substitution of glycine at position 109 with proline or lysine. Thus, "Gly109Pro,Lys+Lys391Ala" designates the following variants: "Gly109Pro+Lys391Ala", "Gly109Lys+Lys391Ala" or "G109P,K+K391A".

DETAILED DESCRIPTION OF THE INVENTION

The present invention relates to lipase variants and compositions comprising one or more surfactants and one or more lipase variant of the invention.

Lipase Variants of the Invention

In the first aspect the invention relates a lipase variant of a parent lipase, wherein said variant (a) comprises a modification in at least one position corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1;

(b) has a sequence identity of at least 75% but less than 100% to SEQ ID NO: 1;

(c) has lipase activity.

The term "variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS PAGE. The term "modification" is described elsewhere herein. The term is a overall designation of the terms "substitution", "insertion", and "deletion" as described herein.

The term "corresponding to" as used herein, refers to way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 1, or any other sequence listed herein, has been described elsewhere herein. Alternative alignment methods may be used, and are well-known for the skilled person.

The lipase variant described herein has an improved activity as compared to the parent lipase and optionally an improved odor reduction as compared to the parent lipase, in particular SEQ ID NO: 1. In certain embodiments, the lipase variant further has an improved stability. Accordingly, the lipase variant comprises at least one modification in the positions corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1.

In a preferred embodiment the lipase variant of the invention comprises substitutions E1C+N233C and one or more additional substitutions.

The lipase variant of the composition according to the invention has at least 75%, such as at least 75%, such as at least 80%, such as at least 85%, such as at least 90%, such as at least 95%, such as at least 96%, such as at least 97%, such as at least 98%, such as at least 99%, but less than 100% sequence identity to the amino acid sequence of SEQ ID NO: 1. Accordingly, in one embodiment, the lipase variant has at least 75%, such as at least 80%, such as at least 85%, such as at least 90%, such as at least 95%, such as at least 96%, such as at least 97%, such as at least 98%, such as at least 99% but less than 100% sequence identity to the amino acid sequence of SEQ ID NO: 1.

In one embodiment, the lipase variant comprises a modification in two positions selected from the positions corresponding to E1, V2, N33, F51, E56, L69, K98, V176, H198, E210, Y220, and L227 of SEQ ID NO: 1. Thus, in a particular embodiment, the lipase variant comprises a modification in two positions selected from the group consisting of; E1+V2, E1+N33, E1+F51, E1+E56, E1+L69, E1+K98, E1+V176, E1+H198, E1+E210, E1+Y220, E1+L227, V2+N33, V2+F51, V2+E56, V2+L69, V2+K98, V2+V176, V2+H198, V2+E210, V2+Y220, V2+L227, N33+F51, N33+E56, N33+L69, N33+K98, N33+V176, N33+H198, N33+E210, N33+Y220, N33+L227, F51+E56, F51+L69, F51+K98, F51+V176, F51+H198, F51+E210, F51+Y220, F51+L227, E56+L69, E56+K98, E56+V176, E56+H198, E56+E210, E56+Y220, E56+L227, L69+K98, L69+V176, L69+H198, L69+E210, L69+Y220, L69+L227, K98+V176, K98+H198, K98+E210, K98+Y220, K98+L227, V176+H198, V176+E210, V176+Y220, V176+L227, H198+E210, H198+Y220, H198+L227, E210+Y220, E210+L227, and Y220+L227, wherein numbering is according to SEQ ID NO: 1.

In a particular embodiment, the lipase variant comprises a modification in two positions selected from the positions corresponding to positions E1, V2, D27, N33, G38, F51, E56, L69, D96, K98, D111, G163, V176, H198, E210, Y220, L227, T231, N233, N233, D254, and P256, wherein numbering is according to SEQ ID NO: 1. Thus, in a particular embodiment, the lipase variant comprises a modification in two positions selected from the group consisting of: E1+V2, E1+D27, E1+N33, E1+G38, E1+F51, E1+E56, E1+L69, E1+D96, E1+K98, E1+D111, E1+G163, E1+V176, E1+H198, E1+E210, E1+Y220, E1+L227, E1+T231, E1+N233, E1+D254, E1+P256, V2+D27, V2+N33, V2+G38, V2+F51, V2+E56, V2+L69, V2+D96, V2+K98, V2+D111, V2+G163, V2+V176, V2+H198, V2+E210, V2+Y220, V2+L227, V2+T231, V2+N233, V2+D254, V2+P256, D27+N33, D27+G38, D27+F51, D27+E56, D27+L69, D27+D96, D27+K98, D27+D111, D27+G163, D27+V176, D27+H198, D27+E210, D27+Y220, D27+L227, D27+T231, D27+N233, D27+D254, D27+P256, N33+G38, N33+F51, N33+E56, N33+L69, N33+D96, N33+K98, N33+D111, N33+G163, N33+V176, N33+H198, N33+E210, N33+Y220, N33+L227, N33+T231, N33+N233, N33+D254, N33+P256, G38+F51, G38+E56, G38+L69, G38+D96, G38+K98, G38+D111, G38+G163, G38+V176, G38+H198, G38+E210, G38+Y220, G38+L227, G38+T231, G38+N233, G38+D254, G38+P256, F51+E56, F51+L69, F51+D96, F51+K98, F51+D111, F51+G163, F51+V176, F51+H198, F51+E210, F51+Y220, F51+L227, F51+T231, F51+N233, F51+D254, F51+P256, E56+L69, E56+D96, E56+K98, E56+D111, E56+G163, E56+V176, E56+H198, E56+E210, E56+Y220, E56+L227, E56+T231, E56+N233, E56+D254, E56+P256, L69+D96, L69+K98, L69+D111, L69+G163, L69+V176, L69+H198, L69+E210, L69+Y220, L69+L227, L69+T231, L69+N233, L69+D254, L69+P256, D96+K98, D96+D111, D96+G163, D96+V176, D96+H198, D96+E210, D96+Y220, D96+L227, D96+T231, D96+N233, D96+D254, D96+P256, K98+D111, K98+G163, K98+V176, K98+H198, K98+E210, K98+Y220, K98+L227, K98+T231, K98+N233, K98+D254, K98+P256, D111+G163, D111+V176, D111+H198, D111+E210, D111+Y220, D111+L227, D111+T231, D111+N233, D111+D254, D111+P256 G163+V176, G163+H198, G163+E210, G163+Y220, G163+L227, G163+T231, G163+N233, G163+D254, G163+P256, V176+H198, V176+E210, V176+Y220, V176+L227, V176+T231, V176+N233, V176+D254, V176+P256, H198+E210, H198+Y220, H198+L227, H198+T231, H198+N233, H198+D254, H198+P256, E210+Y220, E210+L227, E210+T231, E210+N233, E210+D254, E210+P256, Y220+L227, Y220+T231, Y220+N233, Y220+D254, Y220+P256, L227+T231, L227+N233, L227+D254, L227+P256, T231+N233, T231+D254, T231+P256, N233+D254, N233+P256, and D254+P256, wherein numbering is according to SEQ ID NO: 1.

In one embodiment, the lipase variant comprises a modification in three positions corresponding to positions E1, V2, N33, F51, E56, L69, K98, V176, H198, E210, Y220, and L227 of SEQ ID NO: 1. Thus, in one embodiment, the lipase variant comprises a modification in three positions selected from the group consisting of: E1+V2+N33, E1+V2+F51, E1+V2+E56, E1+V2+L69, E1+V2+K98, E1+V2+V176, E1+V2+H198, E1+V2+E210, E1+V2+Y220, E1+V2+L227, E1+N33+F51, E1+N33+E56, E1+N33+L69, E1+N33+K98, E1+N33+V176, E1+N33+H198, E1+N33+E210, E1+N33+Y220, E1+N33+L227, E1+F51+E56, E1+F51+L69, E1+F51+K98, E1+F51+V176, E1+F51+H198, E1+F51+E210, E1+F51+Y220, E1+F51+L227, E1+E56+L69, E1+E56+K98, E1+E56+V176, E1+E56+H198, E1+E56+E210, E1+E56+Y220, E1+E56+L227, E1+L69+K98, E1+L69+V176, E1+L69+H198, E1+L69+E210, E1+L69+Y220, E1+L69+L227, E1+K98+V176, E1+K98+H198, E1+K98+E210, E1+K98+Y220, E1+K98+L227, E1+V176+H198, E1+V176+E210, E1+V176+Y220, E1+V176+L227, E1+H198+E210, E1+H198+Y220, E1+H198+L227, E1+E210+Y220, E1+E210+L227, E1+Y220+L227, V2+N33+F51, V2+N33+E56, V2+N33+L69, V2+N33+K98, V2+N33+V176, V2+N33+H198, V2+N33+E210, V2+N33+Y220, V2+N33+L227, V2+F51+E56, V2+F51+L69, V2+F51+K98, V2+F51+V176, V2+F51+H198, V2+F51+E210, V2+F51+Y220, V2+F51+L227, V2+E56+L69, V2+E56+K98, V2+E56+V176, V2+E56+H198, V2+E56+E210, V2+E56+Y220, V2+E56+L227, V2+L69+K98, V2+L69+V176, V2+L69+H198, V2+L69+E210, V2+L69+Y220, V2+L69+L227, V2+K98+V176, V2+K98+H198, V2+K98+E210, V2+K98+Y220, V2+K98+L227, V2+V176+H198, V2+V176+E210, V2+V176+Y220, V2+V176+L227, V2+H198+E210, V2+H198+Y220, V2+H198+L227, V2+E210+Y220, V2+E210+L227, V2+Y220+L227, N33+F51+E56, N33+F51+L69, N33+F51+K98, N33+F51+V176, N33+F51+H198, N33+F51+E210, N33+F51+Y220, N33+F51+L227, N33+E56+L69, N33+E56+K98, N33+E56+V176, N33+E56+H198, N33+E56+E210, N33+E56+Y220, N33+E56+L227, N33+L69+K98, N33+L69+V176, N33+L69+H198, N33+L69+E210, N33+L69+Y220, N33+L69+L227, N33+K98+V176, N33+K98+H198, N33+K98+E210, N33+K98+Y220, N33+K98+L227, N33+V176+H198, N33+V176+E210, N33+V176+Y220, N33+V176+L227, N33+H198+E210, N33+H198+Y220, N33+H198+L227, N33+E210+Y220, N33+E210+L227, N33+Y220+L227, F51+E56+L69, F51+E56+K98, F51+E56+V176, F51+E56+H198, F51+E56+E210, F51+E56+Y220, F51+E56+L227, F51+L69+K98, F51+L69+V176, F51+L69+H198, F51+L69+E210, F51+L69+Y220, F51+L69+L227, F51+K98+V176, F51+K98+H198, F51+K98+E210, F51+K98+Y220, F51+K98+L227, F51+V176+H198, F51+V176+E210, F51+V176+Y220, F51+V176+L227, F51+H198+E210, F51+H198+Y220, F51+H198+L227, F51+E210+Y220, F51+E210+L227, F51+Y220+L227, E56+L69+K98, E56+L69+V176, E56+L69+H198, E56+L69+E210, E56+L69+Y220, E56+L69+L227, E56+K98+V176, E56+K98+H198, E56+K98+E210, E56+K98+Y220, E56+K98+L227, E56+V176+H198, E56+V176+E210, E56+V176+Y220, E56+V176+L227, E56+H198+E210, E56+H198+Y220, E56+H198+L227, E56+E210+Y220, E56+E210+L227, E56+Y220+L227, L69+K98+V176, L69+K98+H198, L69+K98+E210, L69+K98+Y220, L69+K98+L227, L69+V176+H198, L69+V176+E210, L69+V176+Y220, L69+V176+L227, L69+H198+E210, L69+H198+Y220, L69+H198+L227, L69+E210+Y220, L69+E210+L227, L69+Y220+L227, K98+V176+H198, K98+V176+E210, K98+V176+Y220, K98+V176+L227, K98+H198+E210, K98+H198+Y220, K98+H198+L227, K98+E210+Y220, K98+E210+L227, K98+Y220+L227, V176+H198+E210, V176+H198+Y220, V176+H198+L227, V176+E210+Y220, V176+E210+L227, V176+Y220+L227, H198+E210+Y220, H198+E210+L227, H198+Y220+L227, and E210+Y220+L227, wherein numbering is according to SEQ ID NO: 1.

In one embodiment, the lipase variant comprises a modification in three positions corresponding to positions E1, V2, D27, N33, G38, F51, E56, L69, D96, K98, D111, G163, V176, H198, E210, Y220, L227, T231, N233, N233, D254, and P256, wherein numbering is according to SEQ ID NO: 1. Thus, in a particular embodiment, the lipase variant comprises a modification in three positions selected from the group consisting of: E1+V2+D27, E1+V2+N33, E1+V2+G38, E1+V2+F51, E1+V2+E56, E1+V2+L69, E1+V2+D96, E1+V2+K98, E1+V2+D111, E1+V2+G163, E1+V2+V176, E1+V2+H198, E1+V2+E210, E1+V2+Y220, E1+V2+L227, E1+V2+T231, E1+V2+N233, E1+V2+D254, E1+V2+P256, E1+D27+N33, E1+D27+G38, E1+D27+F51, E1+D27+E56, E1+D27+L69, E1+D27+D96, E1+D27+K98, E1+D27+D111, E1+D27+G163, E1+D27+V176, E1+D27+H198, E1+D27+E210, E1+D27+Y220, E1+D27+L227, E1+D27+T231, E1+D27+N233, E1+D27+D254, E1+D27+P256, E1+N33+G38, E1+N33+F51, E1+N33+E56, E1+N33+L69, E1+N33+D96, E1+N33+K98, E1+N33+D111, E1+N33+G163, E1+N33+V176, E1+N33+H198, E1+N33+E210, E1+N33+Y220, E1+N33+L227, E1+N33+T231, E1+N33+N233, E1+N33+D254, E1+N33+P256, E1+G38+F51, E1+G38+E56, E1+G38+L69, E1+G38+D96, E1+G38+K98, E1+G38+D111, E1+G38+G163, E1+G38+V176, E1+G38+H198, E1+G38+E210, E1+G38+Y220, E1+G38+L227, E1+G38+T231, E1+G38+N233, E1+G38+D254, E1+G38+P256, E1+F51+E56, E1+F51+L69, E1+F51+D96, E1+F51+K98, E1+F51+D111, E1+F51+G163, E1+F51+V176, E1+F51+H198, E1+F51+E210, E1+F51+Y220, E1+F51+L227, E1+F51+T231, E1+F51+N233, E1+F51+D254, E1+F51+P256, E1+E56+L69, E1+E56+D96, E1+E56+K98, E1+E56+D111, E1+E56+G163, E1+E56+V176, E1+E56+H198, E1+E56+E210, E1+E56+Y220, E1+E56+L227, E1+E56+T231, E1+E56+N233, E1+E56+D254, E1+E56+

P256, E1+L69+D96, E1+L69+K98, E1+L69+D111, E1+L69+G163, E1+L69+V176, E1+L69+H198, E1+L69+E210, E1+L69+Y220, E1+L69+L227, E1+L69+T231, E1+L69+N233, E1+L69+D254, E1+L69+P256, E1+D96+K98, E1+D96+D111, E1+D96+G163, E1+D96+V176, E1+D96+H198, E1+D96+E210, E1+D96+Y220, E1+D96+L227, E1+D96+T231, E1+D96+N233, E1+D96+D254, E1+D96+P256, E1+K98+D111, E1+K98+G163, E1+K98+V176, E1+K98+H198, E1+K98+E210, E1+K98+Y220, E1+K98+L227, E1+K98+T231, E1+K98+N233, E1+K98+D254, E1+K98+P256, E1+D111+G163, E1+D111+V176, E1+D111+H198, E1+D111+E210, E1+D111+Y220, E1+D111+L227, E1+D111+T231, E1+D111+N233, E1+D111+D254, E1+D111+P256, E1+G163+V176, E1+G163+H198, E1+G163+E210, E1+G163+Y220, E1+G163+L227, E1+G163+T231, E1+G163+N233, E1+G163+D254, E1+G163+P256, E1+V176+H198, E1+V176+E210, E1+V176+Y220, E1+V176+L227, E1+V176+T231, E1+V176+N233, E1+V176+D254, E1+V176+P256, E1+H198+E210, E1+H198+Y220, E1+H198+L227, E1+H198+T231, E1+H198+N233, E1+H198+D254, E1+H198+P256, E1+E210+Y220, E1+E210+L227, E1+E210+T231, E1+E210+N233, E1+E210+D254, E1+E210+P256, E1+Y220+L227, E1+Y220+T231, E1+Y220+N233, E1+Y220+D254, E1+Y220+P256, E1+L227+T231, E1+L227+N233, E1+L227+D254, E1+L227+P256, E1+T231+N233, E1+T231+D254, E1+T231+P256, E1+N233+D254, E1+N233+P256, E1+D254+P256, V2+D27+N33, V2+D27+G38, V2+D27+F51, V2+D27+E56, V2+D27+L69, V2+D27+D96, V2+D27+K98, V2+D27+D111, V2+D27+G163, V2+D27+V176, V2+D27+H198, V2+D27+E210, V2+D27+Y220, V2+D27+L227, V2+D27+T231, V2+D27+N233, V2+D27+D254, V2+D27+P256, V2+N33+G38, V2+N33+F51, V2+N33+E56, V2+N33+L69, V2+N33+D96, V2+N33+K98, V2+N33+D111, V2+N33+G163, V2+N33+V176, V2+N33+H198, V2+N33+E210, V2+N33+Y220, V2+N33+L227, V2+N33+T231, V2+N33+N233, V2+N33+D254, V2+N33+P256, V2+G38+F51, V2+G38+E56, V2+G38+L69, V2+G38+D96, V2+G38+K98, V2+G38+D111, V2+G38+G163, V2+G38+V176, V2+G38+H198, V2+G38+E210, V2+G38+Y220, V2+G38+L227, V2+G38+T231, V2+G38+N233, V2+G38+D254, V2+G38+P256, V2+F51+E56, V2+F51+L69, V2+F51+D96, V2+F51+K98, V2+F51+D111, V2+F51+G163, V2+F51+V176, V2+F51+H198, V2+F51+E210, V2+F51+Y220, V2+F51+L227, V2+F51+T231, V2+F51+N233, V2+F51+D254, V2+F51+P256, V2+E56+L69, V2+E56+D96, V2+E56+K98, V2+E56+D111, V2+E56+G163, V2+E56+V176, V2+E56+H198, V2+E56+E210, V2+E56+Y220, V2+E56+L227, V2+E56+T231, V2+E56+N233, V2+E56+D254, V2+E56+P256, V2+L69+D96, V2+L69+K98, V2+L69+D111, V2+L69+G163, V2+L69+V176, V2+L69+H198, V2+L69+E210, V2+L69+Y220, V2+L69+L227, V2+L69+T231, V2+L69+N233, V2+L69+D254, V2+L69+P256, V2+D96+K98, V2+D96+D111, V2+D96+G163, V2+D96+V176, V2+D96+H198, V2+D96+E210, V2+D96+Y220, V2+D96+L227, V2+D96+T231, V2+D96+N233, V2+D96+D254, V2+D96+P256, V2+K98+D111, V2+K98+G163, V2+K98+V176, V2+K98+H198, V2+K98+E210, V2+K98+Y220, V2+K98+L227, V2+K98+T231, V2+K98+N233, V2+K98+D254, V2+K98+P256, V2+D111+G163, V2+D111+V176, V2+D111+H198, V2+D111+E210, V2+D111+Y220, V2+D111+L227, V2+D111+T231, V2+D111+N233, V2+D111+D254, V2+D111+P256, V2+G163+V176, V2+G163+H198, V2+G163+E210, V2+G163+Y220, V2+G163+L227, V2+G163+T231, V2+G163+N233, V2+G163+D254, V2+G163+P256, V2+V176+H198, V2+V176+E210, V2+V176+Y220, V2+V176+L227, V2+V176+T231, V2+V176+N233, V2+V176+D254, V2+V176+P256, V2+H198+E210, V2+H198+Y220, V2+H198+L227, V2+H198+T231, V2+H198+N233, V2+H198+D254, V2+H198+P256, V2+E210+Y220, V2+E210+L227, V2+E210+T231, V2+E210+N233, V2+E210+D254, V2+E210+P256, V2+Y220+L227, V2+Y220+T231, V2+Y220+N233, V2+Y220+D254, V2+Y220+P256, V2+L227+T231, V2+L227+N233, V2+L227+D254, V2+L227+P256, V2+T231+N233, V2+T231+D254, V2+T231+P256, V2+N233+D254, V2+N233+P256, V2+D254+P256, D27+N33+G38, D27+N33+F51, D27+N33+E56, D27+N33+L69, D27+N33+D96, D27+N33+K98, D27+N33+D111, D27+N33+G163, D27+N33+V176, D27+N33+H198, D27+N33+E210, D27+N33+Y220, D27+N33+L227, D27+N33+T231, D27+N33+N233, D27+N33+D254, D27+N33+P256, D27+G38+F51, D27+G38+E56, D27+G38+L69, D27+G38+D96, D27+G38+K98, D27+G38+D111, D27+G38+G163, D27+G38+V176, D27+G38+H198, D27+G38+E210, D27+G38+Y220, D27+G38+L227, D27+G38+T231, D27+G38+N233, D27+G38+D254, D27+G38+P256, D27+F51+E56, D27+F51+L69, D27+F51+D96, D27+F51+K98, D27+F51+D111, D27+F51+G163, D27+F51+V176, D27+F51+H198, D27+F51+E210, D27+F51+Y220, D27+F51+L227, D27+F51+T231, D27+F51+N233, D27+F51+D254, D27+F51+P256, D27+E56+L69, D27+E56+D96, D27+E56+K98, D27+E56+D111, D27+E56+G163, D27+E56+V176, D27+E56+H198, D27+E56+E210, D27+E56+Y220, D27+E56+L227, D27+E56+T231, D27+E56+N233, D27+E56+D254, D27+E56+P256, D27+L69+D96, D27+L69+K98, D27+L69+D111, D27+L69+G163, D27+L69+V176, D27+L69+H198, D27+L69+E210, D27+L69+Y220, D27+L69+L227, D27+L69+T231, D27+L69+N233, D27+L69+D254, D27+L69+P256, D27+D96+K98, D27+D96+D111, D27+D96+G163, D27+D96+V176, D27+D96+H198, D27+D96+E210, D27+D96+Y220, D27+D96+L227, D27+D96+T231, D27+D96+N233, D27+D96+D254, D27+D96+P256, D27+K98+D111, D27+K98+G163, D27+K98+V176, D27+K98+H198, D27+K98+E210, D27+K98+Y220, D27+K98+L227, D27+K98+T231, D27+K98+N233, D27+K98+D254, D27+K98+P256, D27+D111+G163, D27+D111+V176, D27+D111+H198, D27+D111+E210, D27+D111+Y220, D27+D111+L227, D27+D111+T231, D27+D111+N233, D27+D111+D254, D27+D111+P256, D27+G163+V176, D27+G163+H198, D27+G163+E210, D27+G163+Y220, D27+G163+L227, D27+G163+T231, D27+G163+N233, D27+G163+D254, D27+G163+P256, D27+V176+H198, D27+V176+E210, D27+V176+Y220, D27+V176+L227, D27+V176+T231, D27+V176+N233, D27+V176+D254, D27+V176+P256, D27+H198+E210, D27+H198+Y220, D27+H198+L227, D27+H198+T231, D27+H198+N233, D27+H198+D254, D27+H198+P256, D27+E210+Y220, D27+E210+L227, D27+E210+T231, D27+E210+N233, D27+E210+D254, D27+E210+P256, D27+Y220+L227, D27+Y220+T231, D27+Y220+N233, D27+Y220+D254, D27+Y220+P256, D27+L227+T231, D27+L227+N233, D27+L227+D254, D27+L227+P256, D27+T231+N233, D27+T231+D254, D27+T231+P256, D27+N233+D254, D27+N233+P256, D27+D254+P256, N33+G38+F51, N33+G38+E56, N33+G38+L69, N33+G38+D96, N33+G38+K98, N33+G38+D111, N33+G38+G163, N33+G38+V176, N33+G38+H198, N33+G38+E210, N33+G38+Y220, N33+G38+L227, N33+G38+T231, N33+G38+N233, N33+G38+D254, N33+G38+P256, N33+F51+E56, N33+F51+L69, N33+

F51+D96, N33+F51+K98, N33+F51+D111, N33+F51+G163, N33+F51+V176, N33+F51+H198, N33+F51+E210, N33+F51+Y220, N33+F51+L227, N33+F51+T231, N33+F51+N233, N33+F51+D254, N33+F51+P256, N33+E56+L69, N33+E56+D96, N33+E56+K98, N33+E56+D111, N33+E56+G163, N33+E56+V176, N33+E56+H198, N33+E56+E210, N33+E56+Y220, N33+E56+L227, N33+E56+T231, N33+E56+N233, N33+E56+D254, N33+E56+P256, N33+L69+D96, N33+L69+K98, N33+L69+D111, N33+L69+G163, N33+L69+V176, N33+L69+H198, N33+L69+E210, N33+L69+Y220, N33+L69+L227, N33+L69+T231, N33+L69+N233, N33+L69+D254, N33+L69+P256, N33+D96+K98, N33+D96+D111, N33+D96+G163, N33+D96+V176, N33+D96+H198, N33+D96+E210, N33+D96+Y220, N33+D96+L227, N33+D96+T231, N33+D96+N233, N33+D96+D254, N33+D96+P256, N33+K98+D111, N33+K98+G163, N33+K98+V176, N33+K98+H198, N33+K98+E210, N33+K98+Y220, N33+K98+L227, N33+K98+T231, N33+K98+N233, N33+K98+D254, N33+K98+P256, N33+D111+G163, N33+D111+V176, N33+D111+H198, N33+D111+E210, N33+D111+Y220, N33+D111+L227, N33+D111+T231, N33+D111+N233, N33+D111+D254, N33+D111+P256, N33+G163+V176, N33+G163+H198, N33+G163+E210, N33+G163+Y220, N33+G163+L227, N33+G163+T231, N33+G163+N233, N33+G163+D254, N33+G163+P256, N33+V176+H198, N33+V176+E210, N33+V176+Y220, N33+V176+L227, N33+V176+T231, N33+V176+N233, N33+V176+D254N33+V176+P256, N33+H198+E210, N33+H198+Y220, N33+H198+L227, N33+H198+T231, N33+H198+N233, N33+H198+D254, N33+H198+P256, N33+E210+Y220, N33+E210+L227, N33+E210+T231, N33+E210+N233, N33+E210+D254, N33+E210+P256, N33+Y220+L227, N33+Y220+T231, N33+Y220+N233, N33+Y220+D254, N33+Y220+P256, N33+L227+T231, N33+L227+N233, N33+L227+D254, N33+L227+P256, N33+T231+N233, N33+T231+D254, N33+T231+P256, N33+N233+D254, N33+N233+P256, N33+D254+P256, G38+F51+E56, G38+F51+L69, G38+F51+D96, G38+F51+K98, G38+F51+D111, G38+F51+G163, G38+F51+V176, G38+F51+H198, G38+F51+E210, G38+F51+Y220, G38+F51+L227, G38+F51+T231, G38+F51+N233, G38+F51+D254, G38+F51+P256, G38+E56+L69, G38+E56+D96, G38+E56+K98, G38+E56+D111, G38+E56+G163, G38+E56+V176, G38+E56+H198, G38+E56+E210, G38+E56+Y220, G38+E56+L227, G38+E56+T231, G38+E56+N233, G38+E56+D254, G38+E56+P256, G38+L69+D96, G38+L69+K98, G38+L69+D111, G38+L69+G163, G38+L69+V176, G38+L69+H198, G38+L69+E210, G38+L69+Y220, G38+L69+L227, G38+L69+T231, G38+L69+N233, G38+L69+D254, G38+L69+P256, G38+D96+K98, G38+D96+D111, G38+D96+G163, G38+D96+V176, G38+D96+H198, G38+D96+E210, G38+D96+Y220, G38+D96+L227, G38+D96+T231, G38+D96+N233, G38+D96+D254, G38+D96+P256, G38+K98+D111, G38+K98+G163, G38+K98+V176, G38+K98+H198, G38+K98+E210, G38+K98+Y220, G38+K98+L227, G38+K98+T231, G38+K98+N233, G38+K98+D254, G38+K98+P256, G38+D111+G163, G38+D111+V176, G38+D111+H198, G38+D111+E210, G38+D111+Y220, G38+D111+L227, G38+D111+T231, G38+D111+N233, G38+D111+D254, G38+D111+P256, G38+G163+V176, G38+G163+H198, G38+G163+E210, G38+G163+Y220, G38+G163+L227, G38+G163+T231, G38+G163+N233, G38+G163+D254, G38+G163+P256, G38+V176+H198, G38+V176+E210, G38+V176+Y220, G38+V176+L227, G38+V176+T231, G38+V176+N233, G38+V176+D254, G38+V176+P256, G38+H198+E210, G38+H198+Y220, G38+H198+L227, G38+H198+T231, G38+H198+N233, G38+H198+D254, G38+H198+P256, G38+E210+Y220, G38+E210+L227, G38+E210+T231, G38+E210+N233, G38+E210+D254, G38+E210+P256, G38+Y220+L227, G38+Y220+T231, G38+Y220+N233, G38+Y220+D254, G38+Y220+P256, G38+L227+T231, G38+L227+N233, G38+L227+D254, G38+L227+P256, G38+T231+N233, G38+T231+D254, G38+T231+P256, G38+N233+D254, G38+N233+P256, G38+D254+P256, F51+E56+L69, F51+E56+D96, F51+E56+K98, F51+E56+D111, F51+E56+G163, F51+E56+V176, F51+E56+H198, F51+E56+E210, F51+E56+Y220, F51+E56+L227, F51+E56+T231, F51+E56+N233, F51+E56+D254, F51+E56+P256, F51+L69+D96, F51+L69+K98, F51+L69+D111, F51+L69+G163, F51+L69+V176, F51+L69+H198, F51+L69+E210, F51+L69+Y220, F51+L69+L227, F51+L69+T231, F51+L69+N233, F51+L69+D254, F51+L69+P256, F51+D96+K98, F51+D96+D111, F51+D96+G163, F51+D96+V176, F51+D96+H198, F51+D96+E210, F51+D96+Y220, F51+D96+L227, F51+D96+T231, F51+D96+N233, F51+D96+D254, F51+D96+P256, F51+K98+D111, F51+K98+G163, F51+K98+V176, F51+K98+H198, F51+K98+E210, F51+K98+Y220, F51+K98+L227, F51+K98+T231, F51+K98+N233, F51+K98+D254, F51+K98+P256, F51+D111+G163, F51+D111+V176, F51+D111+H198, F51+D111+E210, F51+D111+Y220, F51+D111+L227, F51+D111+T231, F51+D111+N233, F51+D111+D254, F51+D111+P256, F51+G163+V176, F51+G163+H198, F51+G163+E210, F51+G163+Y220, F51+G163+L227, F51+G163+T231, F51+G163+N233, F51+G163+D254, F51+G163+P256, F51+V176+H198, F51+V176+E210, F51+V176+Y220, F51+V176+L227, F51+V176+T231, F51+V176+N233, F51+V176+D254, F51+V176+P256, F51+H198+E210, F51+H198+Y220, F51+H198+L227, F51+H198+T231, F51+H198+N233, F51+H198+D254, F51+H198+P256, F51+E210+Y220, F51+E210+L227, F51+E210+T231, F51+E210+N233, F51+E210+D254, F51+E210+P256, F51+Y220+L227, F51+Y220+T231, F51+Y220+N233, F51+Y220+D254, F51+Y220+P256, F51+L227+T231, F51+L227+N233, F51+L227+D254, F51+L227+P256, F51+T231+N233, F51+T231+D254, F51+T231+P256, F51+N233+D254, F51+N233+P256, F51+D254+P256, E56+L69+D96, E56+L69+K98, E56+L69+D111, E56+L69+G163, E56+L69+V176, E56+L69+H198, E56+L69+E210, E56+L69+Y220, E56+L69+L227, E56+L69+T231, E56+L69+N233, E56+L69+D254, E56+L69+P256, E56+D96+K98, E56+D96+D111, E56+D96+G163, E56+D96+V176, E56+D96+H198, E56+D96+E210, E56+D96+Y220, E56+D96+L227, E56+D96+T231, E56+D96+N233, E56+D96+D254, E56+D96+P256, E56+K98+D111, E56+K98+G163, E56+K98+V176, E56+K98+H198, E56+K98+E210, E56+K98+Y220, E56+K98+L227, E56+K98+T231, E56+K98+N233, E56+K98+D254, E56+K98+P256, E56+D111+G163, E56+D111+V176, E56+D111+H198, E56+D111+E210, E56+D111+Y220, E56+D111+L227, E56+D111+T231, E56+D111+N233, E56+D111+D254, E56+D111+P256, E56+G163+V176, E56+G163+H198, E56+G163+E210, E56+G163+Y220, E56+G163+L227, E56+G163+T231, E56+G163+N233, E56+G163+D254, E56+G163+P256, E56+V176+H198, E56+V176+E210, E56+V176+Y220, E56+V176+L227, E56+V176+T231, E56+V176+N233, E56+V176+D254, E56+V176+P256, E56+H198+E210, E56+H198+Y220, E56+H198+L227, E56+H198+T231, E56+H198+N233, E56+H198+D254, E56+H198+P256, E56+E210+Y220, E56+E210+L227, E56+E210+T231, E56+E210+N233, E56+E210+D254, E56+E210+P256, E56+Y220+L227, E56+Y220+T231, E56+Y220+N233, E56+Y220+D254, E56+Y220+

P256, E56+L227+T231, E56+L227+N233, E56+L227+D254, E56+L227+P256, E56+T231+N233, E56+T231+D254, E56+T231+P256, E56+N233+D254, E56+N233+P256, E56+D254+P256, L69+D96+K98, L69+D96+D111, L69+D96+G163, L69+D96+V176, L69+D96+H198, L69+D96+E210, L69+D96+Y220, L69+D96+L227, L69+D96+T231, L69+D96+N233, L69+D96+D254, L69+D96+P256, L69+K98+D111, L69+K98+G163, L69+K98+V176, L69+K98+H198, L69+K98+E210, L69+K98+Y220, L69+K98+L227, L69+K98+T231, L69+K98+N233, L69+K98+D254, L69+K98+P256, L69+D111+G163, L69+D111+V176, L69+D111+H198, L69+D111+E210, L69+D111+Y220, L69+D111+L227, L69+D111+T231, L69+D111+N233, L69+D111+D254, L69+D111+P256, L69+G163+V176, L69+G163+H198, L69+G163+E210, L69+G163+Y220, L69+G163+L227, L69+G163+T231, L69+G163+N233, L69+G163+D254, L69+G163+P256, L69+V176+H198, L69+V176+E210, L69+V176+Y220, L69+V176+L227, L69+V176+T231, L69+V176+N233, L69+V176+D254, L69+V176+P256, L69+H198+E210, L69+H198+Y220, L69+H198+L227, L69+H198+T231, L69+H198+N233, L69+H198+D254, L69+H198+P256, L69+E210+Y220, L69+E210+L227, L69+E210+T231, L69+E210+N233, L69+E210+D254, L69+E210+P256, L69+Y220+L227, L69+Y220+T231, L69+Y220+N233, L69+Y220+D254, L69+Y220+P256, L69+L227+T231, L69+L227+N233, L69+L227+D254, L69+L227+P256, L69+T231+N233, L69+T231+D254, L69+T231+P256, L69+N233+D254, L69+N233+P256, L69+D254+P256, D96+K98+D111, D96+K98+G163, D96+K98+V176, D96+K98+H198, D96+K98+E210, D96+K98+Y220, D96+K98+L227, D96+K98+T231, D96+K98+N233, D96+K98+D254, D96+K98+P256, D96+D111+G163, D96+D111+V176, D96+D111+H198, D96+D111+E210, D96+D111+Y220, D96+D111+L227, D96+D111+T231, D96+D111+N233, D96+D111+D254, D96+D111+P256, D96+G163+V176, D96+G163+H198, D96+G163+E210, D96+G163+Y220, D96+G163+L227, D96+G163+T231, D96+G163+N233, D96+G163+D254, D96+G163+P256, D96+V176+H198, D96+V176+E210, D96+V176+Y220, D96+V176+L227, D96+V176+T231, D96+V176+N233, D96+V176+D254, D96+V176+P256, D96+H198+E210, D96+H198+Y220, D96+H198+L227, D96+H198+T231, D96+H198+N233, D96+H198+D254, D96+H198+P256, D96+E210+Y220, D96+E210+L227, D96+E210+T231, D96+E210+N233, D96+E210+D254, D96+E210+P256, D96+Y220+L227, D96+Y220+T231, D96+Y220+N233, D96+Y220+D254, D96+Y220+P256, D96+L227+T231, D96+L227+N233, D96+L227+D254, D96+L227+P256, D96+T231+N233, D96+T231+D254, D96+T231+P256, D96+N233+D254, D96+N233+P256, D96+D254+P256, K98+D111+G163, K98+D111+V176, K98+D111+H198, K98+D111+E210, K98+D111+Y220, K98+D111+L227, K98+D111+T231, K98+D111+N233, K98+D111+D254, K98+D111+P256, K98+G163+V176, K98+G163+H198, K98+G163+E210, K98+G163+Y220, K98+G163+L227, K98+G163+T231, K98+G163+N233, K98+G163+D254, K98+G163+P256, K98+V176+H198, K98+V176+E210, K98+V176+Y220, K98+V176+L227, K98+V176+T231, K98+V176+N233, K98+V176+D254, K98+V176+P256, K98+H198+E210, K98+H198+Y220, K98+H198+L227, K98+H198+T231, K98+H198+N233, K98+H198+D254, K98+H198+P256, K98+E210+Y220, K98+E210+L227, K98+E210+T231, K98+E210+N233, K98+E210+D254, K98+E210+P256, K98+Y220+L227, K98+Y220+T231, K98+Y220+N233, K98+Y220+D254, K98+Y220+P256, K98+L227+T231, K98+L227+N233, K98+L227+D254, K98+L227+P256, K98+T231+N233, K98+T231+D254, K98+T231+P256, K98+N233+D254, K98+N233+P256, K98+D254+P256, D111+G163+V176, D111+G163+H198, D111+G163+E210, D111+G163+Y220, D111+G163+L227, D111+G163+T231, D111+G163+N233, D111+G163+D254, D111+G163+P256, D111+V176+H198, D111+V176+E210, D111+V176+Y220, D111+V176+L227, D111+V176+T231, D111+V176+N233, D111+V176+D254, D111+V176+P256, D111+H198+E210, D111+H198+Y220, D111+H198+L227, D111+H198+T231, D111+H198+N233, D111+H198+D254, D111+H198+P256, D111+E210+Y220, D111+E210+L227, D111+E210+T231, D111+E210+N233, D111+E210+D254, D111+E210+P256, D111+Y220+L227, D111+Y220+T231, D111+Y220+N233, D111+Y220+D254, D111+Y220+P256, D111+L227+T231, D111+L227+N233, D111+L227+D254, D111+L227+P256, D111+T231+N233, D111+T231+D254, D111+T231+P256, D111+N233+D254, D111+N233+P256, D111+D254+P256, G163+V176+H198, G163+V176+E210, G163+V176+Y220, G163+V176+L227, G163+V176+T231, G163+V176+N233, G163+V176+D254, G163+V176+P256, G163+H198+E210, G163+H198+Y220, G163+H198+L227, G163+H198+T231, G163+H198+N233, G163+H198+D254, G163+H198+P256, G163+E210+Y220, G163+E210+L227, G163+E210+T231, G163+E210+N233, G163+E210+D254, G163+E210+P256, G163+Y220+L227, G163+Y220+T231, G163+Y220+N233, G163+Y220+D254, G163+Y220+P256, G163+L227+T231, G163+L227+N233, G163+L227+D254, G163+L227+P256, G163+T231+N233, G163+T231+D254, G163+T231+P256, G163+N233+D254, G163+N233+P256, G163+D254+P256, V176+H198+E210, V176+H198+Y220, V176+H198+L227, V176+H198+T231, V176+H198+N233, V176+H198+D254, V176+H198+P256, V176+E210+Y220, V176+E210+L227, V176+E210+T231, V176+E210+N233, V176+E210+D254, V176+E210+P256, V176+Y220+L227, V176+Y220+T231, V176+Y220+N233, V176+Y220+D254, V176+Y220+P256, V176+L227+T231, V176+L227+N233, V176+L227+D254, V176+L227+P256, V176+T231+N233, V176+T231+D254, V176+T231+P256, V176+N233+D254, V176+N233+P256, V176+D254+P256, H198+E210+Y220, H198+E210+L227, H198+E210+T231, H198+E210+N233, H198+E210+D254, H198+E210+P256, H198+Y220+L227, H198+Y220+T231, H198+Y220+N233, H198+Y220+D254, H198+Y220+P256, H198+L227+T231, H198+L227+N233, H198+L227+D254, H198+L227+P256, H198+T231+N233, H198+T231+D254, H198+T231+P256, H198+N233+D254, H198+N233+P256, H198+D254+P256, E210+Y220+L227, E210+Y220+T231, E210+Y220+N233, E210+Y220+D254, E210+Y220+P256, E210+L227+T231, E210+L227+N233, E210+L227+D254, E210+L227+P256, E210+T231+N233, E210+T231+D254, E210+T231+P256, E210+N233+D254, E210+N233+P256, E210+D254+P256, Y220+L227+T231, Y220+L227+N233, Y220+L227+D254, Y220+L227+P256, Y220+T231+N233, Y220+T231+D254, Y220+T231+P256, Y220+N233+D254, Y220+N233+P256, Y220+D254+P256, L227+T231+N233, L227+T231+D254, L227+T231+P256, L227+N233+D254, L227+N233+P256, L227+D254+P256, T231+N233+D254, T231+N233+P256, T231+D254+P256, and N233+D254+P256, wherein numbering is according to SEQ ID NO: 1.

In one embodiment, the composition comprises a lipase variant comprising at least one of the following modifications; E1C, V2Y, D27R, N33K, G38A, F51V, E56K, L69R, D96E, K98I, D111A, G163K, V176L, H198S, E210K, Y220F, L227G, T231R, N233R, N233C, D254S, and P256T, wherein numbering is according to SEQ ID NO: 1.

In one embodiment, the lipase variant comprises two substitutions corresponding to the substitutions selected from the group consisting of: E1C+V2Y, E1C+D27R, E1C+N33K, E1C+G38A, E1C+F51V, E1C+E56K, E1C+L69R, E1C+D96E, E1C+K98I, E1C+D111A, E1C+G163K, E1C+V176L, E1C+H198S, E1C+E210K, E1C+Y220F, E1C+L227G, E1C+T231R, E1C+N233R, E1C+N233C, E1C+D254S, E1C+P256T, V2Y+D27R, V2Y+N33K, V2Y+G38A, V2Y+F51V, V2Y+E56K, V2Y+L69R, V2Y+D96E, V2Y+K98I, V2Y+D111A, V2Y+G163K, V2Y+V176L, V2Y+H198S, V2Y+E210K, V2Y+Y220F, V2Y+L227G, V2Y+T231R, V2Y+N233R, V2Y+N233C, V2Y+D254S, V2Y+P256T, D27R+N33K, D27R+G38A, D27R+F51V, D27R+E56K, D27R+L69R, D27R+D96E, D27R+K98I, D27R+D111A, D27R+G163K, D27R+V176L, D27R+H198S, D27R+E210K, D27R+Y220F, D27R+L227G, D27R+T231R, D27R+N233R, D27R+N233C, D27R+D254S, D27R+P256T, N33K+G38A, N33K+F51V, N33K+E56K, N33K+L69R, N33K+D96E, N33K+K98I, N33K+D111A, N33K+G163K, N33K+V176L, N33K+H198S, N33K+E210K, N33K+Y220F, N33K+L227G, N33K+T231R, N33K+N233R, N33K+N233C, N33K+D254S, N33K+P256T, G38A+F51V, G38A+E56K, G38A+L69R, G38A+D96E, G38A+K98I, G38A+D111A, G38A+G163K, G38A+V176L, G38A+H198S, G38A+E210K, G38A+Y220F, G38A+L227G, G38A+T231R, G38A+N233R, G38A+N233C, G38A+D254S, G38A+P256T, F51V+E56K, F51V+L69R, F51V+D96E, F51V+K98I, F51V+D111A, F51V+G163K, F51V+V176L, F51V+H198S, F51V+E210K, F51V+Y220F, F51V+L227G, F51V+T231R, F51V+N233R, F51V+N233C, F51V+D254S, F51V+P256T, E56K+L69R, E56K+D96E, E56K+K98I, E56K+D111A, E56K+G163K, E56K+V176L, E56K+H198S, E56K+E210K, E56K+Y220F, E56K+L227G, E56K+T231R, E56K+N233R, E56K+N233C, E56K+D254S, E56K+P256T, L69R+D96E, L69R+K98I, L69R+D111A, L69R+G163K, L69R+V176L, L69R+H198S, L69R+E210K, L69R+Y220F, L69R+L227G, L69R+T231R, L69R+N233R, L69R+N233C, L69R+D254S, L69R+P256T, D96E+K98I, D96E+D111A, D96E+G163K, D96E+V176L, D96E+H198S, D96E+E210K, D96E+Y220F, D96E+L227G, D96E+T231R, D96E+N233R, D96E+N233C, D96E+D254S, D96E+P256T, K98I+D111A, K98I+G163K, K98I+V176L, K98I+H198S, K98I+E210K, K98I+Y220F, K98I+L227G, K98I+T231R, K98I+N233R, K98I+N233C, K98I+D254S, K98I+P256T, D111A+G163K, D111A+V176L, D111A+H198S, D111A+E210K, D111A+Y220F, D111A+L227G, D111A+T231R, D111A+N233R, D111A+N233C, D111A+D254S, D111A+P256T, G163K+V176L, G163K+H198S, G163K+E210K, G163K+Y220F, G163K+L227G, G163K+T231R, G163K+N233R, G163K+N233C, G163K+D254S, G163K+P256T, V176L+H198S, V176L+E210K, V176L+Y220F, V176L+L227G, V176L+T231R, V176L+N233R, V176L+N233C, V176L+D254S, V176L+P256T, H198S+E210K, H198S+Y220F, H198S+L227G, H198S+T231R, H198S+N233R, H198S+N233C, H198S+D254S, H198S+P256T, E210K+Y220F, E210K+L227G, E210K+T231R, E210K+N233R, E210K+N233C, E210K+D254S, E210K+P256T, Y220F+L227G, Y220F+T231R, Y220F+N233R, Y220F+N233C, Y220F+D254S, Y220F+P256T, L227G+T231R, L227G+N233R, L227G+N233C, L227G+D254S, L227G+P256T, T231R+N233R, T231R+N233C, T231R+D254S, T231R+P256T, N233R+N233C, N233R+D254S, N233R+P256T, N233C+D254S, N233C+P256T, and D254S+P256T, wherein numbering is according to SEQ ID NO: 1.

In one embodiment, the lipase variant comprises three substitutions corresponding to substitutions selected from the group consisting of: E1C+V2Y+D27R, E1C+V2Y+N33K, E1C+V2Y+G38A, E1C+V2Y+F51V, E1C+V2Y+E56K, E1C+V2Y+L69R, E1C+V2Y+D96E, E1C+V2Y+K98I, E1C+V2Y+D111A, E1C+V2Y+G163K, E1C+V2Y+V176L, E1C+V2Y+H198S, E1C+V2Y+E210K, E1C+V2Y+Y220F, E1C+V2Y+L227G, E1C+V2Y+T231R, E1C+V2Y+N233R, E1C+V2Y+N233C, E1C+V2Y+D254S, E1C+V2Y+P256T, E1C+D27R+N33K, E1C+D27R+G38A, E1C+D27R+F51V, E1C+D27R+E56K, E1C+D27R+L69R, E1C+D27R+D96E, E1C+D27R+K98I, E1C+D27R+D111A, E1C+D27R+G163K, E1C+D27R+V176L, E1C+D27R+H198S, E1C+D27R+E210K, E1C+D27R+Y220F, E1C+D27R+L227G, E1C+D27R+T231R, E1C+D27R+N233R, E1C+D27R+N233C, E1C+D27R+D254S, E1C+D27R+P256T, E1C+N33K+G38A, E1C+N33K+F51V, E1C+N33K+E56K, E1C+N33K+L69R, E1C+N33K+D96E, E1C+N33K+K98I, E1C+N33K+D111A, E1C+N33K+G163K, E1C+N33K+V176L, E1C+N33K+H198S, E1C+N33K+E210K, E1C+N33K+Y220F, E1C+N33K+L227G, E1C+N33K+T231R, E1C+N33K+N233R, E1C+N33K+N233C, E1C+N33K+D254S, E1C+N33K+P256T, E1C+G38A+F51V, E1C+G38A+E56K, E1C+G38A+L69R, E1C+G38A+D96E, E1C+G38A+K98I, E1C+G38A+D111A, E1C+G38A+G163K, E1C+G38A+V176L, E1C+G38A+H198S, E1C+G38A+E210K, E1C+G38A+Y220F, E1C+G38A+L227G, E1C+G38A+T231R, E1C+G38A+N233R, E1C+G38A+N233C, E1C+G38A+D254S, E1C+G38A+P256T, E1C+F51V+E56K, E1C+F51V+L69R, E1C+F51V+D96E, E1C+F51V+K98I, E1C+F51V+D111A, E1C+F51V+G163K, E1C+F51V+V176L, E1C+F51V+H198S, E1C+F51V+E210K, E1C+F51V+Y220F, E1C+F51V+L227G, E1C+F51V+T231R, E1C+F51V+N233R, E1C+F51V+N233C, E1C+F51V+D254S, E1C+F51V+P256T, E1C+E56K+L69R, E1C+E56K+D96E, E1C+E56K+K98I, E1C+E56K+D111A, E1C+E56K+G163K, E1C+E56K+V176L, E1C+E56K+H198S, E1C+E56K+E210K, E1C+E56K+Y220F, E1C+E56K+L227G, E1C+E56K+T231R, E1C+E56K+N233R, E1C+E56K+N233C, E1C+E56K+D254S, E1C+E56K+P256T, E1C+L69R+D96E, E1C+L69R+K98I, E1C+L69R+D111A, E1C+L69R+G163K, E1C+L69R+V176L, E1C+L69R+H198S, E1C+L69R+E210K, E1C+L69R+Y220F, E1C+L69R+L227G, E1C+L69R+T231R, E1C+L69R+N233R, E1C+L69R+N233C, E1C+L69R+D254S, E1C+L69R+P256T, E1C+D96E+K98I, E1C+D96E+D111A, E1C+D96E+G163K, E1C+D96E+V176L, E1C+D96E+H198S, E1C+D96E+E210K, E1C+D96E+Y220F, E1C+D96E+L227G, E1C+D96E+T231R, E1C+D96E+N233R, E1C+D96E+N233C, E1C+D96E+D254S, E1C+D96E+P256T, E1C+K98I+D111A, E1C+K98I+G163K, E1C+K98I+V176L, E1C+K98I+H198S, E1C+K98I+E210K, E1C+K98I+Y220F, E1C+K98I+L227G, E1C+K98I+T231R, E1C+K98I+N233R, E1C+K98I+N233C, E1C+K98I+D254S, E1C+K98I+P256T, E1C+D111A+G163K, E1C+D111A+V176L, E1C+D111A+H198S, E1C+D111A+E210K, E1C+D111A+Y220F, E1C+D111A+L227G, E1C+D111A+T231R, E1C+D111A+N233R, E1C+D111A+N233C, E1C+D111A+D254S, E1C+D111A+P256T, E1C+G163K+V176L, E1C+G163K+H198S, E1C+G163K+E210K, E1C+G163K+Y220F, E1C+G163K+L227G, E1C+G163K+T231R, E1C+G163K+N233R, E1C+G163K+N233C, E1C+G163K+D254S, E1C+G163K+P256T, E1C+

V176L+H198S, E1C+V176L+E210K, E1C+V176L+Y220F, E1C+V176L+L227G, E1C+V176L+T231R, E1C+V176L+N233R, E1C+V176L+N233C, E1C+V176L+D254S, E1C+V176L+P256T, E1C+H198S+E210K, E1C+H198S+Y220F, E1C+H198S+L227G, E1C+H198S+T231R, E1C+H198S+N233R, E1C+H198S+N233C, E1C+H198S+D254S, E1C+H198S+P256T, E1C+E210K+Y220F, E1C+E210K+L227G, E1C+E210K+T231R, E1C+E210K+N233R, E1C+E210K+N233C, E1C+E210K+D254S, E1C+E210K+P256T, E1C+Y220F+L227G, E1C+Y220F+T231R, E1C+Y220F+N233R, E1C+Y220F+N233C, E1C+Y220F+D254S, E1C+Y220F+P256T, E1C+L227G+T231R, E1C+L227G+N233R, E1C+L227G+N233C, E1C+L227G+D254S, E1C+L227G+P256T, E1C+T231R+N233R, E1C+T231R+N233C, E1C+T231R+D254S, E1C+T231R+P256T, E1C+N233R+N233C, E1C+N233R+D254S, E1C+N233R+P256T, E1C+N233C+D254S, E1C+N233C+P256T, E1C+D254S+P256T, V2Y+D27R+N33K, V2Y+D27R+G38A, V2Y+D27R+F51V, V2Y+D27R+E56K, V2Y+D27R+L69R, V2Y+D27R+D96E, V2Y+D27R+K98I, V2Y+D27R+D111A, V2Y+D27R+G163K, V2Y+D27R+V176L, V2Y+D27R+H198S, V2Y+D27R+E210K, V2Y+D27R+Y220F, V2Y+D27R+L227G, V2Y+D27R+T231R, V2Y+D27R+N233R, V2Y+D27R+N233C, V2Y+D27R+D254S, V2Y+D27R+P256T, V2Y+N33K+G38A, V2Y+N33K+F51V, V2Y+N33K+E56K, V2Y+N33K+L69R, V2Y+N33K+D96E, V2Y+N33K+K98I, V2Y+N33K+D111A, V2Y+N33K+G163K, V2Y+N33K+V176L, V2Y+N33K+H198S, V2Y+N33K+E210K, V2Y+N33K+Y220F, V2Y+N33K+L227G, V2Y+N33K+T231R, V2Y+N33K+N233R, V2Y+N33K+N233C, V2Y+N33K+D254S, V2Y+N33K+P256T, V2Y+G38A+F51V, V2Y+G38A+E56K, V2Y+G38A+L69R, V2Y+G38A+D96E, V2Y+G38A+K98I, V2Y+G38A+D111A, V2Y+G38A+G163K, V2Y+G38A+V176L, V2Y+G38A+H198S, V2Y+G38A+E210K, V2Y+G38A+Y220F, V2Y+G38A+L227G, V2Y+G38A+T231R, V2Y+G38A+N233R, V2Y+G38A+N233C, V2Y+G38A+D254S, V2Y+G38A+P256T, V2Y+F51V+E56K, V2Y+F51V+L69R, V2Y+F51V+D96E, V2Y+F51V+K98I, V2Y+F51V+D111A, V2Y+F51V+G163K, V2Y+F51V+V176L, V2Y+F51V+H198S, V2Y+F51V+E210K, V2Y+F51V+Y220F, V2Y+F51V+L227G, V2Y+F51V+T231R, V2Y+F51V+N233R, V2Y+F51V+N233C, V2Y+F51V+D254S, V2Y+F51V+P256T, V2Y+E56K+L69R, V2Y+E56K+D96E, V2Y+E56K+K98I, V2Y+E56K+D111A, V2Y+E56K+G163K, V2Y+E56K+V176L, V2Y+E56K+H198S, V2Y+E56K+E210K, V2Y+E56K+Y220F, V2Y+E56K+L227G, V2Y+E56K+T231R, V2Y+E56K+N233R, V2Y+E56K+N233C, V2Y+E56K+D254S, V2Y+E56K+P256T, V2Y+L69R+D96E, V2Y+L69R+K98I, V2Y+L69R+D111A, V2Y+L69R+G163K, V2Y+L69R+V176L, V2Y+L69R+H198S, V2Y+L69R+E210K, V2Y+L69R+Y220F, V2Y+L69R+L227G, V2Y+L69R+T231R, V2Y+L69R+N233R, V2Y+L69R+N233C, V2Y+L69R+D254S, V2Y+L69R+P256T, V2Y+D96E+K98I, V2Y+D96E+D111A, V2Y+D96E+G163K, V2Y+D96E+V176L, V2Y+D96E+H198S, V2Y+D96E+E210K, V2Y+D96E+Y220F, V2Y+D96E+L227G, V2Y+D96E+T231R, V2Y+D96E+N233R, V2Y+D96E+N233C, V2Y+D96E+D254S, V2Y+D96E+P256T, V2Y+K98I+D111A, V2Y+K98I+G163K, V2Y+K98I+V176L, V2Y+K98I+H198S, V2Y+K98I+E210K, V2Y+K98I+Y220F, V2Y+K98I+L227G, V2Y+K98I+T231R, V2Y+K98I+N233R, V2Y+K98I+N233C, V2Y+K98I+D254S, V2Y+K98I+P256T, V2Y+D111A+G163K, V2Y+D111A+V176L, V2Y+D111A+H198S, V2Y+D111A+E210K, V2Y+D111A+Y220F, V2Y+D111A+L227G, V2Y+D111A+T231R, V2Y+D111A+N233R, V2Y+D111A+N233C, V2Y+D111A+D254S, V2Y+D111A+P256T, V2Y+G163K+V176L, V2Y+G163K+H198S, V2Y+G163K+E210K, V2Y+G163K+Y220F, V2Y+G163K+L227G, V2Y+G163K+T231R, V2Y+G163K+N233R, V2Y+G163K+N233C, V2Y+G163K+D254S, V2Y+G163K+P256T, V2Y+V176L+H198S, V2Y+V176L+E210K, V2Y+V176L+Y220F, V2Y+V176L+L227G, V2Y+V176L+T231R, V2Y+V176L+N233R, V2Y+V176L+N233C, V2Y+V176L+D254S, V2Y+V176L+P256T, V2Y+H198S+E210K, V2Y+H198S+Y220F, V2Y+H198S+L227G, V2Y+H198S+T231R, V2Y+H198S+N233R, V2Y+H198S+N233C, V2Y+H198S+D254S, V2Y+H198S+P256T, V2Y+E210K+Y220F, V2Y+E210K+L227G, V2Y+E210K+T231R, V2Y+E210K+N233R, V2Y+E210K+N233C, V2Y+E210K+D254S, V2Y+E210K+P256T, V2Y+Y220F+L227G, V2Y+Y220F+T231R, V2Y+Y220F+N233R, V2Y+Y220F+N233C, V2Y+Y220F+D254S, V2Y+Y220F+P256T, V2Y+L227G+T231R, V2Y+L227G+N233R, V2Y+L227G+N233C, V2Y+L227G+D254S, V2Y+L227G+P256T, V2Y+T231R+N233R, V2Y+T231R+N233C, V2Y+T231R+D254S, V2Y+T231R+P256T, V2Y+N233R+N233C, V2Y+N233R+D254S, V2Y+N233R+P256T, V2Y+N233C+D254S, V2Y+N233C+P256T, V2Y+D254S+P256T, D27R+N33K+G38A, D27R+N33K+F51V, D27R+N33K+E56K, D27R+N33K+L69R, D27R+N33K+D96E, D27R+N33K+K98I, D27R+N33K+D111A, D27R+N33K+G163K, D27R+N33K+V176L, D27R+N33K+H198S, D27R+N33K+E210K, D27R+N33K+Y220F, D27R+N33K+L227G, D27R+N33K+T231R, D27R+N33K+N233R, D27R+N33K+N233C, D27R+N33K+D254S, D27R+N33K+P256T, D27R+G38A+F51V, D27R+G38A+E56K, D27R+G38A+L69R, D27R+G38A+D96E, D27R+G38A+K98I, D27R+G38A+D111A, D27R+G38A+G163K, D27R+G38A+V176L, D27R+G38A+H198S, D27R+G38A+E210K, D27R+G38A+Y220F, D27R+G38A+L227G, D27R+G38A+T231R, D27R+G38A+N233R, D27R+G38A+N233C, D27R+G38A+D254S, D27R+G38A+P256T, D27R+F51V+E56K, D27R+F51V+L69R, D27R+F51V+D96E, D27R+F51V+K98I, D27R+F51V+D111A, D27R+F51V+G163K, D27R+F51V+V176L, D27R+F51V+H198S, D27R+F51V+E210K, D27R+F51V+Y220F, D27R+F51V+L227G, D27R+F51V+T231R, D27R+F51V+N233R, D27R+F51V+N233C, D27R+F51V+D254S, D27R+F51V+P256T, D27R+E56K+L69R, D27R+E56K+D96E, D27R+E56K+K98I, D27R+E56K+D111A, D27R+E56K+G163K, D27R+E56K+V176L, D27R+E56K+H198S, D27R+E56K+E210K, D27R+E56K+Y220F, D27R+E56K+L227G, D27R+E56K+T231R, D27R+E56K+N233R, D27R+E56K+N233C, D27R+E56K+D254S, D27R+E56K+P256T, D27R+L69R+D96E, D27R+L69R+K98I, D27R+L69R+D111A, D27R+L69R+G163K, D27R+L69R+V176L, D27R+L69R+H198S, D27R+L69R+E210K, D27R+L69R+Y220F, D27R+L69R+L227G, D27R+L69R+T231R, D27R+L69R+N233R, D27R+L69R+N233C, D27R+L69R+D254S, D27R+L69R+P256T, D27R+D96E+K98I, D27R+D96E+D111A, D27R+D96E+G163K, D27R+D96E+V176L, D27R+D96E+H198S, D27R+D96E+E210K, D27R+D96E+Y220F, D27R+D96E+L227G, D27R+D96E+T231R, D27R+D96E+N233R, D27R+D96E+N233C, D27R+D96E+D254S, D27R+D96E+P256T, D27R+K98I+D111A, D27R+K98I+G163K, D27R+K98I+V176L, D27R+K98I+H198S, D27R+K98I+E210K, D27R+K98I+Y220F, D27R+K98I+L227G, D27R+K98I+T231R, D27R+K98I+N233R, D27R+K98I+N233C, D27R+K98I+D254S, D27R+K98I+P256T, D27R+D111A+G163K, D27R+D111A+V176L, D27R+D111A+H198S, D27R+

D111A+E210K, D27R+D111A+Y220F, D27R+D111A+L227G, D27R+D111A+T231R, D27R+D111A+N233R, D27R+D111A+N233C, D27R+D111A+D254S, D27R+D111A+P256T, D27R+G163K+V176L, D27R+G163K+H198S, D27R+G163K+E210K, D27R+G163K+Y220F, D27R+G163K+L227G, D27R+G163K+T231R, D27R+G163K+N233R, D27R+G163K+N233C, D27R+G163K+D254S, D27R+G163K+P256T, D27R+V176L+H198S, D27R+V176L+E210K, D27R+V176L+Y220F, D27R+V176L+L227G, D27R+V176L+T231R, D27R+V176L+N233R, D27R+V176L+N233C, D27R+V176L+D254S, D27R+V176L+P256T, D27R+H198S+E210K, D27R+H198S+Y220F, D27R+H198S+L227G, D27R+H198S+T231R, D27R+H198S+N233R, D27R+H198S+N233C, D27R+H198S+D254S, D27R+H198S+P256T, D27R+E210K+Y220F, D27R+E210K+L227G, D27R+E210K+T231R, D27R+E210K+N233R, D27R+E210K+N233C, D27R+E210K+D254S, D27R+E210K+P256T, D27R+Y220F+L227G, D27R+Y220F+T231R, D27R+Y220F+N233R, D27R+Y220F+N233C, D27R+Y220F+D254S, D27R+Y220F+P256T, D27R+L227G+T231R, D27R+L227G+N233R, D27R+L227G+N233C, D27R+L227G+D254S, D27R+L227G+P256T, D27R+T231R+N233R, D27R+T231R+N233C, D27R+T231R+D254S, D27R+T231R+P256T, D27R+N233R+N233C, D27R+N233R+D254S, D27R+N233R+P256T, D27R+N233C+D254S, D27R+N233C+P256T, D27R+D254S+P256T, N33K+G38A+F51V, N33K+G38A+E56K, N33K+G38A+L69R, N33K+G38A+D96E, N33K+G38A+K98I, N33K+G38A+D111A, N33K+G38A+G163K, N33K+G38A+V176L, N33K+G38A+H198S, N33K+G38A+E210K, N33K+G38A+Y220F, N33K+G38A+L227G, N33K+G38A+T231R, N33K+G38A+N233R, N33K+G38A+N233C, N33K+G38A+D254S, N33K+G38A+P256T, N33K+F51V+E56K, N33K+F51V+L69R, N33K+F51V+D96E, N33K+F51V+K98I, N33K+F51V+D111A, N33K+F51V+G163K, N33K+F51V+V176L, N33K+F51V+H198S, N33K+F51V+E210K, N33K+F51V+Y220F, N33K+F51V+L227G, N33K+F51V+T231R, N33K+F51V+N233R, N33K+F51V+N233C, N33K+F51V+D254S, N33K+F51V+P256T, N33K+E56K+L69R, N33K+E56K+D96E, N33K+E56K+K98I, N33K+E56K+D111A, N33K+E56K+G163K, N33K+E56K+V176L, N33K+E56K+H198S, N33K+E56K+E210K, N33K+E56K+Y220F, N33K+E56K+L227G, N33K+E56K+T231R, N33K+E56K+N233R, N33K+E56K+N233C, N33K+E56K+D254S, N33K+E56K+P256T, N33K+L69R+D96E, N33K+L69R+K98I, N33K+L69R+D111A, N33K+L69R+G163K, N33K+L69R+V176L, N33K+L69R+H198S, N33K+L69R+E210K, N33K+L69R+Y220F, N33K+L69R+L227G, N33K+L69R+T231R, N33K+L69R+N233R, N33K+L69R+N233C, N33K+L69R+D254S, N33K+L69R+P256T, N33K+D96E+K98I, N33K+D96E+D111A, N33K+D96E+G163K, N33K+D96E+V176L, N33K+D96E+H198S, N33K+D96E+E210K, N33K+D96E+Y220F, N33K+D96E+L227G, N33K+D96E+T231R, N33K+D96E+N233R, N33K+D96E+N233C, N33K+D96E+D254S, N33K+D96E+P256T, N33K+K98I+D111A, N33K+K98I+G163K, N33K+K98I+V176L, N33K+K98I+H198S, N33K+K98I+E210K, N33K+K98I+Y220F, N33K+K98I+L227G, N33K+K98I+T231R, N33K+K98I+N233R, N33K+K98I+N233C, N33K+K98I+D254S, N33K+K98I+P256T, N33K+D111A+G163K, N33K+D111A+V176L, N33K+D111A+H198S, N33K+D111A+E210K, N33K+D111A+Y220F, N33K+D111A+L227G, N33K+D111A+T231R, N33K+D111A+N233R, N33K+D111A+N233C, N33K+D111A+D254S, N33K+D111A+P256T, N33K+G163K+V176L, N33K+G163K+H198S, N33K+G163K+E210K, N33K+G163K+Y220F, N33K+G163K+L227G, N33K+G163K+T231R, N33K+G163K+N233R, N33K+G163K+N233C, N33K+G163K+D254S, N33K+G163K+P256T, N33K+V176L+H198S, N33K+V176L+E210K, N33K+V176L+Y220F, N33K+V176L+L227G, N33K+V176L+T231R, N33K+V176L+N233R, N33K+V176L+N233C, N33K+V176L+D254S, N33K+V176L+P256T, N33K+H198S+E210K, N33K+H198S+Y220F, N33K+H198S+L227G, N33K+H198S+T231R, N33K+H198S+N233R, N33K+H198S+N233C, N33K+H198S+D254S, N33K+H198S+P256T, N33K+E210K+Y220F, N33K+E210K+L227G, N33K+E210K+T231R, N33K+E210K+N233R, N33K+E210K+N233C, N33K+E210K+D254S, N33K+E210K+P256T, N33K+Y220F+L227G, N33K+Y220F+T231R, N33K+Y220F+N233R, N33K+Y220F+N233C, N33K+Y220F+D254S, N33K+Y220F+P256T, N33K+L227G+T231R, N33K+L227G+N233R, N33K+L227G+N233C, N33K+L227G+D254S, N33K+L227G+P256T, N33K+T231R+N233R, N33K+T231R+N233C, N33K+T231R+D254S, N33K+T231R+P256T, N33K+N233R+N233C, N33K+N233R+D254S, N33K+N233R+P256T, N33K+N233C+D254S, N33K+N233C+P256T, N33K+D254S+P256T, G38A+F51V+E56K, G38A+F51V+L69R, G38A+F51V+D96E, G38A+F51V+K98I, G38A+F51V+D111A, G38A+F51V+G163K, G38A+F51V+V176L, G38A+F51V+H198S, G38A+F51V+E210K, G38A+F51V+Y220F, G38A+F51V+L227G, G38A+F51V+T231R, G38A+F51V+N233R, G38A+F51V+N233C, G38A+F51V+D254S, G38A+F51V+P256T, G38A+E56K+L69R, G38A+E56K+D96E, G38A+E56K+K98I, G38A+E56K+D111A, G38A+E56K+G163K, G38A+E56K+V176L, G38A+E56K+H198S, G38A+E56K+E210K, G38A+E56K+Y220F, G38A+E56K+L227G, G38A+E56K+T231R, G38A+E56K+N233R, G38A+E56K+N233C, G38A+E56K+D254S, G38A+E56K+P256T, G38A+L69R+D96E, G38A+L69R+K98I, G38A+L69R+D111A, G38A+L69R+G163K, G38A+L69R+V176L, G38A+L69R+H198S, G38A+L69R+E210K, G38A+L69R+Y220F, G38A+L69R+L227G, G38A+L69R+T231R, G38A+L69R+N233R, G38A+L69R+N233C, G38A+L69R+D254S, G38A+L69R+P256T, G38A+D96E+K98I, G38A+D96E+D111A, G38A+D96E+G163K, G38A+D96E+V176L, G38A+D96E+H198S, G38A+D96E+E210K, G38A+D96E+Y220F, G38A+D96E+L227G, G38A+D96E+T231R, G38A+D96E+N233R, G38A+D96E+N233C, G38A+D96E+D254S, G38A+D96E+P256T, G38A+K98I+D111A, G38A+K98I+G163K, G38A+K98I+V176L, G38A+K98I+H198S, G38A+K98I+E210K, G38A+K98I+Y220F, G38A+K98I+L227G, G38A+K98I+T231R, G38A+K98I+N233R, G38A+K98I+N233C, G38A+K98I+D254S, G38A+K98I+P256T, G38A+D111A+G163K, G38A+D111A+V176L, G38A+D111A+H198S, G38A+D111A+E210K, G38A+D111A+Y220F, G38A+D111A+L227G, G38A+D111A+T231R, G38A+D111A+N233R, G38A+D111A+N233C, G38A+D111A+D254S, G38A+D111A+P256T, G38A+G163K+V176L, G38A+G163K+H198S, G38A+G163K+E210K, G38A+G163K+Y220F, G38A+G163K+L227G, G38A+G163K+T231R, G38A+G163K+N233R, G38A+G163K+N233C, G38A+G163K+D254S, G38A+G163K+P256T, G38A+V176L+H198S, G38A+V176L+E210K, G38A+V176L+Y220F, G38A+V176L+L227G, G38A+V176L+T231R, G38A+V176L+N233R, G38A+V176L+N233C, G38A+V176L+D254S, G38A+V176L+P256T, G38A+H198S+E210K, G38A+H198S+Y220F, G38A+H198S+L227G, G38A+H198S+T231R, G38A+H198S+N233R, G38A+H198S+

N233C, G38A+H198S+D254S, G38A+H198S+P256T, G38A+E210K+Y220F, G38A+E210K+L227G, G38A+E210K+T231R, G38A+E210K+N233R, G38A+E210K+N233C, G38A+E210K+D254S, G38A+E210K+P256T, G38A+Y220F+L227G, G38A+Y220F+T231R, G38A+Y220F+N233R, G38A+Y220F+N233C, G38A+Y220F+D254S, G38A+Y220F+P256T, G38A+L227G+T231R, G38A+L227G+N233R, G38A+L227G+N233C, G38A+L227G+D254S, G38A+L227G+P256T, G38A+T231R+N233R, G38A+T231R+N233C, G38A+T231R+D254S, G38A+T231R+P256T, G38A+N233R+N233C, G38A+N233R+D254S, G38A+N233R+P256T, G38A+N233C+D254S, G38A+N233C+P256T, G38A+D254S+P256T, F51V+E56K+L69R, F51V+E56K+D96E, F51V+E56K+K98I, F51V+E56K+D111A, F51V+E56K+G163K, F51V+E56K+V176L, F51V+E56K+H198S, F51V+E56K+E210K, F51V+E56K+Y220F, F51V+E56K+L227G, F51V+E56K+T231R, F51V+E56K+N233R, F51V+E56K+N233C, F51V+E56K+D254S, F51V+E56K+P256T, F51V+L69R+D96E, F51V+L69R+K98I, F51V+L69R+D111A, F51V+L69R+G163K, F51V+L69R+V176L, F51V+L69R+H198S, F51V+L69R+E210K, F51V+L69R+Y220F, F51V+L69R+L227G, F51V+L69R+T231R, F51V+L69R+N233R, F51V+L69R+N233C, F51V+L69R+D254S, F51V+L69R+P256T, F51V+D96E+K98I, F51V+D96E+D111A, F51V+D96E+G163K, F51V+D96E+V176L, F51V+D96E+H198S, F51V+D96E+E210K, F51V+D96E+Y220F, F51V+D96E+L227G, F51V+D96E+T231R, F51V+D96E+N233R, F51V+D96E+N233C, F51V+D96E+D254S, F51V+D96E+P256T, F51V+K98I+D111A, F51V+K98I+G163K, F51V+K98I+V176L, F51V+K98I+H198S, F51V+K98I+E210K, F51V+K98I+Y220F, F51V+K98I+L227G, F51V+K98I+T231R, F51V+K98I+N233R, F51V+K98I+N233C, F51V+K98I+D254S, F51V+K98I+P256T, F51V+D111A+G163K, F51V+D111A+V176L, F51V+D111A+H198S, F51V+D111A+E210K, F51V+D111A+Y220F, F51V+D111A+L227G, F51V+D111A+T231R, F51V+D111A+N233R, F51V+D111A+N233C, F51V+D111A+D254S, F51V+D111A+P256T, F51V+G163K+V176L, F51V+G163K+H198S, F51V+G163K+E210K, F51V+G163K+Y220F, F51V+G163K+L227G, F51V+G163K+T231R, F51V+G163K+N233R, F51V+G163K+N233C, F51V+G163K+D254S, F51V+G163K+P256T, F51V+V176L+H198S, F51V+V176L+E210K, F51V+V176L+Y220F, F51V+V176L+L227G, F51V+V176L+T231R, F51V+V176L+N233R, F51V+V176L+N233C, F51V+V176L+D254S, F51V+V176L+P256T, F51V+H198S+E210K, F51V+H198S+Y220F, F51V+H198S+L227G, F51V+H198S+T231R, F51V+H198S+N233R, F51V+H198S+N233C, F51V+H198S+D254S, F51V+H198S+P256T, F51V+E210K+Y220F, F51V+E210K+L227G, F51V+E210K+T231R, F51V+E210K+N233R, F51V+E210K+N233C, F51V+E210K+D254S, F51V+E210K+P256T, F51V+Y220F+L227G, F51V+Y220F+T231R, F51V+Y220F+N233R, F51V+Y220F+N233C, F51V+Y220F+D254S, F51V+Y220F+P256T, F51V+L227G+T231R, F51V+L227G+N233R, F51V+L227G+N233C, F51V+L227G+D254S, F51V+L227G+P256T, F51V+T231R+N233R, F51V+T231R+N233C, F51V+T231R+D254S, F51V+T231R+P256T, F51V+N233R+N233C, F51V+N233R+D254S, F51V+N233R+P256T, F51V+N233C+D254S, F51V+N233C+P256T, F51V+D254S+P256T, E56K+L69R+D96E, E56K+L69R+K98I, E56K+L69R+D111A, E56K+L69R+G163K, E56K+L69R+V176L, E56K+L69R+H198S, E56K+L69R+E210K, E56K+L69R+Y220F, E56K+L69R+L227G, E56K+L69R+T231R, E56K+L69R+N233R, E56K+L69R+N233C, E56K+L69R+D254S, E56K+L69R+

P256T, E56K+D96E+K98I, E56K+D96E+D111A, E56K+D96E+G163K, E56K+D96E+V176L, E56K+D96E+H198S, E56K+D96E+E210K, E56K+D96E+Y220F, E56K+D96E+L227G, E56K+D96E+T231R, E56K+D96E+N233R, E56K+D96E+N233C, E56K+D96E+D254S, E56K+D96E+P256T, E56K+K98I+D111A, E56K+K98I+G163K, E56K+K98I+V176L, E56K+K98I+H198S, E56K+K98I+E210K, E56K+K98I+Y220F, E56K+K98I+L227G, E56K+K98I+T231R, E56K+K98I+N233R, E56K+K98I+N233C, E56K+K98I+D254S, E56K+K98I+P256T, E56K+D111A+G163K, E56K+D111A+V176L, E56K+D111A+H198S, E56K+D111A+E210K, E56K+D111A+Y220F, E56K+D111A+L227G, E56K+D111A+T231R, E56K+D111A+N233R, E56K+D111A+N233C, E56K+D111A+D254S, E56K+D111A+P256T, E56K+G163K+V176L, E56K+G163K+H198S, E56K+G163K+E210K, E56K+G163K+Y220F, E56K+G163K+L227G, E56K+G163K+T231R, E56K+G163K+N233R, E56K+G163K+N233C, E56K+G163K+D254S, E56K+G163K+P256T, E56K+V176L+H198S, E56K+V176L+E210K, E56K+V176L+Y220F, E56K+V176L+L227G, E56K+V176L+T231R, E56K+V176L+N233R, E56K+V176L+N233C, E56K+V176L+D254S, E56K+V176L+P256T, E56K+H198S+E210K, E56K+H198S+Y220F, E56K+H198S+L227G, E56K+H198S+T231R, E56K+H198S+N233R, E56K+H198S+N233C, E56K+H198S+D254S, E56K+H198S+P256T, E56K+E210K+Y220F, E56K+E210K+L227G, E56K+E210K+T231R, E56K+E210K+N233R, E56K+E210K+N233C, E56K+E210K+D254S, E56K+E210K+P256T, E56K+Y220F+L227G, E56K+Y220F+T231R, E56K+Y220F+N233R, E56K+Y220F+N233C, E56K+Y220F+D254S, E56K+Y220F+P256T, E56K+L227G+T231R, E56K+L227G+N233R, E56K+L227G+N233C, E56K+L227G+D254S, E56K+L227G+P256T, E56K+T231R+N233R, E56K+T231R+N233C, E56K+T231R+D254S, E56K+T231R+P256T, E56K+N233R+N233C, E56K+N233R+D254S, E56K+N233R+P256T, E56K+N233C+D254S, E56K+N233C+P256T, E56K+D254S+P256T, L69R+D96E+K98I, L69R+D96E+D111A, L69R+D96E+G163K, L69R+D96E+V176L, L69R+D96E+H198S, L69R+D96E+E210K, L69R+D96E+Y220F, L69R+D96E+L227G, L69R+D96E+T231R, L69R+D96E+N233R, L69R+D96E+N233C, L69R+D96E+D254S, L69R+D96E+P256T, L69R+K98I+D111A, L69R+K98I+G163K, L69R+K98I+V176L, L69R+K98I+H198S, L69R+K98I+E210K, L69R+K98I+Y220F, L69R+K98I+L227G, L69R+K98I+T231R, L69R+K98I+N233R, L69R+K98I+N233C, L69R+K98I+D254S, L69R+K98I+P256T, L69R+D111A+G163K, L69R+D111A+V176L, L69R+D111A+H198S, L69R+D111A+E210K, L69R+D111A+Y220F, L69R+D111A+L227G, L69R+D111A+T231R, L69R+D111A+N233R, L69R+D111A+N233C, L69R+D111A+D254S, L69R+D111A+P256T, L69R+G163K+V176L, L69R+G163K+H198S, L69R+G163K+E210K, L69R+G163K+Y220F, L69R+G163K+L227G, L69R+G163K+T231R, L69R+G163K+N233R, L69R+G163K+N233C, L69R+G163K+D254S, L69R+G163K+P256T, L69R+V176L+H198S, L69R+V176L+E210K, L69R+V176L+Y220F, L69R+V176L+L227G, L69R+V176L+T231R, L69R+V176L+N233R, L69R+V176L+N233C, L69R+V176L+D254S, L69R+V176L+P256T, L69R+H198S+E210K, L69R+H198S+Y220F, L69R+H198S+L227G, L69R+H198S+T231R, L69R+H198S+N233R, L69R+H198S+N233C, L69R+H198S+D254S, L69R+H198S+P256T, L69R+E210K+Y220F, L69R+E210K+L227G, L69R+E210K+T231R, L69R+E210K+N233R, L69R+E210K+N233C, L69R+E210K+D254S, L69R+E210K+P256T, L69R+

Y220F+L227G, L69R+Y220F+T231R, L69R+Y220F+N233R, L69R+Y220F+N233C, L69R+Y220F+D254S, L69R+Y220F+P256T, L69R+L227G+T231R, L69R+L227G+N233R, L69R+L227G+N233C, L69R+L227G+D254S, L69R+L227G+P256T, L69R+T231R+N233R, L69R+T231R+N233C, L69R+T231R+D254S, L69R+T231R+P256T, L69R+N233R+N233C, L69R+N233R+D254S, L69R+N233R+P256T, L69R+N233C+D254S, L69R+N233C+P256T, L69R+D254S+P256T, D96E+K98I+D111A, 96E+K98I+G163K, D96E+K98I+V176L, D96E+K98I+H198S, D96E+K98I+E210K, D96E+K98I+Y220F, D96E+K98I+L227G, D96E+K98I+T231R, D96E+K98I+N233R, D96E+K98I+N233C, D96E+K98I+D254S, D96E+K98I+P256T, D96E+D111A+G163K, D96E+D111A+V176L, D96E+D111A+H198S, D96E+D111A+E210K, D96E+D111A+Y220F, D96E+D111A+L227G, D96E+D111A+T231R, D96E+D111A+N233R, D96E+D111A+N233C, D96E+D111A+D254S, D96E+D111A+P256T, D96E+G163K+V176L, D96E+G163K+H198S, D96E+G163K+E210K, D96E+G163K+Y220F, D96E+G163K+L227G, D96E+G163K+T231R, D96E+G163K+N233R, D96E+G163K+N233C, D96E+G163K+D254S, D96E+G163K+P256T, D96E+V176L+H198S, D96E+V176L+E210K, D96E+V176L+Y220F, D96E+V176L+L227G, D96E+V176L+T231R, D96E+V176L+N233R, D96E+V176L+N233C, D96E+V176L+D254S, D96E+V176L+P256T, D96E+H198S+E210K, D96E+H198S+Y220F, D96E+H198S+L227G, D96E+H198S+T231R, D96E+H198S+N233R, D96E+H198S+N233C, D96E+H198S+D254S, D96E+H198S+P256T, D96E+E210K+Y220F, D96E+E210K+L227G, D96E+E210K+T231R, D96E+E210K+N233R, D96E+E210K+N233C, D96E+E210K+D254S, D96E+E210K+P256T, D96E+Y220F+L227G, D96E+Y220F+T231R, D96E+Y220F+N233R, D96E+Y220F+N233C, D96E+Y220F+D254S, D96E+Y220F+P256T, D96E+L227G+T231R, D96E+L227G+N233R, D96E+L227G+N233C, D96E+L227G+D254S, D96E+L227G+P256T, D96E+T231R+N233R, D96E+T231R+N233C, D96E+T231R+D254S, D96E+T231R+P256T, D96E+N233R+N233C, D96E+N233R+D254S, D96E+N233R+P256T, D96E+N233C+D254S, D96E+N233C+P256T, D96E+D254S+P256T, K98I+D111A+G163K, K98I+D111A+V176L, K98I+D111A+H198S, K98I+D111A+E210K, K98I+D111A+Y220F, K98I+D111A+L227G, K98I+D111A+T231R, K98I+D111A+N233R, K98I+D111A+N233C, K98I+D111A+D254S, K98I+D111A+P256T, K98I+G163K+V176L, K98I+G163K+H198S, K98I+G163K+E210K, K98I+G163K+Y220F, K98I+G163K+L227G, K98I+G163K+T231R, K98I+G163K+N233R, K98I+G163K+N233C, K98I+G163K+D254S, K98I+G163K+P256T, K98I+V176L+H198S, K98I+V176L+E210K, K98I+V176L+Y220F, K98I+V176L+L227G, K98I+V176L+T231R, K98I+V176L+N233R, K98I+V176L+N233C, K98I+V176L+D254S, K98I+V176L+P256T, K98I+H198S+E210K, K98I+H198S+Y220F, K98I+H198S+L227G, K98I+H198S+T231R, K98I+H198S+N233R, K98I+H198S+N233C, K98I+H198S+D254S, K98I+H198S+P256T, K98I+E210K+Y220F, K98I+E210K+L227G, K98I+E210K+T231R, K98I+E210K+N233R, K98I+E210K+N233C, K98I+E210K+D254S, K98I+E210K+P256T, K98I+Y220F+L227G, K98I+Y220F+T231R, K98I+Y220F+N233R, K98I+Y220F+N233C, K98I+Y220F+D254S, K98I+Y220F+P256T, K98I+L227G+T231R, K98I+L227G+N233R, K98I+L227G+N233C, K98I+L227G+D254S, K98I+L227G+P256T, K98I+T231R+N233R, K98I+T231R+N233C, K98I+T231R+D254S, K98I+T231R+P256T, K98I+N233R+N233C, K98I+N233R+D254S, K98I+N233R+P256T, K98I+N233C+D254S, K98I+N233C+P256T, K98I+D254S+P256T, D111A+G163K+V176L, D111A+G163K+H198S, D111A+G163K+E210K, D111A+G163K+Y220F, D111A+G163K+L227G, D111A+G163K+T231R, D111A+G163K+N233R, D111A+G163K+N233C, D111A+G163K+D254S, D111A+G163K+P256T, D111A+V176L+H198S, D111A+V176L+E210K, D111A+V176L+Y220F, D111A+V176L+L227G, D111A+V176L+T231R, D111A+V176L+N233R, D111A+V176L+N233C, D111A+V176L+D254S, D111A+V176L+P256T, D111A+H198S+E210K, D111A+H198S+Y220F, D111A+H198S+L227G, D111A+H198S+T231R, D111A+H198S+N233R, D111A+H198S+N233C, D111A+H198S+D254S, D111A+H198S+P256T, D111A+E210K+Y220F, D111A+E210K+L227G, D111A+E210K+T231R, D111A+E210K+N233R, D111A+E210K+N233C, D111A+E210K+D254S, D111A+E210K+P256T, D111A+Y220F+L227G, D111A+Y220F+T231R, D111A+Y220F+N233R, D111A+Y220F+N233C, D111A+Y220F+D254S, D111A+Y220F+P256T, D111A+L227G+T231R, D111A+L227G+N233R, D111A+L227G+N233C, D111A+L227G+D254S, D111A+L227G+P256T, D111A+T231R+N233R, D111A+T231R+N233C, D111A+T231R+D254S, D111A+T231R+P256T, D111A+N233R+N233C, D111A+N233R+D254S, D111A+N233R+P256T, D111A+N233C+D254S, D111A+N233C+P256T, D111A+D254S+P256T, G163K+V176L+H198S, G163K+V176L+E210K, G163K+V176L+Y220F, G163K+V176L+L227G, G163K+V176L+T231R, G163K+V176L+N233R, G163K+V176L+N233C, G163K+V176L+D254S, G163K+V176L+P256T, G163K+H198S+E210K, G163K+H198S+Y220F, G163K+H198S+L227G, G163K+H198S+T231R, G163K+H198S+N233R, G163K+H198S+N233C, G163K+H198S+D254S, G163K+H198S+P256T, G163K+E210K+Y220F, G163K+E210K+L227G, G163K+E210K+T231R, G163K+E210K+N233R, G163K+E210K+N233C, G163K+E210K+D254S, G163K+E210K+P256T, G163K+Y220F+L227G, G163K+Y220F+T231R, G163K+Y220F+N233R, G163K+Y220F+N233C, G163K+Y220F+D254S, G163K+Y220F+P256T, G163K+L227G+T231R, G163K+L227G+N233R, G163K+L227G+N233C, G163K+L227G+D254S, G163K+L227G+P256T, G163K+T231R+N233R, G163K+T231R+N233C, G163K+T231R+D254S, G163K+T231R+P256T, G163K+N233R+N233C, G163K+N233R+D254S, G163K+N233R+P256T, G163K+N233C+D254S, G163K+N233C+P256T, G163K+D254S+P256T, V176L+H198S+E210K, V176L+H198S+Y220F, V176L+H198S+L227G, V176L+H198S+T231R, V176L+H198S+N233R, V176L+H198S+N233C, V176L+H198S+D254S, V176L+H198S+P256T, V176L+E210K+Y220F, V176L+E210K+L227G, V176L+E210K+T231R, V176L+E210K+N233R, V176L+E210K+N233C, V176L+E210K+D254S, V176L+E210K+P256T, V176L+Y220F+L227G, V176L+Y220F+T231R, V176L+Y220F+N233R, V176L+Y220F+N233C, V176L+Y220F+D254S, V176L+Y220F+P256T, V176L+L227G+T231R, V176L+L227G+N233R, V176L+L227G+N233C, V176L+L227G+D254S, V176L+L227G+P256T, V176L+T231R+N233R, V176L+T231R+N233C, V176L+T231R+D254S, V176L+T231R+P256T, V176L+N233R+N233C, V176L+N233R+D254S, V176L+N233R+P256T, V176L+N233C+D254S, V176L+N233C+P256T, V176L+D254S+P256T, H198S+E210K+Y220F, H198S+E210K+L227G, H198S+E210K+T231R, H198S+E210K+N233R, H198S+E210K+N233C, H198S+E210K+D254S, H198S+E210K+P256T, H198S+Y220F+L227G, H198S+Y220F+T231R, H198S+Y220F+N233R, H198S+Y220F+N233C, H198S+Y220F+D254S, H198S+Y220F+P256T, H198S+L227G+

T231R, H198S+L227G+N233R, H198S+L227G+N233C, H198S+L227G+D254S, H198S+L227G+P256T, H198S+T231R+N233R, H198S+T231R+N233C, H198S+T231R+D254S, H198S+T231R+P256T, H198S+N233R+N233C, H198S+N233R+D254S, H198S+N233R+P256T, H198S+N233C+D254S, H198S+N233C+P256T, H198S+D254S+P256T, E210K+Y220F+L227G, E210K+Y220F+T231R, E210K+Y220F+N233R, E210K+Y220F+N233C, E210K+Y220F+D254S, E210K+Y220F+P256T, E210K+L227G+T231R, E210K+L227G+N233R, E210K+L227G+N233C, E210K+L227G+D254S, E210K+L227G+P256T, E210K+T231R+N233R, E210K+T231R+N233C, E210K+T231R+D254S, E210K+T231R+P256T, E210K+N233R+N233C, E210K+N233R+D254S, E210K+N233R+P256T, E210K+N233C+D254S, E210K+N233C+P256T, E210K+D254S+P256T, Y220F+L227G+T231R, Y220F+L227G+N233R, Y220F+L227G+N233C, Y220F+L227G+D254S, Y220F+L227G+P256T, Y220F+T231R+N233R, Y220F+T231R+N233C, Y220F+T231R+D254S, Y220F+T231R+P256T, Y220F+N233R+N233C, Y220F+N233R+D254S, Y220F+N233R+P256T, Y220F+N233C+D254S, Y220F+N233C+P256T, Y220F+D254S+P256T, L227G+T231R+N233R, L227G+T231R+N233C, L227G+T231R+D254S, L227G+T231R+P256T, L227G+N233R+N233C, L227G+N233R+D254S, L227G+N233R+P256T, L227G+N233C+D254S, L227G+N233C+P256T, L227G+D254S+P256T, T231R+N233R+N233C, T231R+N233R+D254S, T231R+N233R+P256T, T231R+N233C+D254S, T231R+N233C+P256T, T231R+D254S+P256T, N233R+N233C+D254S, N233R+N233C+P256T, N233R+D254S+P256T, and N233C+D254S+P256T, wherein numbering is according to SEQ ID NO: 1.

In a preferred embodiment the lipase variant of the invention comprises one of the following set of substitutions using SEQ ID NO: 1 for numbering:

| |
|---|
| E1C + H198L + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + H198Y + N233C |
| E1C + H198T + N233C |
| E1C + H198G + N233C |
| E1C + L227F + N233C |
| E1C + L227R + N233C |
| E1C + E210T + N233C |
| E1C + E210N + N233C |
| E1C + V176M + N233C |
| E1C + K98T + N233C |
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |
| E1C + V2I + N233C |
| E1C + V2N + N233C |
| E1C + V2K + N233C |
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + T231R + N233C |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + E210A + N233C |
| E1C + E210Q + N233C |
| E1C + E210R + N233C |
| E1C + H198D + N233C |
| E1C + K98R + N233C |
| E1C + K98V + N233C |
| E1C + F51L + N233C |
| E1C + F51I + N233C |
| E1C + K237C |
| E1C + L227G + N233C |
| E1C + E210K + N233C |
| E1C + V176L + N233C |
| E1C + K98Q + N233C |
| E1C + E56K + N233C |
| E1C + L147S + N233C + D254S |
| E1C + Y220F + N233C |
| E1C + K98I + N233C |
| E1C + N233C |
| E1C + D27R + F51I + E56R + K98E + T231R + N233C |

-continued

| |
|---|
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + F51L + D96E + K98I + D111A + G163S + H198S + Y220F + T231R + N233C + P256T |
| E1C + D27R + F51L + D96E + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + P256T |
| E1C + D27R + F51V + D96E + K98I + D111A + G163K + H198S + Y220F + T231R + N233C + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96E + K98I + D111A + G163S + H198S + Y220F + T231R + N233C + P256T |
| E1C + F51L + D96E + K98I + D111A + G163K + H198S + Y220F + T231R + N233C + D254S + P256T |
| E1C + G38A + F51V + D96E + K98I + D111A + G163K + H198S + Y220F + T231R + N233C + P256T |
| E1C + F51V + D96E + K98I + D111A + G163K + H198S + Y220F + T231R + N233C + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + D27R + N33K + G38A + F51V + D96E + K98I + D111A + G163K + H198S + Y220F + T231R + N233C |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

In one embodiment, the lipase variant further comprises one of the substitutions selected from the group of: S54T, S83T, G91A, A150G, I255A, and E239C.

In one embodiment, the parent lipase is a lipase having at least 70%, such as at least 75%, such as at least 80%, such as at least 85%, such as at least 90%, such as at least 95%, such as at least 96% such as at least 97%, such as at least 98%, such as at least 99%, such as 100% sequence identity to the amino acid sequence of SEQ ID NO: 1.

In one embodiment, the parent lipase comprises an amino acid sequence of at least 70%, such as at least 75%, such as at least 80%, such as at least 85%, such as at least 90%, such as at least 95%, such as at least 96%, such as at least 97%, such as at least 98%, such as at least 99%, such as 100% sequence identity to the amino acid sequence of SEQ ID NO: 1.

In one embodiment, the parent lipase comprises or consists of the amino acid sequence of SEQ ID NO: 1. In an embodiment the parent lipase comprises or consists of the amino acids of SEQ ID NO: 1 with the following substitutions: E1C+N233C.

Compositions of the Invention

In one aspect, the present invention relates to a composition comprising (i) at least one surfactant and (ii) a lipase variant of a parent lipase, wherein said variant (a) comprises a modification in at least one position corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1;
(b) has a sequence identity of at least 75% but less than 100% to SEQ ID NO: 1;
(c) has lipase activity; and
(d) has an improved activity as compared to the parent lipase.

The term "composition" as used herein, refers to any kind of composition suitable for use in removing a stain from a fabric, hard surface or similar materials. In some embodiment, the composition may be a detergent composition, a pre-treatment composition, a soaking composition or a boosting composition. It is within the knowledge of the skilled person to determine when a composition may be considered as a detergent composition. The term "pre-treatment composition" as used herein, refers to a composition for use in particular before laundering a fabric, wherein the pre-treatment composition is applied to the fabric and left for a certain period of time before laundering the fabric. The term "soaking composition" as used herein, refers to a composition for use in particular before laundering a fabric, wherein the fabric is left in a solution of water and the soaking composition for a certain period of time before laundering the fabric. The soaking composition may also be used to soak a hard surface, such as kitchen ware or the like, before dishwashing. The term "boosting composition" as used herein, refers to a composition used as an additive, as an aid for a detergent composition, such as a laundry detergent composition, wherein the boosting composition has a beneficial effect on the stains to be removed. In particular, it may be a boosting composition used to lift the stain from a fabric if it is a laundering process, or from a hard surface if is a dishwashing process.

The term "lipase variant" has the same meaning and purpose as defined elsewhere herein.

Thus, the invention relates to a composition comprising (i) at least one surfactant and (ii) a lipase variant of a parent lipase, wherein said variant (a) comprises a modification in at least one position corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1;
(b) has a sequence identity of at least 75% but less than 100% to SEQ ID NO: 1;
(c) has lipase activity; and has an improved activity as compared to the parent lipase.

It is to be understood that in the context of the present invention “a lipase variant” or “the lipase variant” means “at least one lipase variant” unless contradicted by context, e.g. “the one lipase variant”. Thus, the composition according to the invention will in all embodiments comprise at least one lipase variant. The same applies to the protease or the alpha-amylase or any variant thereof.

It is believed that combining at least one surfactant and a lipase in a composition may improve the overall performance of the composition. Further, the concentration of surfactant may even be lowered when combined with a lipase variant as described herein, and the same effect, such as performance, is obtained.

In one embodiment, the concentration of the surfactant is at least 3 wt %, such as at least 4 wt %, such as at least 5 wt %, such as at least 6 wt %, such as at least 7 wt %, such as at least 8 wt %, of the composition. It is to be understood that the concentration of the surfactant in the composition may be the same, but once the composition is used in e.g. a laundry process, the concentration of the surfactant is changed and may change during the wash cycle. Preferably, the concentration of the surfactant or mixture of surfactants in e.g. a laundry process should be present in the main wash at concentrations above the critical micelle concentration, meaning that the surfactants are mainly found in micellar form in the main wash. The critical micelle concentration may be affected by formation of fatty acids, mono- and di-glycerides from the activity of the lipase variant of the composition.

In one embodiment, the at least one surfactant comprises an anionic surfactant, such as linear alkylbenzene sulfonate (LAS) or alcohol ether sulfate (AEOS).

In one embodiment the composition comprises the anionic surfactant alcohol ether sulfate (AEOS). In another embodiment the composition comprises one or more non-ionic surfactant, such as AEO.

In one embodiment, the at least one surfactant is a mix of two or more surfactants. The surfactant of the present invention may preferably be a combination of two or more surfactants, such as a mixture of surfactants. By combining surfactants and a lipase variant as herein described an improved effect of the composition may be obtained.

In a particular embodiment, the at least one surfactant is a mix of a first surfactant and a second surfactant.

In a particular embodiment, the first surfactant is a first anionic surfactant and the second surfactant is a second anionic surfactant.

In another particular embodiment, the first surfactant is an anionic surfactant and the second surfactant is a non-ionic surfactant.

In a particular embodiment, the anionic surfactant is linear alkylbenzene sulfonate (LAS) or AEOS, and said non-ionic surfactant is alcohol ethoxylate (AEO). The abbreviations AEOS and AES refer to alcohol ether sulfates, which are also known as alcohol ethoxy sulfates or fatty alcohol ether sulfates.

In one embodiment, the concentration of the anionic surfactant is between 2 wt % and 14 wt % of the composition, such as between 3 wt % and 13 wt %, such as between 5 wt % and 12 wt % of the composition, and the concentration of the non-ionic surfactant is between 5 wt % and 13 wt %, such as 6 wt % and 12 wt %. In a preferred embodiment, the concentration of linear alkylbenzene sulfonate (LAS) is between 7 wt % and 12 wt %, alcohol ether sulfate (AEOS) between 3 wt % and 7 wt %, and alcohol ethoxylate (AEO) between 6 wt % and 11 wt %.

In one embodiment, the first surfactant and the second surfactant is present in the composition in a ratio of 3:1, 2:1, 1:1. In an embodiment the ratio between the first and second surfactant may be in the range from 10:1 to 1:10, such as 5:1 to 1:5, or 3:1 to 1:3. In a preferred embodiment, the ratio of the first surfactant and the second surfactant is 2:1. The term “ratio of the first surfactant and the second surfactant” as used herein, refers to the amounts or concentrations of the two surfactants in the composition. Thus, when the ratio is defined, e.g. 2:1, it in means that the first surfactant is present in an amount or concentration twice the amount or concentration of the second surfactant. Thus, more specifically, the first surfactant may be present in a concentration of 10 wt %, then the second surfactant is present in a concentration of 5 wt % if the ratio of the two surfactants is 2:1.

The composition according to the invention also comprises a lipase variant of a parent lipase. The lipase variant herein described has an improved activity as compared to the parent lipase and optionally an improved odor reduction as compared to the parent lipase. In certain embodiments, the lipase variant further has an improved stability. Accordingly, the lipase variant comprises at least one modification in the positions corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1.

The lipase variant of the composition according to the invention has at least 75%, such as at least 75%, such as at least 80%, such as at least 85%, such as at least 90%, such as at least 95%, such as at least 97%, such as at least 99% but less than 100% sequence identity to the amino acid sequence of SEQ ID NO: 1. Accordingly, in one embodiment, the lipase variant has at least 75%, such as at least 75%, such as at least 80%, such as at least 85%, such as at least 90%, such as at least 95%, such as at least 97%, such as at least 99% but less than 100% sequence identity to the amino acid sequence of SEQ ID NO: 1.

In one embodiment, the lipase variant comprises a modification in two positions selected from the positions corresponding to E1, V2, N33, F51, E56, L69, K98, V176, H198, E210, Y220, and L227 of SEQ ID NO: 1. Thus, in a particular embodiment, the lipase variant comprises a modification in two positions selected from the group consisting of; E1+V2, E1+N33, E1+F51, E1+E56, E1+L69, E1+K98, E1+V176, E1+H198, E1+E210, E1+Y220, E1+L227, V2+N33, V2+F51, V2+E56, V2+L69, V2+K98, V2+V176, V2+H198, V2+E210, V2+Y220, V2+L227, N33+F51, N33+E56, N33+L69, N33+K98, N33+V176, N33+H198, N33+E210, N33+Y220, N33+L227, F51+E56, F51+L69, F51+K98, F51+V176, F51+H198, F51+E210, F51+Y220, F51+L227, E56+L69, E56+K98, E56+V176, E56+H198, E56+E210, E56+Y220, E56+L227, L69+K98, L69+V176, L69+H198, L69+E210, L69+Y220, L69+L227, K98+V176, K98+H198, K98+E210, K98+Y220, K98+L227, V176+H198, V176+E210, V176+Y220, V176+L227, H198+E210, H198+Y220, H198+L227, E210+Y220, E210+L227, and Y220+L227, wherein numbering is according to SEQ ID NO: 1.

In a particular embodiment, the lipase variant comprises a modification in two positions selected from the positions corresponding to positions E1, V2, D27, N33, G38, F51, E56, L69, D96, K98, D111, G163, V176, H198, E210, Y220, L227, T231, N233, N233, D254, and P256, wherein numbering is according to SEQ ID NO: 1. Thus, in a particular embodiment, the lipase variant comprises a modification in two positions selected from the group consisting of: E1+V2, E1+D27, E1+N33, E1+G38, E1+F51, E1+E56, E1+L69, E1+D96, E1+K98, E1+D111, E1+G163, E1+V176, E1+H198, E1+E210, E1+Y220, E1+L227, E1+T231, E1+N233, E1+D254, E1+P256, V2+D27, V2+N33, V2+G38, V2+F51, V2+E56, V2+L69, V2+D96, V2+K98, V2+D111, V2+G163, V2+V176, V2+H198, V2+E210, V2+Y220, V2+L227, V2+T231, V2+N233, V2+D254, V2+P256, D27+N33, D27+G38, D27+F51, D27+E56, D27+L69, D27+D96, D27+K98, D27+D111, D27+G163, D27+V176, D27+H198, D27+E210, D27+Y220, D27+L227, D27+T231, D27+N233, D27+D254, D27+P256, N33+G38, N33+F51, N33+E56, N33+L69, N33+D96, N33+K98, N33+D111, N33+G163, N33+V176, N33+H198, N33+E210, N33+Y220, N33+L227, N33+T231, N33+N233, N33+D254, N33+P256, G38+F51, G38+E56, G38+L69, G38+D96, G38+K98, G38+D111, G38+G163, G38+V176, G38+H198, G38+E210, G38+Y220, G38+L227, G38+T231, G38+N233, G38+D254, G38+P256, F51+E56, F51+L69, F51+D96, F51+K98, F51+D111, F51+G163, F51+V176, F51+H198, F51+E210, F51+Y220, F51+L227, F51+T231, F51+N233, F51+D254, F51+P256, E56+L69, E56+D96, E56+K98, E56+D111, E56+G163, E56+V176, E56+H198, E56+E210, E56+Y220, E56+L227, E56+T231, E56+N233, E56+D254, E56+P256, L69+D96, L69+K98, L69+D111, L69+G163, L69+V176, L69+H198, L69+E210, L69+Y220, L69+L227, L69+T231, L69+N233, L69+D254, L69+P256, D96+K98, D96+D111, D96+G163, D96+V176, D96+H198, D96+E210, D96+Y220, D96+L227, D96+T231, D96+N233, D96+D254, D96+P256, K98+D111, K98+G163, K98+V176, K98+H198, K98+E210, K98+Y220, K98+L227, K98+T231, K98+N233, K98+D254, K98+P256, D111+G163, D111+V176, D111+H198, D111+E210, D111+Y220, D111+L227, D111+T231, D111+N233, D111+D254, D111+P256, G163+V176, G163+H198, G163+E210, G163+Y220, G163+L227, G163+T231, G163+N233, G163+D254, G163+P256, V176+H198, V176+E210, V176+Y220, V176+L227, V176+T231, V176+N233, V176+D254, V176+P256, H198+E210, H198+Y220, H198+L227, H198+T231, H198+N233, H198+D254, H198+P256, E210+Y220, E210+L227, E210+T231, E210+N233, E210+D254, E210+P256, Y220+L227, Y220+T231, Y220+N233, Y220+D254, Y220+P256, L227+T231, L227+N233, L227+D254, L227+P256, T231+N233, T231+D254, T231+P256, N233+D254, N233+P256, and D254+P256, wherein numbering is according to SEQ ID NO: 1.

In one embodiment, the lipase variant comprises a modification in three positions corresponding to positions E1, V2, N33, F51, E56, L69, K98, V176, H198, E210, Y220, and L227 of SEQ ID NO: 1. Thus, in one embodiment, the lipase variant comprises a modification in three positions selected from the group consisting of: E1+V2+N33, E1+V2+F51, E1+V2+E56, E1+V2+L69, E1+V2+K98, E1+V2+V176, E1+V2+H198, E1+V2+E210, E1+V2+Y220, E1+V2+L227, E1+N33+F51, E1+N33+E56, E1+N33+L69, E1+N33+K98, E1+N33+V176, E1+N33+H198, E1+N33+E210, E1+N33+Y220, E1+N33+L227, E1+F51+E56, E1+F51+L69, E1+F51+K98, E1+F51+V176, E1+F51+H198, E1+F51+E210, E1+F51+Y220, E1+F51+L227, E1+E56+L69, E1+E56+K98, E1+E56+V176, E1+E56+H198, E1+E56+E210, E1+E56+Y220, E1+E56+L227, E1+L69+K98, E1+L69+V176, E1+L69+H198, E1+L69+E210, E1+L69+Y220, E1+L69+L227, E1+K98+V176, E1+K98+H198, E1+K98+E210, E1+K98+Y220, E1+K98+L227, E1+V176+H198, E1+V176+E210, E1+V176+Y220, E1+V176+L227, E1+H198+E210, E1+H198+Y220, E1+H198+L227, E1+E210+Y220, E1+E210+L227, E1+Y220+L227, V2+N33+F51, V2+N33+E56, V2+N33+L69, V2+N33+K98, V2+N33+V176, V2+N33+H198, V2+N33+E210, V2+N33+Y220, V2+N33+L227, V2+F51+E56, V2+F51+L69, V2+F51+K98, V2+F51+V176, V2+F51+H198, V2+F51+E210, V2+F51+Y220, V2+F51+L227, V2+E56+L69, V2+E56+K98, V2+E56+V176, V2+E56+H198, V2+E56+E210, V2+E56+Y220, V2+E56+L227, V2+L69+K98, V2+L69+V176, V2+L69+H198, V2+L69+E210, V2+L69+Y220, V2+L69+L227, V2+K98+V176, V2+K98+H198, V2+K98+E210, V2+K98+Y220, V2+K98+L227, V2+V176+H198, V2+V176+E210, V2+V176+Y220, V2+V176+L227, V2+H198+E210, V2+H198+Y220, V2+H198+L227, V2+E210+Y220, V2+E210+L227, V2+Y220+L227, N33+F51+E56, N33+F51+L69, N33+F51+K98, N33+F51+V176, N33+F51+H198, N33+F51+E210, N33+F51+Y220, N33+F51+L227, N33+E56+L69, N33+E56+K98, N33+E56+V176, N33+E56+H198, N33+E56+E210, N33+E56+Y220, N33+E56+L227, N33+L69+K98, N33+L69+V176, N33+L69+H198, N33+L69+E210, N33+L69+Y220, N33+L69+L227, N33+K98+V176, N33+K98+H198, N33+K98+E210, N33+K98+Y220, N33+K98+L227, N33+V176+H198, N33+V176+E210, N33+V176+Y220, N33+V176+L227, N33+H198+E210, N33+H198+Y220, N33+H198+L227, N33+E210+Y220, N33+E210+L227, N33+Y220+L227, F51+E56+L69, F51+E56+K98, F51+E56+V176, F51+E56+H198, F51+E56+E210, F51+E56+Y220, F51+E56+L227, F51+L69+K98, F51+L69+V176, F51+L69+H198, F51+L69+E210, F51+L69+Y220, F51+L69+L227, F51+K98+V176, F51+K98+H198, F51+K98+E210, F51+K98+Y220, F51+K98+L227, F51+V176+H198, F51+V176+E210, F51+V176+Y220, F51+V176+L227, F51+H198+E210, F51+H198+Y220, F51+H198+L227, F51+E210+Y220, F51+E210+L227, F51+Y220+L227, E56+L69+K98, E56+L69+V176, E56+L69+H198, E56+L69+E210, E56+L69+Y220, E56+L69+L227, E56+K98+V176, E56+K98+H198, E56+K98+E210, E56+K98+Y220, E56+K98+L227, E56+V176+H198, E56+V176+E210, E56+V176+Y220, E56+V176+L227, E56+H198+E210, E56+H198+Y220, E56+H198+L227, E56+E210+Y220, E56+E210+L227, E56+Y220+L227, L69+K98+V176, L69+K98+H198, L69+K98+E210, L69+K98+Y220, L69+K98+L227, L69+V176+H198, L69+V176+E210, L69+V176+Y220, L69+V176+L227, L69+H198+E210, L69+H198+Y220, L69+H198+L227, L69+E210+Y220, L69+E210+L227, L69+Y220+L227, K98+V176+H198, K98+V176+E210, K98+V176+Y220, K98+V176+L227, K98+H198+E210, K98+H198+Y220, K98+H198+L227, K98+E210+Y220, K98+E210+L227, K98+Y220+L227, V176+H198+E210, V176+H198+Y220, V176+H198+L227, V176+E210+Y220, V176+E210+L227, V176+Y220+L227, H198+E210+Y220, H198+E210+L227, H198+Y220+L227, and E210+Y220+L227, wherein numbering is according to SEQ ID NO: 1.

In one embodiment, the lipase variant comprises a modification in three positions corresponding to positions E1, V2, D27, N33, G38, F51, E56, L69, D96, K98, D111, G163, V176, H198, E210, Y220, L227, T231, N233, N233, D254, and P256, wherein numbering is according to SEQ ID NO: 1. Thus, in a particular embodiment, the lipase variant comprises a modification in three positions selected from the group consisting of: E1+V2+D27, E1+V2+N33, E1+V2+G38, E1+V2+F51, E1+V2+E56, E1+V2+L69, E1+V2+D96, E1+V2+K98, E1+V2+D111, E1+V2+G163, E1+V2+V176, E1+V2+H198, E1+V2+E210, E1+V2+Y220, E1+V2+L227, E1+V2+T231, E1+V2+N233, E1+V2+D254, E1+V2+P256, E1+D27+N33, E1+D27+G38, E1+D27+F51, E1+D27+E56, E1+D27+L69, E1+D27+D96, E1+D27+K98, E1+D27+D111, E1+D27+G163, E1+D27+V176, E1+D27+H198, E1+D27+E210, E1+D27+Y220, E1+D27+L227, E1+D27+T231, E1+D27+N233, E1+D27+D254, E1+D27+P256, E1+N33+G38, E1+N33+F51, E1+N33+E56, E1+N33+L69, E1+N33+D96, E1+N33+K98, E1+N33+D111, E1+N33+G163, E1+N33+V176, E1+N33+H198, E1+N33+E210, E1+N33+Y220, E1+N33+L227, E1+N33+T231, E1+N33+N233, E1+N33+D254, E1+N33+P256, E1+G38+F51, E1+G38+E56, E1+G38+L69, E1+G38+D96, E1+G38+K98, E1+G38+D111, E1+G38+G163, E1+G38+V176, E1+G38+H198, E1+G38+E210, E1+G38+Y220, E1+G38+L227, E1+G38+T231, E1+G38+N233, E1+G38+D254, E1+G38+P256, E1+F51+E56, E1+F51+L69, E1+F51+D96, E1+F51+K98, E1+F51+D111, E1+F51+G163, E1+F51+V176, E1+F51+H198, E1+F51+E210, E1+F51+Y220, E1+F51+L227, E1+F51+T231, E1+F51+N233, E1+F51+D254, E1+F51+P256, E1+E56+L69, E1+E56+D96, E1+E56+K98, E1+E56+D111, E1+E56+G163, E1+E56+V176, E1+E56+H198, E1+E56+E210, E1+E56+Y220, E1+E56+L227, E1+E56+T231, E1+E56+N233, E1+E56+D254, E1+E56+P256, E1+L69+D96, E1+L69+K98, E1+L69+D111, E1+L69+G163, E1+L69+V176, E1+L69+H198, E1+L69+E210, E1+L69+Y220, E1+L69+L227, E1+L69+T231, E1+L69+N233, E1+L69+D254, E1+L69+P256, E1+D96+K98, E1+D96+D111, E1+D96+G163, E1+D96+V176, E1+D96+H198, E1+D96+E210, E1+D96+Y220, E1+D96+L227, E1+D96+T231, E1+D96+N233, E1+D96+D254, E1+D96+P256, E1+K98+D111, E1+K98+G163, E1+K98+V176, E1+K98+H198, E1+K98+E210, E1+K98+Y220, E1+K98+L227, E1+K98+T231, E1+K98+N233, E1+K98+D254, E1+K98+P256, E1+D111+G163, E1+D111+V176, E1+D111+H198, E1+D111+E210, E1+D111+Y220, E1+D111+L227, E1+D111+T231, E1+D111+N233, E1+D111+D254, E1+D111+P256, E1+G163+V176, E1+G163+H198, E1+G163+E210, E1+G163+Y220, E1+G163+L227, E1+G163+T231, E1+G163+N233, E1+G163+D254, E1+G163+P256, E1+V176+H198, E1+V176+E210, E1+V176+Y220, E1+V176+L227, E1+V176+T231, E1+V176+N233, E1+V176+D254, E1+V176+P256, E1+H198+E210, E1+H198+Y220, E1+H198+L227, E1+H198+T231, E1+H198+N233, E1+H198+D254, E1+H198+P256, E1+E210+Y220, E1+E210+L227, E1+E210+T231, E1+E210+N233, E1+E210+D254, E1+E210+P256, E1+Y220+L227, E1+Y220+T231, E1+Y220+N233, E1+Y220+D254, E1+Y220+P256, E1+L227+T231, E1+L227+N233, E1+L227+D254, E1+L227+P256, E1+T231+N233, E1+T231+D254, E1+T231+P256, E1+N233+D254, E1+N233+P256, E1+D254+P256, V2+D27+N33, V2+D27+G38, V2+D27+F51, V2+D27+E56, V2+D27+L69, V2+D27+D96, V2+D27+K98, V2+D27+D111, V2+D27+G163, V2+D27+V176, V2+D27+H198, V2+D27+E210, V2+D27+Y220, V2+D27+L227, V2+D27+T231, V2+D27+N233, V2+D27+D254, V2+D27+P256, V2+N33+G38, V2+N33+F51, V2+N33+E56, V2+N33+L69, V2+N33+D96, V2+N33+K98, V2+N33+D111, V2+N33+G163, V2+N33+V176, V2+N33+H198, V2+N33+E210, V2+N33+Y220, V2+N33+L227, V2+N33+T231, V2+N33+N233, V2+N33+D254, V2+N33+P256, V2+G38+F51, V2+G38+E56, V2+G38+L69, V2+G38+D96, V2+G38+K98, V2+G38+D111, V2+G38+G163, V2+G38+V176, V2+G38+H198, V2+G38+E210, V2+G38+Y220, V2+G38+L227, V2+G38+T231, V2+G38+N233, V2+G38+D254, V2+G38+P256, V2+F51+E56, V2+F51+L69, V2+F51+D96, V2+F51+K98, V2+F51+D111, V2+F51+G163, V2+F51+V176, V2+F51+H198, V2+F51+E210, V2+F51+Y220, V2+F51+L227, V2+F51+T231, V2+F51+N233, V2+F51+D254, V2+F51+P256, V2+E56+L69, V2+E56+D96, V2+E56+K98, V2+E56+D111, V2+E56+G163, V2+E56+V176, V2+E56+H198, V2+E56+E210, V2+E56+Y220, V2+E56+L227, V2+E56+T231, V2+E56+N233, V2+E56+D254, V2+E56+P256, V2+L69+D96, V2+L69+K98, V2+L69+D111, V2+L69+G163, V2+L69+V176, V2+L69+H198, V2+L69+E210, V2+L69+Y220, V2+L69+L227, V2+L69+T231, V2+L69+N233, V2+L69+D254, V2+L69+P256, V2+D96+K98, V2+D96+D111, V2+D96+G163, V2+D96+V176, V2+D96+H198, V2+D96+E210, V2+D96+Y220, V2+D96+L227, V2+D96+T231, V2+D96+N233, V2+D96+D254, V2+D96+P256, V2+K98+D111, V2+K98+G163, V2+K98+V176, V2+K98+H198, V2+K98+E210, V2+K98+Y220, V2+K98+L227, V2+K98+T231, V2+K98+N233, V2+K98+D254, V2+K98+P256, V2+D111+G163, V2+D111+V176, V2+D111+H198, V2+D111+E210, V2+D111+Y220, V2+D111+L227, V2+D111+T231, V2+D111+N233, V2+D111+D254, V2+D111+P256, V2+G163+V176, V2+G163+H198, V2+G163+E210, V2+G163+Y220, V2+G163+L227, V2+G163+T231, V2+G163+N233, V2+G163+D254, V2+G163+P256, V2+V176+H198, V2+V176+E210, V2+V176+Y220, V2+V176+L227, V2+V176+T231, V2+V176+N233, V2+V176+D254, V2+V176+P256, V2+H198+E210, V2+H198+Y220, V2+H198+L227, V2+H198+T231, V2+H198+N233, V2+H198+D254, V2+H198+P256, V2+E210+Y220, V2+E210+L227, V2+E210+T231, V2+E210+N233, V2+E210+D254, V2+E210+P256, V2+Y220+L227, V2+Y220+T231, V2+Y220+N233, V2+Y220+D254, V2+Y220+P256, V2+L227+T231, V2+L227+N233, V2+L227+D254, V2+L227+P256, V2+T231+N233, V2+T231+D254, V2+T231+P256, V2+N233+D254, V2+N233+P256, V2+D254+P256, D27+N33+G38, D27+N33+F51, D27+N33+E56, D27+N33+L69, D27+N33+D96, D27+N33+K98, D27+N33+D111, D27+N33+G163, D27+N33+V176, D27+N33+H198, D27+N33+E210, D27+N33+Y220, D27+N33+L227, D27+N33+T231, D27+N33+N233, D27+N33+D254, D27+N33+P256, D27+G38+F51, D27+G38+E56, D27+G38+L69, D27+G38+D96, D27+G38+K98, D27+G38+D111, D27+G38+G163, D27+G38+V176, D27+G38+H198, D27+G38+E210, D27+G38+Y220, D27+G38+L227, D27+G38+T231, D27+G38+N233, D27+G38+D254, D27+G38+P256, D27+F51+E56, D27+F51+L69, D27+F51+D96, D27+F51+K98, D27+F51+D111, D27+F51+G163, D27+F51+V176, D27+F51+H198, D27+F51+E210, D27+F51+Y220, D27+F51+L227, D27+F51+T231, D27+F51+N233, D27+F51+D254, D27+F51+P256, D27+E56+L69, D27+E56+D96, D27+E56+K98, D27+E56+D111, D27+E56+G163, D27+E56+V176, D27+E56+H198, D27+E56+E210, D27+E56+Y220, D27+E56+L227, D27+E56+T231, D27+E56+N233, D27+E56+D254, D27+E56+P256, D27+L69+D96, D27+L69+K98, D27+L69+D111, D27+L69+G163, D27+L69+V176, D27+L69+H198, D27+L69+E210, D27+L69+Y220, D27+L69+L227, D27+L69+T231, D27+L69+N233, D27+L69+D254, D27+L69+P256, D27+D96+K98, D27+D96+D111, D27+D96+G163, D27+D96+V176, D27+D96+H198, D27+D96+E210, D27+D96+Y220, D27+D96+L227, D27+D96+T231, D27+D96+N233, D27+D96+D254, D27+D96+P256, D27+K98+D111, D27+K98+G163, D27+K98+V176, D27+K98+H198, D27+K98+E210, D27+K98+Y220, D27+K98+L227, D27+K98+T231, D27+K98+N233, D27+K98+D254, D27+K98+P256, D27+D111+G163, D27+D111+V176, D27+D111+H198, D27+D111+E210, D27+D111+Y220, D27+

D111+L227, D27+D111+T231, D27+D111+N233, D27+D111+D254, D27+D111+P256, D27+G163+V176, D27+G163+H198, D27+G163+E210, D27+G163+Y220, D27+G163+L227, D27+G163+T231, D27+G163+N233, D27+G163+D254, D27+G163+P256, D27+V176+H198, D27+V176+E210, D27+V176+Y220, D27+V176+L227, D27+V176+T231, D27+V176+N233, D27+V176+D254, D27+V176+P256, D27+H198+E210, D27+H198+Y220, D27+H198+L227, D27+H198+T231, D27+H198+N233, D27+H198+D254, D27+H198+P256, D27+E210+Y220, D27+E210+L227, D27+E210+T231, D27+E210+N233, D27+E210+D254, D27+E210+P256, D27+Y220+L227, D27+Y220+T231, D27+Y220+N233, D27+Y220+D254, D27+Y220+P256, D27+L227+T231, D27+L227+N233, D27+L227+D254, D27+L227+P256, D27+T231+N233, D27+T231+D254, D27+T231+P256, D27+N233+D254, D27+N233+P256, D27+D254+P256, N33+G38+F51, N33+G38+E56, N33+G38+L69, N33+G38+D96, N33+G38+K98, N33+G38+D111, N33+G38+G163, N33+G38+V176, N33+G38+H198, N33+G38+E210, N33+G38+Y220, N33+G38+L227, N33+G38+T231, N33+G38+N233, N33+G38+D254, N33+G38+P256, N33+F51+E56, N33+F51+L69, N33+F51+D96, N33+F51+K98, N33+F51+D111, N33+F51+G163, N33+F51+V176, N33+F51+H198, N33+F51+E210, N33+F51+Y220, N33+F51+L227, N33+F51+T231, N33+F51+N233, N33+F51+D254, N33+F51+P256, N33+E56+L69, N33+E56+D96, N33+E56+K98, N33+E56+D111, N33+E56+G163, N33+E56+V176, N33+E56+H198, N33+E56+E210, N33+E56+Y220, N33+E56+L227, N33+E56+T231, N33+E56+N233, N33+E56+D254, N33+E56+P256, N33+L69+D96, N33+L69+K98, N33+L69+D111, N33+L69+G163, N33+L69+V176, N33+L69+H198, N33+L69+E210, N33+L69+Y220, N33+L69+L227, N33+L69+T231, N33+L69+N233, N33+L69+D254, N33+L69+P256, N33+D96+K98, N33+D96+D111, N33+D96+G163, N33+D96+V176, N33+D96+H198, N33+D96+E210, N33+D96+Y220, N33+D96+L227, N33+D96+T231, N33+D96+N233, N33+D96+D254, N33+D96+P256, N33+K98+D111, N33+K98+G163, N33+K98+V176, N33+K98+H198, N33+K98+E210, N33+K98+Y220, N33+K98+L227, N33+K98+T231, N33+K98+N233, N33+K98+D254, N33+K98+P256, N33+D111+G163, N33+D111+V176, N33+D111+H198, N33+D111+E210, N33+D111+Y220, N33+D111+L227, N33+D111+T231, N33+D111+N233, N33+D111+D254, N33+D111+P256, N33+G163+V176, N33+G163+H198, N33+G163+E210, N33+G163+Y220, N33+G163+L227, N33+G163+T231, N33+G163+N233, N33+G163+D254, N33+G163+P256, N33+V176+H198, N33+V176+E210, N33+V176+Y220, N33+V176+L227, N33+V176+T231, N33+V176+N233, N33+V176+D254N33+V176+P256, N33+H198+E210, N33+H198+Y220, N33+H198+L227, N33+H198+T231, N33+H198+N233, N33+H198+D254, N33+H198+P256, N33+E210+Y220, N33+E210+L227, N33+E210+T231, N33+E210+N233, N33+E210+D254, N33+E210+P256, N33+Y220+L227, N33+Y220+T231, N33+Y220+N233, N33+Y220+D254, N33+Y220+P256, N33+L227+T231, N33+L227+N233, N33+L227+D254, N33+L227+P256, N33+T231+N233, N33+T231+D254, N33+T231+P256, N33+N233+D254, N33+N233+P256, N33+D254+P256, G38+F51+E56, G38+F51+L69, G38+F51+D96, G38+F51+K98, G38+F51+D111, G38+F51+G163, G38+F51+V176, G38+F51+H198, G38+F51+E210, G38+F51+Y220, G38+F51+L227, G38+F51+T231, G38+F51+N233, G38+F51+D254, G38+F51+P256, G38+E56+L69, G38+E56+D96, G38+E56+K98, G38+E56+D111, G38+E56+G163, G38+E56+V176, G38+E56+H198, G38+E56+E210, G38+E56+Y220, G38+E56+L227, G38+E56+T231, G38+E56+N233, G38+E56+D254, G38+E56+P256, G38+L69+D96, G38+L69+K98, G38+L69+D111, G38+L69+G163, G38+L69+V176, G38+L69+H198, G38+L69+E210, G38+L69+Y220, G38+L69+L227, G38+L69+T231, G38+L69+N233, G38+L69+D254, G38+L69+P256, G38+D96+K98, G38+D96+D111, G38+D96+G163, G38+D96+V176, G38+D96+H198, G38+D96+E210, G38+D96+Y220, G38+D96+L227, G38+D96+T231, G38+D96+N233, G38+D96+D254, G38+D96+P256, G38+K98+D111, G38+K98+G163, G38+K98+V176, G38+K98+H198, G38+K98+E210, G38+K98+Y220, G38+K98+L227, G38+K98+T231, G38+K98+N233, G38+K98+D254, G38+K98+P256, G38+D111+G163, G38+D111+V176, G38+D111+H198, G38+D111+E210, G38+D111+Y220, G38+D111+L227, G38+D111+T231, G38+D111+N233, G38+D111+D254, G38+D111+P256, G38+G163+V176, G38+G163+H198, G38+G163+E210, G38+G163+Y220, G38+G163+L227, G38+G163+T231, G38+G163+N233, G38+G163+D254, G38+G163+P256, G38+V176+H198, G38+V176+E210, G38+V176+Y220, G38+V176+L227, G38+V176+T231, G38+V176+N233, G38+V176+D254, G38+V176+P256, G38+H198+E210, G38+H198+Y220, G38+H198+L227, G38+H198+T231, G38+H198+N233, G38+H198+D254, G38+H198+P256, G38+E210+Y220, G38+E210+L227, G38+E210+T231, G38+E210+N233, G38+E210+D254, G38+E210+P256, G38+Y220+L227, G38+Y220+T231, G38+Y220+N233, G38+Y220+D254, G38+Y220+P256, G38+L227+T231, G38+L227+N233, G38+L227+D254, G38+L227+P256, G38+T231+N233, G38+T231+D254, G38+T231+P256, G38+N233+D254, G38+N233+P256, G38+D254+P256, F51+E56+L69, F51+E56+D96, F51+E56+K98, F51+E56+D111, F51+E56+G163, F51+E56+V176, F51+E56+H198, F51+E56+E210, F51+E56+Y220, F51+E56+L227, F51+E56+T231, F51+E56+N233, F51+E56+D254, F51+E56+P256, F51+L69+D96, F51+L69+K98, F51+L69+D111, F51+L69+G163, F51+L69+V176, F51+L69+H198, F51+L69+E210, F51+L69+Y220, F51+L69+L227, F51+L69+T231, F51+L69+N233, F51+L69+D254, F51+L69+P256, F51+D96+K98, F51+D96+D111, F51+D96+G163, F51+D96+V176, F51+D96+H198, F51+D96+E210, F51+D96+Y220, F51+D96+L227, F51+D96+T231, F51+D96+N233, F51+D96+D254, F51+D96+P256, F51+K98+D111, F51+K98+G163, F51+K98+V176, F51+K98+H198, F51+K98+E210, F51+K98+Y220, F51+K98+L227, F51+K98+T231, F51+K98+N233, F51+K98+D254, F51+K98+P256, F51+D111+G163, F51+D111+V176, F51+D111+H198, F51+D111+E210, F51+D111+Y220, F51+D111+L227, F51+D111+T231, F51+D111+N233, F51+D111+D254, F51+D111+P256, F51+G163+V176, F51+G163+H198, F51+G163+E210, F51+G163+Y220, F51+G163+L227, F51+G163+T231, F51+G163+N233, F51+G163+D254, F51+G163+P256, F51+V176+H198, F51+V176+E210, F51+V176+Y220, F51+V176+L227, F51+V176+T231, F51+V176+N233, F51+V176+D254, F51+V176+P256, F51+H198+E210, F51+H198+Y220, F51+H198+L227, F51+H198+T231, F51+H198+N233, F51+H198+D254, F51+H198+P256, F51+E210+Y220, F51+E210+L227, F51+E210+T231, F51+E210+N233, F51+E210+D254, F51+E210+P256, F51+Y220+L227, F51+Y220+T231, F51+Y220+N233, F51+Y220+D254, F51+Y220+P256, F51+L227+T231, F51+L227+N233, F51+L227+D254, F51+L227+P256, F51+T231+N233, F51+T231+D254, F51+T231+P256, F51+N233+D254, F51+N233+P256, F51+D254+P256, E56+L69+D96, E56+L69+K98, E56+L69+D111, E56+L69+G163, E56+L69+V176, E56+L69+H198, E56+L69+E210, E56+L69+Y220, E56+L69+L227, E56+L69+T231, E56+L69+N233, E56+L69+D254, E56+

L69+P256, E56+D96+K98, E56+D96+D111, E56+D96+G163, E56+D96+V176, E56+D96+H198, E56+D96+E210, E56+D96+Y220, E56+D96+L227, E56+D96+T231, E56+D96+N233, E56+D96+D254, E56+D96+P256, E56+K98+D111, E56+K98+G163, E56+K98+V176, E56+K98+H198, E56+K98+E210, E56+K98+Y220, E56+K98+L227, E56+K98+T231, E56+K98+N233, E56+K98+D254, E56+K98+P256, E56+D111+G163, E56+D111+V176, E56+D111+H198, E56+D111+E210, E56+D111+Y220, E56+D111+L227, E56+D111+T231, E56+D111+N233, E56+D111+D254, E56+D111+P256, E56+G163+V176, E56+G163+H198, E56+G163+E210, E56+G163+Y220, E56+G163+L227, E56+G163+T231, E56+G163+N233, E56+G163+D254, E56+G163+P256, E56+V176+H198, E56+V176+E210, E56+V176+Y220, E56+V176+L227, E56+V176+T231, E56+V176+N233, E56+V176+D254, E56+V176+P256, E56+H198+E210, E56+H198+Y220, E56+H198+L227, E56+H198+T231, E56+H198+N233, E56+H198+D254, E56+H198+P256, E56+E210+Y220, E56+E210+L227, E56+E210+T231, E56+E210+N233, E56+E210+D254, E56+E210+P256, E56+Y220+L227, E56+Y220+T231, E56+Y220+N233, E56+Y220+D254, E56+Y220+P256, E56+L227+T231, E56+L227+N233, E56+L227+D254, E56+L227+P256, E56+T231+N233, E56+T231+D254, E56+T231+P256, E56+N233+D254, E56+N233+P256, E56+D254+P256, L69+D96+K98, L69+D96+D111, L69+D96+G163, L69+D96+V176, L69+D96+H198, L69+D96+E210, L69+D96+Y220, L69+D96+L227, L69+D96+T231, L69+D96+N233, L69+D96+D254, L69+D96+P256, L69+K98+D111, L69+K98+G163, L69+K98+V176, L69+K98+H198, L69+K98+E210, L69+K98+Y220, L69+K98+L227, L69+K98+T231, L69+K98+N233, L69+K98+D254, L69+K98+P256, L69+D111+G163, L69+D111+V176, L69+D111+H198, L69+D111+E210, L69+D111+Y220, L69+D111+L227, L69+D111+T231, L69+D111+N233, L69+D111+D254, L69+D111+P256, L69+G163+V176, L69+G163+H198, L69+G163+E210, L69+G163+Y220, L69+G163+L227, L69+G163+T231, L69+G163+N233, L69+G163+D254, L69+G163+P256, L69+V176+H198, L69+V176+E210, L69+V176+Y220, L69+V176+L227, L69+V176+T231, L69+V176+N233, L69+V176+D254, L69+V176+P256, L69+H198+E210, L69+H198+Y220, L69+H198+L227, L69+H198+T231, L69+H198+N233, L69+H198+D254, L69+H198+P256, L69+E210+Y220, L69+E210+L227, L69+E210+T231, L69+E210+N233, L69+E210+D254, L69+E210+P256, L69+Y220+L227, L69+Y220+T231, L69+Y220+N233, L69+Y220+D254, L69+Y220+P256, L69+L227+T231, L69+L227+N233, L69+L227+D254, L69+L227+P256, L69+T231+N233, L69+T231+D254, L69+T231+P256, L69+N233+D254, L69+N233+P256, L69+D254+P256, D96+K98+D111, D96+K98+G163, D96+K98+V176, D96+K98+H198, D96+K98+E210, D96+K98+Y220, D96+K98+L227, D96+K98+T231, D96+K98+N233, D96+K98+D254, D96+K98+P256, D96+D111+G163, D96+D111+V176, D96+D111+H198, D96+D111+E210, D96+D111+Y220, D96+D111+L227, D96+D111+T231, D96+D111+N233, D96+D111+D254, D96+D111+P256, D96+G163+V176, D96+G163+H198, D96+G163+E210, D96+G163+Y220, D96+G163+L227, D96+G163+T231, D96+G163+N233, D96+G163+D254, D96+G163+P256, D96+V176+H198, D96+V176+E210, D96+V176+Y220, D96+V176+L227, D96+V176+T231, D96+V176+N233, D96+V176+D254, D96+V176+P256, D96+H198+E210, D96+H198+Y220, D96+H198+L227, D96+H198+T231, D96+H198+N233, D96+H198+D254, D96+H198+P256, D96+E210+Y220, D96+E210+L227, D96+E210+T231, D96+E210+N233, D96+E210+D254, D96+E210+P256, D96+Y220+L227, D96+Y220+T231, D96+Y220+N233, D96+Y220+D254, D96+Y220+P256, D96+L227+T231, D96+L227+N233, D96+L227+D254, D96+L227+P256, D96+T231+N233, D96+T231+D254, D96+T231+P256, D96+N233+D254, D96+N233+P256, D96+D254+P256, K98+D111+G163, K98+D111+V176, K98+D111+H198, K98+D111+E210, K98+D111+Y220, K98+D111+L227, K98+D111+T231, K98+D111+N233, K98+D111+D254, K98+D111+P256, K98+G163+V176, K98+G163+H198, K98+G163+E210, K98+G163+Y220, K98+G163+L227, K98+G163+T231, K98+G163+N233, K98+G163+D254, K98+G163+P256, K98+V176+H198, K98+V176+E210, K98+V176+Y220, K98+V176+L227, K98+V176+T231, K98+V176+N233, K98+V176+D254, K98+V176+P256, K98+H198+E210, K98+H198+Y220, K98+H198+L227, K98+H198+T231, K98+H198+N233, K98+H198+D254, K98+H198+P256, K98+E210+Y220, K98+E210+L227, K98+E210+T231, K98+E210+N233, K98+E210+D254, K98+E210+P256, K98+Y220+L227, K98+Y220+T231, K98+Y220+N233, K98+Y220+D254, K98+Y220+P256, K98+L227+T231, K98+L227+N233, K98+L227+D254, K98+L227+P256, K98+T231+N233, K98+T231+D254, K98+T231+P256, K98+N233+D254, K98+N233+P256, K98+D254+P256, D111+G163+V176, D111+G163+H198, D111+G163+E210, D111+G163+Y220, D111+G163+L227, D111+G163+T231, D111+G163+N233, D111+G163+D254, D111+G163+P256, D111+V176+H198, D111+V176+E210, D111+V176+Y220, D111+V176+L227, D111+V176+T231, D111+V176+N233, D111+V176+D254, D111+V176+P256, D111+H198+E210, D111+H198+Y220, D111+H198+L227, D111+H198+T231, D111+H198+N233, D111+H198+D254, D111+H198+P256, D111+E210+Y220, D111+E210+L227, D111+E210+T231, D111+E210+N233, D111+E210+D254, D111+E210+P256, D111+Y220+L227, D111+Y220+T231, D111+Y220+N233, D111+Y220+D254, D111+Y220+P256, D111+L227+T231, D111+L227+N233, D111+L227+D254, D111+L227+P256, D111+T231+N233, D111+T231+D254, D111+T231+P256, D111+N233+D254, D111+N233+P256, D111+D254+P256, G163+V176+H198, G163+V176+E210, G163+V176+Y220, G163+V176+L227, G163+V176+T231, G163+V176+N233, G163+V176+D254, G163+V176+P256, G163+H198+E210, G163+H198+Y220, G163+H198+L227, G163+H198+T231, G163+H198+N233, G163+H198+D254, G163+H198+P256, G163+E210+Y220, G163+E210+L227, G163+E210+T231, G163+E210+N233, G163+E210+D254, G163+E210+P256, G163+Y220+L227, G163+Y220+T231, G163+Y220+N233, G163+Y220+D254, G163+Y220+P256, G163+L227+T231, G163+L227+N233, G163+L227+D254, G163+L227+P256, G163+T231+N233, G163+T231+D254, G163+T231+P256, G163+N233+D254, G163+N233+P256, G163+D254+P256, V176+H198+E210, V176+H198+Y220, V176+H198+L227, V176+H198+T231, V176+H198+N233, V176+H198+D254, V176+H198+P256, V176+E210+Y220, V176+E210+L227, V176+E210+T231, V176+E210+N233, V176+E210+D254, V176+E210+P256, V176+Y220+L227, V176+Y220+T231, V176+Y220+N233, V176+Y220+D254, V176+Y220+P256, V176+L227+T231, V176+L227+N233, V176+L227+D254, V176+L227+P256, V176+T231+N233, V176+T231+D254, V176+T231+P256, V176+N233+D254, V176+N233+P256, V176+D254+P256, H198+E210+Y220, H198+E210+L227, H198+E210+T231, H198+E210+N233, H198+E210+D254, H198+E210+P256, H198+Y220+L227, H198+Y220+T231, H198+Y220+N233, H198+Y220+D254, H198+Y220+

P256, H198+L227+T231, H198+L227+N233, H198+L227+D254, H198+L227+P256, H198+T231+N233, H198+T231+D254, H198+T231+P256, H198+N233+D254, H198+N233+P256, H198+D254+P256, E210+Y220+L227, E210+Y220+T231, E210+Y220+N233, E210+Y220+D254, E210+Y220+P256, E210+L227+T231, E210+L227+N233, E210+L227+D254, E210+L227+P256, E210+T231+N233, E210+T231+D254, E210+T231+P256, E210+N233+D254, E210+N233+P256, E210+D254+P256, Y220+L227+T231, Y220+L227+N233, Y220+L227+D254, Y220+L227+P256, Y220+T231+N233, Y220+T231+D254, Y220+T231+P256, Y220+N233+D254, Y220+N233+P256, Y220+D254+P256, L227+T231+N233, L227+T231+D254, L227+T231+P256, L227+N233+D254, L227+N233+P256, L227+D254+P256, T231+N233+D254, T231+N233+P256, T231+D254+P256, and N233+D254+P256, wherein numbering is according to SEQ ID NO: 1.

In one embodiment, the composition comprises a lipase variant comprising at least one of the following modifications; E1C, V2Y, D27R, N33K, G38A, F51V, E56K, L69R, D96E, K98I, D111A, G163K, V176L, H198S, E210K, Y220F, L227G, T231R, N233R, N233C, D254S, and P256T, wherein numbering is according to SEQ ID NO: 1.

In one embodiment, the lipase variant comprises two substitutions corresponding to the substitutions selected from the group consisting of: E1C+V2Y, E1C+D27R, E1C+N33K, E1C+G38A, E1C+F51V, E1C+E56K, E1C+L69R, E1C+D96E, E1C+K98I, E1C+D111A, E1C+G163K, E1C+V176L, E1C+H198S, E1C+E210K, E1C+Y220F, E1C+L227G, E1C+T231R, E1C+N233R, E1C+N233C, E1C+D254S, E1C+P256T, V2Y+D27R, V2Y+N33K, V2Y+G38A, V2Y+F51V, V2Y+E56K, V2Y+L69R, V2Y+D96E, V2Y+K98I, V2Y+D111A, V2Y+G163K, V2Y+V176L, V2Y+H198S, V2Y+E210K, V2Y+Y220F, V2Y+L227G, V2Y+T231R, V2Y+N233R, V2Y+N233C, V2Y+D254S, V2Y+P256T, D27R+N33K, D27R+G38A, D27R+F51V, D27R+E56K, D27R+L69R, D27R+D96E, D27R+K98I, D27R+D111A, D27R+G163K, D27R+V176L, D27R+H198S, D27R+E210K, D27R+Y220F, D27R+L227G, D27R+T231R, D27R+N233R, D27R+N233C, D27R+D254S, D27R+P256T, N33K+G38A, N33K+F51V, N33K+E56K, N33K+L69R, N33K+D96E, N33K+K98I, N33K+D111A, N33K+G163K, N33K+V176L, N33K+H198S, N33K+E210K, N33K+Y220F, N33K+L227G, N33K+T231R, N33K+N233R, N33K+N233C, N33K+D254S, N33K+P256T, G38A+F51V, G38A+E56K, G38A+L69R, G38A+D96E, G38A+K98I, G38A+D111A, G38A+G163K, G38A+V176L, G38A+H198S, G38A+E210K, G38A+Y220F, G38A+L227G, G38A+T231R, G38A+N233R, G38A+N233C, G38A+D254S, G38A+P256T, F51V+E56K, F51V+L69R, F51V+D96E, F51V+K98I, F51V+D111A, F51V+G163K, F51V+V176L, F51V+H198S, F51V+E210K, F51V+Y220F, F51V+L227G, F51V+T231R, F51V+N233R, F51V+N233C, F51V+D254S, F51V+P256T, E56K+L69R, E56K+D96E, E56K+K98I, E56K+D111A, E56K+G163K, E56K+V176L, E56K+H198S, E56K+E210K, E56K+Y220F, E56K+L227G, E56K+T231R, E56K+N233R, E56K+N233C, E56K+D254S, E56K+P256T, L69R+D96E, L69R+K98I, L69R+D111A, L69R+G163K, L69R+V176L, L69R+H198S, L69R+E210K, L69R+Y220F, L69R+L227G, L69R+T231R, L69R+N233R, L69R+N233C, L69R+D254S, L69R+P256T, D96E+K98I, D96E+D111A, D96E+G163K, D96E+V176L, D96E+H198S, D96E+E210K, D96E+Y220F, D96E+L227G, D96E+T231R, D96E+N233R, D96E+N233C, D96E+D254S, D96E+P256T, K98I+D111A, K98I+G163K, K98I+V176L, K98I+H198S, K98I+E210K, K98I+Y220F, K98I+L227G, K98I+T231R, K98I+N233R, K98I+N233C, K98I+D254S, K98I+P256T, D111A+G163K, D111A+V176L, D111A+H198S, D111A+E210K, D111A+Y220F, D111A+L227G, D111A+T231R, D111A+N233R, D111A+N233C, D111A+D254S, D111A+P256T, G163K+V176L, G163K+H198S, G163K+E210K, G163K+Y220F, G163K+L227G, G163K+T231R, G163K+N233R, G163K+N233C, G163K+D254S, G163K+P256T, V176L+H198S, V176L+E210K, V176L+Y220F, V176L+L227G, V176L+T231R, V176L+N233R, V176L+N233C, V176L+D254S, V176L+P256T, H198S+E210K, H198S+Y220F, H198S+L227G, H198S+T231R, H198S+N233R, H198S+N233C, H198S+D254S, H198S+P256T, E210K+Y220F, E210K+L227G, E210K+T231R, E210K+N233R, E210K+N233C, E210K+D254S, E210K+P256T, Y220F+L227G, Y220F+T231R, Y220F+N233R, Y220F+N233C, Y220F+D254S, Y220F+P256T, L227G+T231R, L227G+N233R, L227G+N233C, L227G+D254S, L227G+P256T, T231R+N233R, T231R+N233C, T231R+D254S, T231R+P256T, N233R+N233C, N233R+D254S, N233R+P256T, N233C+D254S, N233C+P256T, and D254S+P256T, wherein numbering is according to SEQ ID NO: 1.

In one embodiment, the lipase variant comprises three substitutions corresponding to substitutions selected from the group consisting of: E1C+V2Y+D27R, E1C+V2Y+N33K, E1C+V2Y+G38A, E1C+V2Y+F51V, E1C+V2Y+E56K, E1C+V2Y+L69R, E1C+V2Y+D96E, E1C+V2Y+K98I, E1C+V2Y+D111A, E1C+V2Y+G163K, E1C+V2Y+V176L, E1C+V2Y+H198S, E1C+V2Y+E210K, E1C+V2Y+Y220F, E1C+V2Y+L227G, E1C+V2Y+T231R, E1C+V2Y+N233R, E1C+V2Y+N233C, E1C+V2Y+D254S, E1C+V2Y+P256T, E1C+D27R+N33K, E1C+D27R+G38A, E1C+D27R+F51V, E1C+D27R+E56K, E1C+D27R+L69R, E1C+D27R+D96E, E1C+D27R+K98I, E1C+D27R+D111A, E1C+D27R+G163K, E1C+D27R+V176L, E1C+D27R+H198S, E1C+D27R+E210K, E1C+D27R+Y220F, E1C+D27R+L227G, E1C+D27R+T231R, E1C+D27R+N233R, E1C+D27R+N233C, E1C+D27R+D254S, E1C+D27R+P256T, E1C+N33K+G38A, E1C+N33K+F51V, E1C+N33K+E56K, E1C+N33K+L69R, E1C+N33K+D96E, E1C+N33K+K98I, E1C+N33K+D111A, E1C+N33K+G163K, E1C+N33K+V176L, E1C+N33K+H198S, E1C+N33K+E210K, E1C+N33K+Y220F, E1C+N33K+L227G, E1C+N33K+T231R, E1C+N33K+N233R, E1C+N33K+N233C, E1C+N33K+D254S, E1C+N33K+P256T, E1C+G38A+F51V, E1C+G38A+E56K, E1C+G38A+L69R, E1C+G38A+D96E, E1C+G38A+K98I, E1C+G38A+D111A, E1C+G38A+G163K, E1C+G38A+V176L, E1C+G38A+H198S, E1C+G38A+E210K, E1C+G38A+Y220F, E1C+G38A+L227G, E1C+G38A+T231R, E1C+G38A+N233R, E1C+G38A+N233C, E1C+G38A+D254S, E1C+G38A+P256T, E1C+F51V+E56K, E1C+F51V+L69R, E1C+F51V+D96E, E1C+F51V+K98I, E1C+F51V+D111A, E1C+F51V+G163K, E1C+F51V+V176L, E1C+F51V+H198S, E1C+F51V+E210K, E1C+F51V+Y220F, E1C+F51V+L227G, E1C+F51V+T231R, E1C+F51V+N233R, E1C+F51V+N233C, E1C+F51V+D254S, E1C+F51V+P256T, E1C+E56K+L69R, E1C+E56K+D96E, E1C+E56K+K98I, E1C+E56K+D111A, E1C+E56K+G163K, E1C+E56K+V176L, E1C+E56K+H198S, E1C+E56K+E210K, E1C+E56K+Y220F, E1C+E56K+L227G, E1C+E56K+T231R, E1C+E56K+N233R, E1C+E56K+N233C, E1C+E56K+D254S, E1C+E56K+P256T, E1C+L69R+D96E, E1C+L69R+K98I, E1C+L69R+D111A, E1C+L69R+G163K, E1C+L69R+V176L, E1C+L69R+H198S, E1C+L69R+E210K, E1C+L69R+Y220F, E1C+L69R+L227G, E1C+L69R+T231R, E1C+L69R+N233R, E1C+L69R+N233C, E1C+L69R+D254S, E1C+L69R+P256T, E1C+D96E+K98I, E1C+D96E+D111A, E1C+D96E+G163K, E1C+D96E+V176L, E1C+D96E+H198S, E1C+D96E+E210K, E1C+D96E+Y220F, E1C+D96E+L227G, E1C+D96E+T231R, E1C+D96E+N233R, E1C+D96E+N233C, E1C+D96E+D254S, E1C+D96E+P256T, E1C+K98I+D111A, E1C+K98I+G163K, E1C+K98I+V176L, E1C+K98I+H198S, E1C+K98I+E210K, E1C+K98I+Y220F, E1C+K98I+L227G, E1C+K98I+T231R, E1C+K98I+N233R, E1C+K98I+N233C, E1C+K98I+D254S, E1C+K98I+P256T, E1C+D111A+G163K, E1C+D111A+V176L, E1C+D111A+H198S, E1C+D111A+E210K, E1C+D111A+Y220F, E1C+D111A+L227G, E1C+D111A+T231R, E1C+D111A+N233R, E1C+D111A+N233C, E1C+D111A+D254S, E1C+D111A+P256T, E1C+G163K+V176L, E1C+G163K+H198S, E1C+G163K+E210K, E1C+G163K+Y220F, E1C+G163K+L227G, E1C+G163K+T231R, E1C+G163K+N233R, E1C+G163K+N233C, E1C+G163K+D254S, E1C+G163K+P256T, E1C+V176L+H198S, E1C+V176L+E210K, E1C+V176L+Y220F, E1C+V176L+L227G, E1C+V176L+T231R, E1C+V176L+N233R, E1C+V176L+N233C, E1C+V176L+D254S, E1C+V176L+P256T, E1C+H198S+E210K, E1C+H198S+Y220F, E1C+H198S+L227G, E1C+H198S+T231R, E1C+H198S+N233R, E1C+H198S+N233C, E1C+H198S+D254S, E1C+H198S+P256T, E1C+E210K+Y220F, E1C+E210K+L227G, E1C+E210K+T231R, E1C+E210K+N233R, E1C+E210K+N233C, E1C+E210K+D254S, E1C+E210K+P256T, E1C+Y220F+L227G, E1C+Y220F+T231R, E1C+Y220F+N233R, E1C+Y220F+N233C, E1C+Y220F+D254S, E1C+Y220F+P256T, E1C+L227G+T231R, E1C+L227G+N233R, E1C+L227G+N233C, E1C+L227G+D254S, E1C+L227G+P256T, E1C+T231R+N233R, E1C+T231R+N233C, E1C+T231R+D254S, E1C+T231R+P256T, E1C+N233R+N233C, E1C+N233R+D254S, E1C+N233R+P256T, E1C+N233C+D254S, E1C+N233C+P256T, E1C+D254S+P256T, V2Y+D27R+N33K, V2Y+D27R+G38A, V2Y+D27R+F51V, V2Y+D27R+E56K, V2Y+D27R+L69R, V2Y+D27R+D96E, V2Y+D27R+K98I, V2Y+D27R+D111A, V2Y+D27R+G163K, V2Y+D27R+V176L, V2Y+D27R+H198S, V2Y+D27R+E210K, V2Y+D27R+Y220F, V2Y+D27R+L227G, V2Y+D27R+T231R, V2Y+D27R+N233R, V2Y+D27R+N233C, V2Y+D27R+D254S, V2Y+D27R+P256T, V2Y+N33K+G38A, V2Y+N33K+F51V, V2Y+N33K+E56K, V2Y+N33K+L69R, V2Y+N33K+D96E, V2Y+N33K+K98I, V2Y+N33K+D111A, V2Y+N33K+G163K, V2Y+N33K+V176L, V2Y+N33K+H198S, V2Y+N33K+E210K, V2Y+N33K+Y220F, V2Y+N33K+L227G, V2Y+N33K+T231R, V2Y+N33K+N233R, V2Y+N33K+N233C, V2Y+N33K+D254S, V2Y+N33K+P256T, V2Y+G38A+F51V, V2Y+G38A+E56K, V2Y+G38A+L69R, V2Y+G38A+D96E, V2Y+G38A+K98I, V2Y+G38A+D111A, V2Y+G38A+G163K, V2Y+G38A+V176L, V2Y+G38A+H198S, V2Y+G38A+E210K, V2Y+G38A+Y220F, V2Y+G38A+L227G, V2Y+G38A+T231R, V2Y+G38A+N233R, V2Y+G38A+N233C, V2Y+G38A+D254S, V2Y+G38A+P256T, V2Y+F51V+E56K, V2Y+F51V+L69R, V2Y+F51V+D96E, V2Y+F51V+K98I, V2Y+F51V+D111A, V2Y+F51V+G163K, V2Y+F51V+V176L, V2Y+F51V+H198S, V2Y+F51V+E210K, V2Y+F51V+Y220F, V2Y+F51V+L227G, V2Y+F51V+T231R, V2Y+F51V+N233R, V2Y+F51V+N233C, V2Y+F51V+D254S, V2Y+F51V+P256T, V2Y+E56K+L69R, V2Y+E56K+D96E, V2Y+E56K+K98I, V2Y+E56K+D111A, V2Y+E56K+G163K, V2Y+E56K+V176L, V2Y+E56K+H198S, V2Y+E56K+E210K, V2Y+E56K+Y220F, V2Y+E56K+L227G, V2Y+E56K+T231R, V2Y+E56K+N233R, V2Y+E56K+N233C, V2Y+E56K+D254S, V2Y+E56K+P256T, V2Y+L69R+D96E, V2Y+L69R+K98I, V2Y+L69R+D111A, V2Y+L69R+G163K, V2Y+L69R+V176L, V2Y+L69R+H198S, V2Y+L69R+E210K, V2Y+L69R+Y220F, V2Y+L69R+L227G, V2Y+L69R+T231R, V2Y+L69R+N233R, V2Y+L69R+N233C, V2Y+L69R+D254S, V2Y+L69R+P256T, V2Y+D96E+K98I, V2Y+D96E+D111A, V2Y+D96E+G163K, V2Y+D96E+V176L, V2Y+D96E+H198S, V2Y+D96E+E210K, V2Y+D96E+Y220F, V2Y+D96E+L227G, V2Y+D96E+T231R, V2Y+D96E+N233R, V2Y+D96E+N233C, V2Y+D96E+D254S, V2Y+D96E+P256T, V2Y+K98I+D111A, V2Y+K98I+G163K, V2Y+K98I+V176L, V2Y+K98I+H198S, V2Y+K98I+E210K, V2Y+K98I+Y220F, V2Y+K98I+L227G, V2Y+K98I+T231R, V2Y+K98I+N233R, V2Y+K98I+N233C, V2Y+K98I+D254S, V2Y+K98I+P256T, V2Y+D111A+G163K, V2Y+D111A+V176L, V2Y+D111A+H198S, V2Y+D111A+E210K, V2Y+D111A+Y220F, V2Y+D111A+L227G, V2Y+D111A+T231R, V2Y+D111A+N233R, V2Y+D111A+N233C, V2Y+D111A+D254S, V2Y+D111A+P256T, V2Y+G163K+V176L, V2Y+G163K+H198S, V2Y+G163K+E210K, V2Y+G163K+Y220F, V2Y+G163K+L227G, V2Y+G163K+T231R, V2Y+G163K+N233R, V2Y+G163K+N233C, V2Y+G163K+D254S, V2Y+G163K+P256T, V2Y+V176L+H198S, V2Y+V176L+E210K, V2Y+V176L+Y220F, V2Y+V176L+L227G, V2Y+V176L+T231R, V2Y+V176L+N233R, V2Y+V176L+N233C, V2Y+V176L+D254S, V2Y+V176L+P256T, V2Y+H198S+E210K, V2Y+H198S+Y220F, V2Y+H198S+L227G, V2Y+H198S+T231R, V2Y+H198S+N233R, V2Y+H198S+N233C, V2Y+H198S+D254S, V2Y+H198S+P256T, V2Y+E210K+Y220F, V2Y+E210K+L227G, V2Y+E210K+T231R, V2Y+E210K+N233R, V2Y+E210K+N233C, V2Y+E210K+D254S, V2Y+E210K+P256T, V2Y+Y220F+L227G, V2Y+Y220F+T231R, V2Y+Y220F+N233R, V2Y+Y220F+N233C, V2Y+Y220F+D254S, V2Y+Y220F+P256T, V2Y+L227G+T231R, V2Y+L227G+N233R, V2Y+L227G+N233C, V2Y+L227G+D254S, V2Y+L227G+P256T, V2Y+T231R+N233R, V2Y+T231R+N233C, V2Y+T231R+D254S, V2Y+T231R+P256T, V2Y+N233R+N233C, V2Y+N233R+D254S, V2Y+N233R+P256T, V2Y+N233C+D254S, V2Y+N233C+P256T, V2Y+D254S+P256T, D27R+N33K+G38A, D27R+N33K+F51V, D27R+N33K+E56K, D27R+N33K+L69R, D27R+N33K+D96E, D27R+N33K+K98I, D27R+N33K+D111A, D27R+N33K+G163K, D27R+N33K+V176L, D27R+N33K+H198S, D27R+N33K+E210K, D27R+N33K+Y220F, D27R+N33K+L227G, D27R+N33K+T231R, D27R+N33K+N233R, D27R+N33K+N233C, D27R+N33K+D254S, D27R+N33K+P256T, D27R+G38A+F51V, D27R+G38A+E56K, D27R+G38A+L69R, D27R+G38A+D96E, D27R+G38A+K98I, D27R+G38A+D111A, D27R+G38A+G163K, D27R+G38A+V176L, D27R+G38A+H198S, D27R+G38A+E210K, D27R+G38A+Y220F, D27R+G38A+L227G, D27R+G38A+T231R, D27R+G38A+N233R, D27R+G38A+N233C, D27R+G38A+D254S, D27R+G38A+P256T, D27R+F51V+E56K, D27R+F51V+L69R, D27R+F51V+D96E, D27R+F51V+K98I, D27R+F51V+D111A, D27R+F51V+G163K, D27R+F51V+V176L, D27R+F51V+H198S, D27R+F51V+E210K, D27R+F51V+Y220F, D27R+F51V+L227G, D27R+F51V+T231R, D27R+F51V+N233R, D27R+F51V+N233C, D27R+F51V+D254S, D27R+F51V+P256T, D27R+E56K+L69R, D27R+E56K+D96E, D27R+E56K+K98I, D27R+E56K+D111A, D27R+E56K+G163K, D27R+E56K+V176L, D27R+E56K+H198S, D27R+E56K+E210K, D27R+E56K+Y220F, D27R+E56K+L227G, D27R+E56K+T231R, D27R+E56K+N233R, D27R+E56K+N233C, D27R+E56K+D254S, D27R+E56K+P256T, D27R+L69R+D96E, D27R+L69R+K98I, D27R+L69R+D111A, D27R+L69R+G163K, D27R+L69R+V176L, D27R+L69R+H198S, D27R+L69R+E210K, D27R+L69R+Y220F, D27R+L69R+L227G, D27R+L69R+T231R, D27R+L69R+N233R, D27R+L69R+N233C, D27R+L69R+D254S, D27R+L69R+P256T, D27R+D96E+K98I, D27R+D96E+D111A, D27R+D96E+G163K, D27R+D96E+V176L, D27R+D96E+H198S, D27R+D96E+E210K, D27R+D96E+Y220F, D27R+D96E+L227G, D27R+D96E+T231R, D27R+D96E+N233R, D27R+D96E+N233C, D27R+D96E+D254S, D27R+D96E+P256T, D27R+K98I+D111A, D27R+K98I+G163K, D27R+K98I+V176L, D27R+K98I+H198S, D27R+K98I+E210K, D27R+K98I+Y220F, D27R+K98I+L227G, D27R+K98I+T231R, D27R+K98I+N233R, D27R+K98I+N233C, D27R+K98I+D254S, D27R+K98I+P256T, D27R+D111A+G163K, D27R+D111A+V176L, D27R+D111A+H198S, D27R+D111A+E210K, D27R+D111A+Y220F, D27R+D111A+L227G, D27R+D111A+T231R, D27R+D111A+N233R, D27R+D111A+N233C, D27R+D111A+D254S, D27R+D111A+P256T, D27R+G163K+V176L, D27R+G163K+H198S, D27R+G163K+E210K, D27R+G163K+Y220F, D27R+G163K+L227G, D27R+G163K+T231R, D27R+G163K+N233R, D27R+G163K+N233C, D27R+G163K+D254S, D27R+G163K+P256T, D27R+V176L+H198S, D27R+V176L+E210K, D27R+V176L+Y220F, D27R+V176L+L227G, D27R+V176L+T231R, D27R+V176L+N233R, D27R+V176L+N233C, D27R+V176L+D254S, D27R+V176L+P256T, D27R+H198S+E210K, D27R+H198S+Y220F, D27R+H198S+L227G, D27R+H198S+T231R, D27R+H198S+N233R, D27R+H198S+N233C, D27R+H198S+D254S, D27R+H198S+P256T, D27R+E210K+Y220F, D27R+E210K+L227G, D27R+E210K+T231R, D27R+E210K+N233R, D27R+E210K+N233C, D27R+E210K+D254S, D27R+E210K+P256T, D27R+Y220F+L227G, D27R+Y220F+T231R, D27R+Y220F+N233R, D27R+Y220F+N233C, D27R+Y220F+D254S, D27R+Y220F+P256T, D27R+L227G+T231R, D27R+L227G+N233R, D27R+L227G+N233C, D27R+L227G+D254S, D27R+L227G+P256T, D27R+T231R+N233R, D27R+T231R+N233C, D27R+T231R+D254S, D27R+T231R+P256T, D27R+N233R+N233C, D27R+N233R+D254S, D27R+N233R+P256T, D27R+N233C+D254S, D27R+N233C+P256T, D27R+D254S+P256T, N33K+G38A+F51V, N33K+G38A+E56K, N33K+G38A+L69R, N33K+G38A+D96E, N33K+G38A+K98I, N33K+G38A+D111A, N33K+G38A+G163K, N33K+G38A+V176L, N33K+G38A+H198S, N33K+G38A+E210K, N33K+G38A+Y220F, N33K+G38A+L227G, N33K+G38A+T231R, N33K+G38A+N233R, N33K+G38A+N233C, N33K+G38A+D254S, N33K+G38A+P256T, N33K+F51V+E56K, N33K+F51V+L69R, N33K+F51V+D96E, N33K+F51V+K98I, N33K+F51V+D111A, N33K+F51V+G163K, N33K+F51V+V176L, N33K+F51V+H198S, N33K+F51V+E210K, N33K+F51V+Y220F, N33K+F51V+L227G, N33K+F51V+T231R, N33K+F51V+N233R, N33K+F51V+N233C, N33K+F51V+D254S, N33K+F51V+P256T, N33K+E56K+L69R, N33K+E56K+D96E, N33K+E56K+K98I, N33K+E56K+D111A, N33K+E56K+G163K, N33K+E56K+V176L, N33K+E56K+H198S, N33K+E56K+E210K, N33K+E56K+Y220F, N33K+E56K+L227G, N33K+E56K+T231R, N33K+E56K+N233R, N33K+E56K+N233C, N33K+E56K+D254S, N33K+E56K+P256T, N33K+L69R+D96E, N33K+L69R+K98I, N33K+L69R+D111A, N33K+L69R+G163K, N33K+L69R+V176L, N33K+L69R+H198S, N33K+L69R+E210K, N33K+L69R+Y220F, N33K+L69R+L227G, N33K+L69R+T231R, N33K+L69R+N233R, N33K+L69R+N233C, N33K+L69R+D254S, N33K+L69R+P256T, N33K+D96E+K98I, N33K+D96E+D111A, N33K+D96E+G163K, N33K+D96E+V176L, N33K+D96E+H198S, N33K+D96E+E210K, N33K+D96E+Y220F, N33K+D96E+L227G, N33K+D96E+T231R, N33K+D96E+N233R, N33K+D96E+N233C, N33K+D96E+D254S, N33K+D96E+P256T, N33K+K98I+D111A, N33K+K98I+G163K, N33K+K98I+V176L, N33K+K98I+H198S, N33K+K98I+E210K, N33K+K98I+Y220F, N33K+K98I+L227G, N33K+K98I+T231R, N33K+K98I+N233R, N33K+K98I+N233C, N33K+K98I+D254S, N33K+K98I+P256T, N33K+D111A+G163K, N33K+D111A+V176L, N33K+D111A+H198S, N33K+D111A+E210K, N33K+D111A+Y220F, N33K+D111A+L227G, N33K+D111A+T231R, N33K+D111A+N233R, N33K+D111A+N233C, N33K+D111A+D254S, N33K+D111A+P256T, N33K+G163K+V176L, N33K+G163K+H198S, N33K+G163K+E210K, N33K+G163K+Y220F, N33K+G163K+L227G, N33K+G163K+T231R, N33K+G163K+N233R, N33K+G163K+N233C, N33K+G163K+D254S, N33K+G163K+P256T, N33K+V176L+H198S, N33K+V176L+E210K, N33K+V176L+Y220F, N33K+V176L+L227G, N33K+V176L+T231R, N33K+V176L+N233R, N33K+V176L+N233C, N33K+V176L+D254S, N33K+V176L+P256T, N33K+H198S+E210K, N33K+H198S+Y220F, N33K+H198S+L227G, N33K+H198S+T231R, N33K+H198S+N233R, N33K+H198S+N233C, N33K+H198S+D254S, N33K+H198S+P256T, N33K+E210K+Y220F, N33K+E210K+L227G, N33K+E210K+T231R, N33K+E210K+N233R, N33K+E210K+N233C, N33K+E210K+D254S, N33K+E210K+P256T, N33K+Y220F+L227G, N33K+Y220F+T231R, N33K+Y220F+N233R, N33K+Y220F+N233C, N33K+Y220F+D254S, N33K+Y220F+P256T, N33K+L227G+T231R, N33K+L227G+N233R, N33K+L227G+N233C, N33K+L227G+D254S, N33K+L227G+P256T, N33K+T231R+N233R, N33K+T231R+N233C, N33K+T231R+D254S, N33K+T231R+P256T, N33K+N233R+N233C, N33K+N233R+D254S, N33K+N233R+P256T, N33K+N233C+D254S, N33K+N233C+P256T, N33K+D254S+P256T, G38A+F51V+E56K, G38A+F51V+L69R, G38A+F51V+D96E, G38A+F51V+K98I, G38A+F51V+D111A, G38A+F51V+G163K, G38A+F51V+V176L, G38A+F51V+H198S, G38A+F51V+E210K, G38A+F51V+Y220F, G38A+F51V+L227G, G38A+F51V+T231R, G38A+F51V+N233R, G38A+F51V+N233C, G38A+F51V+D254S, G38A+F51V+P256T, G38A+E56K+L69R, G38A+E56K+D96E, G38A+E56K+K98I, G38A+E56K+D111A, G38A+E56K+G163K, G38A+E56K+V176L, G38A+E56K+H198S, G38A+E56K+E210K, G38A+E56K+Y220F, G38A+E56K+L227G, G38A+E56K+T231R, G38A+E56K+N233R, G38A+E56K+N233C, G38A+E56K+D254S, G38A+E56K+P256T, G38A+L69R+D96E, G38A+L69R+K98I, G38A+L69R+D111A, G38A+L69R+G163K, G38A+L69R+V176L, G38A+L69R+H198S, G38A+L69R+E210K, G38A+L69R+Y220F, G38A+L69R+L227G, G38A+L69R+T231R, G38A+L69R+N233R, G38A+L69R+N233C, G38A+L69R+D254S, G38A+L69R+P256T, G38A+D96E+K98I, G38A+D96E+D111A, G38A+D96E+G163K, G38A+D96E+V176L, G38A+D96E+H198S, G38A+D96E+E210K, G38A+D96E+Y220F, G38A+D96E+L227G, G38A+D96E+T231R, G38A+D96E+N233R, G38A+D96E+N233C, G38A+D96E+D254S, G38A+D96E+P256T, G38A+K98I+D111A, G38A+K98I+G163K, G38A+

K98I+V176L, G38A+K98I+H198S, G38A+K98I+E210K, G38A+K98I+Y220F, G38A+K98I+L227G, G38A+K98I+T231R, G38A+K98I+N233R, G38A+K98I+N233C, G38A+K98I+D254S, G38A+K98I+P256T, G38A+D111A+G163K, G38A+D111A+V176L, G38A+D111A+H198S, G38A+D111A+E210K, G38A+D111A+Y220F, G38A+D111A+L227G, G38A+D111A+T231R, G38A+D111A+N233R, G38A+D111A+N233C, G38A+D111A+D254S, G38A+D111A+P256T, G38A+G163K+V176L, G38A+G163K+H198S, G38A+G163K+E210K, G38A+G163K+Y220F, G38A+G163K+L227G, G38A+G163K+T231R, G38A+G163K+N233R, G38A+G163K+N233C, G38A+G163K+D254S, G38A+G163K+P256T, G38A+V176L+H198S, G38A+V176L+E210K, G38A+V176L+Y220F, G38A+V176L+L227G, G38A+V176L+T231R, G38A+V176L+N233R, G38A+V176L+N233C, G38A+V176L+D254S, G38A+V176L+P256T, G38A+H198S+E210K, G38A+H198S+Y220F, G38A+H198S+L227G, G38A+H198S+T231R, G38A+H198S+N233R, G38A+H198S+N233C, G38A+H198S+D254S, G38A+H198S+P256T, G38A+E210K+Y220F, G38A+E210K+L227G, G38A+E210K+T231R, G38A+E210K+N233R, G38A+E210K+N233C, G38A+E210K+D254S, G38A+E210K+P256T, G38A+Y220F+L227G, G38A+Y220F+T231R, G38A+Y220F+N233R, G38A+Y220F+N233C, G38A+Y220F+D254S, G38A+Y220F+P256T, G38A+L227G+T231R, G38A+L227G+N233R, G38A+L227G+N233C, G38A+L227G+D254S, G38A+L227G+P256T, G38A+T231R+N233R, G38A+T231R+N233C, G38A+T231R+D254S, G38A+T231R+P256T, G38A+N233R+N233C, G38A+N233R+D254S, G38A+N233R+P256T G38A+N233C+D254S, G38A+N233C+P256T, G38A+D254S+P256T, F51V+E56K+L69R, F51V+E56K+D96E, F51V+E56K+K98I, F51V+E56K+D111A, F51V+E56K+G163K, F51V+E56K+V176L, F51V+E56K+H198S, F51V+E56K+E210K, F51V+E56K+Y220F, F51V+E56K+L227G, F51V+E56K+T231R, F51V+E56K+N233R, F51V+E56K+N233C, F51V+E56K+D254S, F51V+E56K+P256T, F51V+L69R+D96E, F51V+L69R+K98I, F51V+L69R+D111A, F51V+L69R+G163K, F51V+L69R+V176L, F51V+L69R+H198S, F51V+L69R+E210K, F51V+L69R+Y220F, F51V+L69R+L227G, F51V+L69R+T231R, F51V+L69R+N233R, F51V+L69R+N233C, F51V+L69R+D254S, F51V+L69R+P256T, F51V+D96E+K98I, F51V+D96E+D111A, F51V+D96E+G163K, F51V+D96E+V176L, F51V+D96E+H198S, F51V+D96E+E210K, F51V+D96E+Y220F, F51V+D96E+L227G, F51V+D96E+T231R, F51V+D96E+N233R, F51V+D96E+N233C, F51V+D96E+D254S, F51V+D96E+P256T, F51V+K98I+D111A, F51V+K98I+G163K, F51V+K98I+V176L, F51V+K98I+H198S, F51V+K98I+E210K, F51V+K98I+Y220F, F51V+K98I+L227G, F51V+K98I+T231R, F51V+K98I+N233R, F51V+K98I+N233C, F51V+K98I+D254S, F51V+K98I+P256T, F51V+D111A+G163K, F51V+D111A+V176L, F51V+D111A+H198S, F51V+D111A+E210K, F51V+D111A+Y220F, F51V+D111A+L227G, F51V+D111A+T231R, F51V+D111A+N233R, F51V+D111A+N233C, F51V+D111A+D254S, F51V+D111A+P256T, F51V+G163K+V176L, F51V+G163K+H198S, F51V+G163K+E210K, F51V+G163K+Y220F, F51V+G163K+L227G, F51V+G163K+T231R, F51V+G163K+N233R, F51V+G163K+N233C, F51V+G163K+D254S, F51V+G163K+P256T, F51V+V176L+H198S, F51V+V176L+E210K, F51V+V176L+Y220F, F51V+V176L+L227G, F51V+V176L+T231R, F51V+V176L+N233R, F51V+V176L+N233C, F51V+V176L+D254S, F51V+V176L+P256T, F51V+H198S+E210K, F51V+H198S+Y220F, F51V+H198S+L227G, F51V+H198S+

T231R, F51V+H198S+N233R, F51V+H198S+N233C, F51V+H198S+D254S, F51V+H198S+P256T, F51V+E210K+Y220F, F51V+E210K+L227G, F51V+E210K+T231R, F51V+E210K+N233R, F51V+E210K+N233C, F51V+E210K+D254S, F51V+E210K+P256T, F51V+Y220F+L227G, F51V+Y220F+T231R, F51V+Y220F+N233R, F51V+Y220F+N233C, F51V+Y220F+D254S, F51V+Y220F+P256T, F51V+L227G+T231R, F51V+L227G+N233R, F51V+L227G+N233C, F51V+L227G+D254S, F51V+L227G+P256T, F51V+T231R+N233R, F51V+T231R+N233C, F51V+T231R+D254S, F51V+T231R+P256T, F51V+N233R+N233C, F51V+N233R+D254S, F51V+N233R+P256T, F51V+N233C+D254S, F51V+N233C+P256T, F51V+D254S+P256T, E56K+L69R+D96E, E56K+L69R+K98I, E56K+L69R+D111A, E56K+L69R+G163K, E56K+L69R+V176L, E56K+L69R+H198S, E56K+L69R+E210K, E56K+L69R+Y220F, E56K+L69R+L227G, E56K+L69R+T231R, E56K+L69R+N233R, E56K+L69R+N233C, E56K+L69R+D254S, E56K+L69R+P256T, E56K+D96E+K98I, E56K+D96E+D111A, E56K+D96E+G163K, E56K+D96E+V176L, E56K+D96E+H198S, E56K+D96E+E210K, E56K+D96E+Y220F, E56K+D96E+L227G, E56K+D96E+T231R, E56K+D96E+N233R, E56K+D96E+N233C, E56K+D96E+D254S, E56K+D96E+P256T, E56K+K98I+D111A, E56K+K98I+G163K, E56K+K98I+V176L, E56K+K98I+H198S, E56K+K98I+E210K, E56K+K98I+Y220F, E56K+K98I+L227G, E56K+K98I+T231R, E56K+K98I+N233R, E56K+K98I+N233C, E56K+K98I+D254S, E56K+K98I+P256T, E56K+D111A+G163K, E56K+D111A+V176L, E56K+D111A+H198S, E56K+D111A+E210K, E56K+D111A+Y220F, E56K+D111A+L227G, E56K+D111A+T231R, E56K+D111A+N233R, E56K+D111A+N233C, E56K+D111A+D254S, E56K+D111A+P256T, E56K+G163K+V176L, E56K+G163K+H198S, E56K+G163K+E210K, E56K+G163K+Y220F, E56K+G163K+L227G, E56K+G163K+T231R, E56K+G163K+N233R, E56K+G163K+N233C, E56K+G163K+D254S, E56K+G163K+P256T, E56K+V176L+H198S, E56K+V176L+E210K, E56K+V176L+Y220F, E56K+V176L+L227G, E56K+V176L+T231R, E56K+V176L+N233R, E56K+V176L+N233C, E56K+V176L+D254S, E56K+V176L+P256T, E56K+H198S+E210K, E56K+H198S+Y220F, E56K+H198S+L227G, E56K+H198S+T231R, E56K+H198S+N233R, E56K+H198S+N233C, E56K+H198S+D254S, E56K+H198S+P256T, E56K+E210K+Y220F, E56K+E210K+L227G, E56K+E210K+T231R, E56K+E210K+N233R, E56K+E210K+N233C, E56K+E210K+D254S, E56K+E210K+P256T, E56K+Y220F+L227G, E56K+Y220F+T231R, E56K+Y220F+N233R, E56K+Y220F+N233C, E56K+Y220F+D254S, E56K+Y220F+P256T, E56K+L227G+T231R, E56K+L227G+N233R, E56K+L227G+N233C, E56K+L227G+D254S, E56K+L227G+P256T, E56K+T231R+N233R, E56K+T231R+N233C, E56K+T231R+D254S, E56K+T231R+P256T, E56K+N233R+N233C, E56K+N233R+D254S, E56K+N233R+P256T, E56K+N233C+D254S, E56K+N233C+P256T, E56K+D254S+P256T, L69R+D96E+K98I, L69R+D96E+D111A, L69R+D96E+G163K, L69R+D96E+V176L, L69R+D96E+H198S, L69R+D96E+E210K, L69R+D96E+Y220F, L69R+D96E+L227G, L69R+D96E+T231R, L69R+D96E+N233R, L69R+D96E+N233C, L69R+D96E+D254S, L69R+D96E+P256T, L69R+K98I+D111A, L69R+K98I+G163K, L69R+K98I+V176L, L69R+K98I+H198S, L69R+K98I+E210K, L69R+K98I+Y220F, L69R+K98I+L227G, L69R+K98I+T231R, L69R+K98I+N233R, L69R+K98I+N233C, L69R+K98I+D254S, L69R+K98I+P256T, L69R+D111A+G163K,

L69R+D111A+V176L, L69R+D111A+H198S, L69R+D111A+E210K, L69R+D111A+Y220F, L69R+D111A+L227G, L69R+D111A+T231R, L69R+D111A+N233R, L69R+D111A+N233C, L69R+D111A+D254S, L69R+D111A+P256T, L69R+G163K+V176L, L69R+G163K+H198S, L69R+G163K+E210K, L69R+G163K+Y220F, L69R+G163K+L227G, L69R+G163K+T231R, L69R+G163K+N233R, L69R+G163K+N233C, L69R+G163K+D254S, L69R+G163K+P256T, L69R+V176L+H198S, L69R+V176L+E210K, L69R+V176L+Y220F, L69R+V176L+L227G, L69R+V176L+T231R, L69R+V176L+N233R, L69R+V176L+N233C, L69R+V176L+D254S, L69R+V176L+P256T, L69R+H198S+E210K, L69R+H198S+Y220F, L69R+H198S+L227G, L69R+H198S+T231R, L69R+H198S+N233R, L69R+H198S+N233C, L69R+H198S+D254S, L69R+H198S+P256T, L69R+E210K+Y220F, L69R+E210K+L227G, L69R+E210K+T231R, L69R+E210K+N233R, L69R+E210K+N233C, L69R+E210K+D254S, L69R+E210K+P256T, L69R+Y220F+L227G, L69R+Y220F+T231R, L69R+Y220F+N233R, L69R+Y220F+N233C, L69R+Y220F+D254S, L69R+Y220F+P256T, L69R+L227G+T231R, L69R+L227G+N233R, L69R+L227G+N233C, L69R+L227G+D254S, L69R+L227G+P256T, L69R+T231R+N233R, L69R+T231R+N233C, L69R+T231R+D254S, L69R+T231R+P256T, L69R+N233R+N233C, L69R+N233R+D254S, L69R+N233R+P256T, L69R+N233C+D254S, L69R+N233C+P256T, L69R+D254S+P256T, D96E+K98I+D111A, 96E+K98I+G163K, D96E+K98I+V176L, D96E+K98I+H198S, D96E+K98I+E210K, D96E+K98I+Y220F, D96E+K98I+L227G, D96E+K98I+T231R, D96E+K98I+N233R, D96E+K98I+N233C, D96E+K98I+D254S, D96E+K98I+P256T, D96E+D111A+G163K, D96E+D111A+V176L, D96E+D111A+H198S, D96E+D111A+E210K, D96E+D111A+Y220F, D96E+D111A+L227G, D96E+D111A+T231R, D96E+D111A+N233R, D96E+D111A+N233C, D96E+D111A+D254S, D96E+D111A+P256T, D96E+G163K+V176L, D96E+G163K+H198S, D96E+G163K+E210K, D96E+G163K+Y220F, D96E+G163K+L227G, D96E+G163K+T231R, D96E+G163K+N233R, D96E+G163K+N233C, D96E+G163K+D254S, D96E+G163K+P256T, D96E+V176L+H198S, D96E+V176L+E210K, D96E+V176L+Y220F, D96E+V176L+L227G, D96E+V176L+T231R, D96E+V176L+N233R, D96E+V176L+N233C, D96E+V176L+D254S, D96E+V176L+P256T, D96E+H198S+E210K, D96E+H198S+Y220F, D96E+H198S+L227G, D96E+H198S+T231R, D96E+H198S+N233R, D96E+H198S+N233C, D96E+H198S+D254S, D96E+H198S+P256T, D96E+E210K+Y220F, D96E+E210K+L227G, D96E+E210K+T231R, D96E+E210K+N233R, D96E+E210K+N233C, D96E+E210K+D254S, D96E+E210K+P256T, D96E+Y220F+L227G, D96E+Y220F+T231R, D96E+Y220F+N233R, D96E+Y220F+N233C, D96E+Y220F+D254S, D96E+Y220F+P256T, D96E+L227G+T231R, D96E+L227G+N233R, D96E+L227G+N233C, D96E+L227G+D254S, D96E+L227G+P256T, D96E+T231R+N233R, D96E+T231R+N233C, D96E+T231R+D254S, D96E+T231R+P256T, D96E+N233R+N233C, D96E+N233R+D254S, D96E+N233R+P256T, D96E+N233C+D254S, D96E+N233C+P256T D96E+D254S+P256T, K98I+D111A+G163K, K98I+D111A+V176L, K98I+D111A+H198S, K98I+D111A+E210K, K98I+D111A+Y220F, K98I+D111A+L227G, K98I+D111A+T231R, K98I+D111A+N233R, K98I+D111A+N233C, K98I+D111A+D254S, K98I+D111A+P256T, K98I+G163K+V176L, K98I+G163K+H198S, K98I+G163K+E210K, K98I+G163K+Y220F, K98I+G163K+L227G, K98I+G163K+T231R, K98I+G163K+N233R, K98I+G163K+N233C, K98I+G163K+D254S, K98I+G163K+P256T, K98I+V176L+H198S, K98I+V176L+E210K, K98I+V176L+Y220F, K98I+V176L+L227G, K98I+V176L+T231R, K98I+V176L+N233R, K98I+V176L+N233C, K98I+V176L+D254S, K98I+V176L+P256T, K98I+H198S+E210K, K98I+H198S+Y220F, K98I+H198S+L227G, K98I+H198S+T231R, K98I+H198S+N233R, K98I+H198S+N233C, K98I+H198S+D254S, K98I+H198S+P256T, K98I+E210K+Y220F, K98I+E210K+L227G, K98I+E210K+T231R, K98I+E210K+N233R, K98I+E210K+N233C, K98I+E210K+D254S, K98I+E210K+P256T, K98I+Y220F+L227G, K98I+Y220F+T231R, K98I+Y220F+N233R, K98I+Y220F+N233C, K98I+Y220F+D254S, K98I+Y220F+P256T, K98I+L227G+T231R, K98I+L227G+N233R, K98I+L227G+N233C, K98I+L227G+D254S, K98I+L227G+P256T, K98I+T231R+N233R, K98I+T231R+N233C, K98I+T231R+D254S, K98I+T231R+P256T, K98I+N233R+N233C, K98I+N233R+D254S, K98I+N233R+P256T, K98I+N233C+D254S, K98I+N233C+P256T, K98I+D254S+P256T, D111A+G163K+V176L, D111A+G163K+H198S, D111A+G163K+E210K, D111A+G163K+Y220F, D111A+G163K+L227G, D111A+G163K+T231R, D111A+G163K+N233R, D111A+G163K+N233C, D111A+G163K+D254S, D111A+G163K+P256T, D111A+V176L+H198S, D111A+V176L+E210K, D111A+V176L+Y220F, D111A+V176L+L227G, D111A+V176L+T231R, D111A+V176L+N233R, D111A+V176L+N233C, D111A+V176L+D254S, D111A+V176L+P256T, D111A+H198S+E210K, D111A+H198S+Y220F, D111A+H198S+L227G, D111A+H198S+T231R, D111A+H198S+N233R, D111A+H198S+N233C, D111A+H198S+D254S, D111A+H198S+P256T, D111A+E210K+Y220F, D111A+E210K+L227G, D111A+E210K+T231R, D111A+E210K+N233R, D111A+E210K+N233C, D111A+E210K+D254S, D111A+E210K+P256T, D111A+Y220F+L227G, D111A+Y220F+T231R, D111A+Y220F+N233R, D111A+Y220F+N233C, D111A+Y220F+D254S, D111A+Y220F+P256T, D111A+L227G+T231R, D111A+L227G+N233R, D111A+L227G+N233C, D111A+L227G+D254S, D111A+L227G+P256T, D111A+T231R+N233R, D111A+T231R+N233C, D111A+T231R+D254S, D111A+T231R+P256T, D111A+N233R+N233C, D111A+N233R+D254S, D111A+N233R+P256T, D111A+N233C+D254S, D111A+N233C+P256T, D111A+D254S+P256T, G163K+V176L+H198S, G163K+V176L+E210K, G163K+V176L+Y220F, G163K+V176L+L227G, G163K+V176L+T231R, G163K+V176L+N233R, G163K+V176L+N233C, G163K+V176L+D254S, G163K+V176L+P256T, G163K+H198S+E210K, G163K+H198S+Y220F, G163K+H198S+L227G, G163K+H198S+T231R, G163K+H198S+N233R, G163K+H198S+N233C, G163K+H198S+D254S, G163K+H198S+P256T, G163K+E210K+Y220F, G163K+E210K+L227G, G163K+E210K+T231R, G163K+E210K+N233R, G163K+E210K+N233C, G163K+E210K+D254S, G163K+E210K+P256T, G163K+Y220F+L227G, G163K+Y220F+T231R, G163K+Y220F+N233R, G163K+Y220F+N233C, G163K+Y220F+D254S, G163K+Y220F+P256T, G163K+L227G+T231R, G163K+L227G+N233R, G163K+L227G+N233C, G163K+L227G+D254S, G163K+L227G+P256T, G163K+T231R+N233R, G163K+T231R+N233C, G163K+T231R+D254S, G163K+T231R+P256T, G163K+N233R+N233C, G163K+N233R+D254S, G163K+N233R+P256T, G163K+N233C+D254S, G163K+N233C+P256T, G163K+D254S+P256T, V176L+H198S+E210K, V176L+H198S+Y220F, V176L+H198S+L227G, V176L+H198S+T231R, V176L+H198S+N233R, V176L+

H198S+N233C, V176L+H198S+D254S, V176L+H198S+P256T, V176L+E210K+Y220F, V176L+E210K+L227G, V176L+E210K+T231R, V176L+E210K+N233R, V176L+E210K+N233C, V176L+E210K+D254S, V176L+E210K+P256T, V176L+Y220F+L227G, V176L+Y220F+T231R, V176L+Y220F+N233R, V176L+Y220F+N233C, V176L+Y220F+D254S, V176L+Y220F+P256T, V176L+L227G+T231R, V176L+L227G+N233R, V176L+L227G+N233C, V176L+L227G+D254S, V176L+L227G+P256T, V176L+T231R+N233R, V176L+T231R+N233C, V176L+T231R+D254S, V176L+T231R+P256T, V176L+N233R+N233C, V176L+N233R+D254S, V176L+N233R+P256T, V176L+N233C+D254S, V176L+N233C+P256T, V176L+D254S+P256T, H198S+E210K+Y220F, H198S+E210K+L227G, H198S+E210K+T231R, H198S+E210K+N233R, H198S+E210K+N233C, H198S+E210K+D254S, H198S+E210K+P256T, H198S+Y220F+L227G, H198S+Y220F+T231R, H198S+Y220F+N233R, H198S+Y220F+N233C, H198S+Y220F+D254S, H198S+Y220F+P256T, H198S+L227G+T231R, H198S+L227G+N233R, H198S+L227G+N233C, H198S+L227G+D254S, H198S+L227G+P256T, H198S+T231R+N233R, H198S+T231R+N233C, H198S+T231R+D254S, H198S+T231R+P256T, H198S+N233R+N233C, H198S+N233R+D254S, H198S+N233R+P256T, H198S+N233C+D254S, H198S+N233C+P256T, H198S+D254S+P256T, E210K+Y220F+L227G, E210K+Y220F+T231R, E210K+Y220F+N233R, E210K+Y220F+N233C, E210K+Y220F+D254S, E210K+Y220F+P256T, E210K+L227G+T231R, E210K+L227G+N233R, E210K+L227G+N233C, E210K+L227G+D254S, E210K+L227G+P256T, E210K+T231R+N233R, E210K+T231R+N233C, E210K+T231R+D254S, E210K+T231R+P256T, E210K+N233R+N233C, E210K+N233R+D254S, E210K+N233R+P256T, E210K+N233C+D254S, E210K+N233C+P256T, E210K+D254S+P256T, Y220F+L227G+T231R, Y220F+L227G+N233R, Y220F+L227G+N233C, Y220F+L227G+D254S, Y220F+L227G+P256T, Y220F+T231R+N233R, Y220F+T231R+N233C, Y220F+T231R+D254S, Y220F+T231R+P256T, Y220F+N233R+N233C, Y220F+N233R+D254S, Y220F+N233R+P256T, Y220F+N233C+D254S, Y220F+N233C+P256T, Y220F+D254S+P256T, L227G+T231R+N233R, L227G+T231R+N233C, L227G+T231R+D254S, L227G+T231R+P256T, L227G+N233R+N233C, L227G+N233R+D254S, L227G+N233R+P256T, L227G+N233C+D254S, L227G+N233C+P256T, L227G+D254S+P256T, T231R+N233R+N233C, T231R+N233R+D254S, T231R+N233R+P256T, T231R+N233C+D254S, T231R+N233C+P256T, T231R+D254S+P256T, N233R+N233C+D254S, N233R+N233C+P256T, N233R+D254S+P256T, and N233C+D254S+P256T, wherein numbering is according to SEQ ID NO: 1.

In a preferred embodiment the lipase variant comprises one of the following set of substitutions using SEQ ID NO: 1 for numbering:

| |
|---|
| E1C + H198L + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + H198Y + N233C |
| E1C + H198T + N233C |
| E1C + H198G + N233C |
| E1C + L227F + N233C |
| E1C + L227R + N233C |
| E1C + E210T + N233C |
| E1C + E210N + N233C |
| E1C + V176M + N233C |
| E1C + K98T + N233C |
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |
| E1C + V2I + N233C |
| E1C + V2N + N233C |
| E1C + V2K + N233C |
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + T231R + N233C |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + E210A + N233C |
| E1C + E210Q + N233C |
| E1C + E210R + N233C |
| E1C + H198D + N233C |
| E1C + K98R + N233C |
| E1C + K98V + N233C |
| E1C + F51L + N233C |

-continued

| |
|---|
| E1C + F51I + N233C |
| E1C + K237C |
| E1C + L227G + N233C |
| E1C + E210K + N233C |
| E1C + V176L + N233C |
| E1C + K98Q + N233C |
| E1C + E56K + N233C |
| E1C + L147S + N233C + D254S |
| E1C + Y220F + N233C |
| E1C + K98I + N233C |
| E1C + D27R + F51I + E56R + K98E + T231R + N233C |
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + F51L + D96E + K98I + D111A + G163S + H198S + Y220F + T231R + N233C + P256T |
| E1C + D27R + F51L + D96E + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + P256T |
| E1C + D27R + F51V + D96E + K98I + D111A + G163K + H198S + Y220F + T231R + N233C + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96E + K98I + D111A + G163S + H198S + Y220F + T231R + N233C + P256T |
| E1C + F51L + D96E + K98I + D111A + G163K + H198S + Y220F + T231R + N233C + D254S + P256T |
| E1C + G38A + F51V + D96E + K98I + D111A + G163K + H198S + Y220F + T231R + N233C + P256T |
| E1C + F51V + D96E + K98I + D111A + G163K + H198S + Y220F + T231R + N233C + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + D27R + N33K + G38A + F51V + D96E + K98I + D111A + G163K + H198S + Y220F + T231R + N233C |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

In one embodiment, the lipase variant comprised in a composition of the invention further comprises one of the substitutions selected from the group of: S54T, S83T, G91A, A150G, I255A, and E239C.

In one embodiment, the parent lipase is a lipase having at least 70%, such as at least 75%, such as at least 80%, such as at least 85%, such as at least 90%, such as at least 95%, such as at least 97%, such as at least 99% such as 100% sequence identity to the amino acid sequence of SEQ ID NO: 1.

In one embodiment, the parent lipase comprises an amino acid sequence of at least 70%, such as at least 75%, such as at least 80%, such as at least 85%, such as at least 90%, such as at least 95%, such as at least 97%, such as at least 99%, such as 100% sequence identity to the amino acid sequence of SEQ ID NO: 1.

In one embodiment, the parent lipase consists of the amino acid sequence of SEQ ID NO: 1.

Composition of the Invention Comprising One or More Surfactants

Detergent composition A. In an embodiment the composition of the invention comprises a lipase variant of the invention and linear alkylbenzene sulfonate (LAS). In the wash solution the linear alkylbenzene sulfonate (LAS) may be present in a concentration of 0.1-10 mM, such 1-5 mM, such as 2 mM. According to the invention the lipase activity in the wash solution is increased in comparison to the parent, in particular SEQ ID NO: 1 (LIPOLASE™) (see Example 4). In a preferred embodiment the composition comprises the following lipase variants:

| |
|---|
| E1C + H198T + N233C |
| E1C + H198G + N233C |
| E1C + L227F + N233C |
| E1C + E210T + N233C |
| E1C + E210N + N233C |
| E1C + V176M + N233C |
| E1C + K98T + N233C |
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |
| E1C + V2I + N233C |
| E1C + V2N + N233C |
| E1C + V2K + N233C |

-continued

| |
|---|
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + V176L + N233C |
| E1C + E56K + N233C |
| E1C + E210A + N233C |
| E1C + E210Q + N233C |
| E1C + E210R + N233C |
| E1C + K98R + N233C |
| E1C + K98V + N233C |
| E1C + F51L + N233C |
| E1C + F51I + N233C |
| E1C + L227G + N233C |
| E1C + E210K + N233C |
| E1C + K98Q + N233C |
| E1C + Y220F + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + K237C |
| E1C + K98I + N233C |
| E1C + D27R + F51I + E56R + K98E + T231R + N233C |
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |

Detergent composition B. In an embodiment the composition of the invention comprises a lipase variant of the invention and an alcohol ether sulfate (AEOS). In the wash solution the alcohol ether sulfate (AEOS) may be present in a concentration of 0.1-10 mM, such 1-5 mM, such as 2 mM. According to the invention the lipase activity in the wash solution is increased in comparison to the parent, in particular SEQ ID NO: 1 (LIPOLASE™) (see Example 4). In a preferred embodiment the composition comprises one of the following set of substitutions:

| |
|---|
| E1C H198Y N233C |
| E1C H198T N233C |
| E1C H198G N233C |
| E1C H198S N233C |
| E1C H198L N233C |
| E1C H198G N233C |

Detergent composition C. In an embodiment the composition of the invention comprises a lipase variant of the invention and linear alkylbenzene sulfonate (LAS) and alcohol ethoxylate (AEO). In an embodiment the ratio between the surfactants may be 3:1, 2:1, 1:1, such as in the range from 10:1 to 1:10, such as 5:1 to 1:5, or 3:1 to 1:3. In a preferred embodiment the ratio is 2:1. In an embodiment the total surfactant concentration in the wash solution is from 0.1 to 15 mW such as 0.5-10 mW in particular from 1-5 mM. In the wash solution the linear alkylbenzene sulfonate (LAS) may be present in a concentration of 0.1-10 mW such 1-5 mW such as 2 mM. In an embodiment alcohol ethoxylate (AEO) is present in the wash solution in a concentration of 0.05-5 mM, such 0.5-3 mM, such as 1 mM. According to the invention the lipase activity in the wash solution is increased in comparison to the parent, in particular SEQ ID NO: 1 (LIPOLASE™) (see Example 4). In a preferred embodiment the composition comprises one of the following set of substitutions:

| |
|---|
| E1C + H198Y + N233C |
| E1C + H198T + N233C |
| E1C + H198G + N233C |
| E1C + L227F + N233C |
| E1C + L227R + N233C |
| E1C + E210T + N233C |
| E1C + E210N + N233C |
| E1C + V176M + N233C |
| E1C + K98T + N233C |
| E1C + K98E + N233C |
| E1C + E56S + N233C |
| E1C + E56Q + N233C |
| E1C + E56R + N233C |

-continued

| |
|---|
| E1C + F51M + N233C |
| E1C + D27R + F51Y + N233C |
| E1C + V2I + N233C |
| E1C + V2N + N233C |
| E1C + V2K + N233C |
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + T231R + N233C |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + V176L + N233C |
| E1C + E56K + N233C |
| E1C + E210A + N233C |
| E1C + E210Q + N233C |
| E1C + E210R + N233C |
| E1C + H198D + N233C |
| E1C + K98R + N233C |
| E1C + K98V + N233C |
| E1C + F51L + N233C |
| E1C + F51I + N233C |
| E1C + L227G + N233C |
| E1C + E210K + N233C |
| E1C + K98Q + N233C |
| E1C + Y220F + N233C |
| E1C + H198L + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + K237C |
| E1C + K98I + N233C |
| E1C + D27R + F51I + E56R + K98E + T231R + N233C |
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + F51L + D96E + K98I + D111A + G163S + H198S + Y220F + T231R + N233C + P256T |
| E1C + D27R + F51L + D96E + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + P256T |
| E1C + D27R + F51V + D96E + K98I + D111A + G163K + H198S + Y220F + T231R + N233C + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96E + K98I + D111A + G163S + H198S + Y220F + T231R + N233C + P256T |
| E1C + G38A + F51V + D96E + K98I + D111A + G163K + H198S + Y220F + T231R + N233C + P256T |
| E1C + F51V + D96E + K98I + D111A + G163K + H198S + Y220F + T231R + N233C + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + D27R + N33K + G38A + F51V + D96E + K98I + D111A + G163K + H198S + Y220F + T231R + N233C |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

Detergent composition D. In an embodiment the composition of the invention comprises a lipase variant of the invention and linear alkylbenzene sulfonate (LAS) and alcohol ethoxylate (AEO). In an embodiment the ratio between the surfactants may be 3:1, 2:1, 1:1, such as in the range from 10:1 to 1:10, such as 5:1 to 1:5, or 3:1 to 1:3. In a preferred embodiment the ratio is 2:1. In an embodiment the total surfactant concentration in the wash solution is from 0.01 to 1.5 mW such as 0.05-1.0 mM, in particular from 0.1-0.5 mM. In the wash solution linear alkylbenzene sulfonate (LAS) may be present in a concentration of 0.01-1.0 mM, such 0.1-0.5 mM, such as 0.2 mM. In an embodiment alcohol ethoxylate (AEO) may be present in the wash solution in a concentration of 0.005-0.5 mW such 0.05-0.3 mW such as 0.1 mM. According to the invention the lipase activity in the wash solution is increased in comparison to the parent lipase, in particular SEQ ID NO: 1 (LIPOLASE™) (see Example 4). In a preferred embodiment the composition comprises one of the following set of substitutions using SEQ ID NO: 1 for numbering:

| |
|---|
| E1C + H198Y + N233C |
| E1C + H198T + N233C |
| E1C + H198G + N233C |
| E1C + L227F + N233C |
| E1C + E210T + N233C |
| E1C + E210N + N233C |
| E1C + V176M + N233C |
| E1C + K98T + N233C |
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |
| E1C + V2I + N233C |
| E1C + V2N + N233C |
| E1C + V2K + N233C |
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + T231R + N233C |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + V176L + N233C |
| E1C + E56K + N233C |
| E1C + E210A + N233C |
| E1C + E210Q + N233C |
| E1C + E210R + N233C |
| E1C + K98R + N233C |
| E1C + K98V + N233C |
| E1C + F51L + N233C |
| E1C + F51I + N233C |
| E1C + L227G + N233C |
| E1C + E210K + N233C |
| E1C + K98Q + N233C |
| E1C + Y220F + N233C |
| E1C + H198L + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + K237C |
| E1C + K98I + N233C |
| E1C + D27R + F51I + E56R + K98E + T231R + N233C |
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + F51L + D96E + K98I + D111A + G163S + H198S + Y220F + T231R + N233C + P256T |
| E1C + D27R + F51L + D96E + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + P256T |
| E1C + D27R + F51V + D96E + K98I + D111A + G163K + H198S + Y220F + T231R + N233C + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |

-continued

| |
|---|
| E1C + D27R + G38A + F51V + D96E + K98I + D111A + G163K + H198S + Y220F + T231R + N233C + D254S + P256T |
| E1C + F51V + D96E + K98I + D111A + G163S + H198S + Y220F + T231R + N233C + P256T |
| E1C + G38A + F51V + D96E + K98I + D111A + G163K + H198S + Y220F + T231R + N233C + P256T |
| E1C + F51V + D96E + K98I + D111A + G163K + H198S + Y220F + T231R + N233C + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + D27R + N33K + G38A + F51V + D96E + K98I + D111A + G163K + H198S + Y220F + T231R + N233C |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

Detergent composition E. In an embodiment the composition of the invention comprises a lipase variant of the invention and linear alkylbenzene sulfonate (LAS) and alcohol ethoxylate (AEO). In an embodiment the ratio between the surfactants may be 3:1, 2:1, 1:1, such as in the range from 10:1 to 1:10, such as 5:1 to 1:5, or 3:1 to 1:3. In a preferred embodiment the ratio is 2:1. In an embodiment the total surfactant concentration in the wash solution is from 0.005 to 0.75 mW such as 0.025-0.5 mM, in particular from 0.05-0.25 mM. In the wash solution linear alkylbenzene sulfonate (LAS) may be present in a concentration of 0.005-0.5 mM, such 0.05-0.25 mM, such as 0.01 mM. In an embodiment alcohol ethoxylate (AEO) may be present in the wash solution in a concentration of 0.0025-0.25 mW such 0.025-0.15 mW such as 0.05 mM. According to the invention the lipase activity in the wash solution is increased in comparison to the parent lipase, in particular SEQ ID NO: 1 (LIPOLASE™) (see Example 4). In a preferred embodiment the composition comprises one of the following set of substitutions using SEQ ID NO: 1 for numbering:

| |
|---|
| E1C + H198Y + N233C |
| E1C + L227F + N233C |
| E1C + E210T + N233C |
| E1C + E210N + N233C |
| E1C + V176M + N233C |
| E1C + K98T + N233C |
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |
| E1C + V2I + N233C |
| E1C + V2N + N233C |
| E1C + V2K + N233C |
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + T231R + N233C |
| E1C + D111A + N233C |
| E1C + G38A + N233C |
| E1C + N33Q + N233C |
| E1C + N33K + N233C |
| E1C + V176L + N233C |
| E1C + E56K + N233C |
| E1C + E210A + N233C |
| E1C + E210Q + N233C |
| E1C + E210R + N233C |
| E1C + K98R + N233C |
| E1C + K98V + N233C |
| E1C + F51L + N233C |
| E1C + F51I + N233C |
| E1C + E210K + N233C |
| E1C + K98Q + N233C |
| E1C + Y220F + N233C |
| E1C + H198L + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + K237C |
| E1C + K98I + N233C |
| E1C + D27R + F51I + E56R + K98E + T231R + N233C |
| E1C + D27R + F51I + E56R + K98E + T231R + N233C + D254S |

-continued

| |
|---|
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + F51L + D96E + K98I + D111A + G163S + H198S + Y220F + T231R + N233C + P256T |
| E1C + D27R + F51L + D96E + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + P256T |
| E1C + D27R + F51V + D96E + K98I + D111A + G163K + H198S + Y220F + T231R + N233C + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96E + K98I + D111A + G163S + H198S + Y220F + T231R + N233C + P256T |
| E1C + G38A + F51V + D96E + K98I + D111A + G163K + H198S + Y220F + T231R + N233C + P256T |
| E1C + F51V + D96E + K98I + D111A + G163K + H198S + Y220F + T231R + N233C + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + D27R + N33K + G38A + F51V + D96E + K98I + D111A + G163K + H198S + Y220F + T231R + N233C |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

Detergent composition F. In an embodiment the composition of the invention comprises a lipase variant of the invention and linear alkylbenzene sulfonate (LAS) and alcohol ethoxylate (AEO) and a chelating agent, such as EDTA. In an embodiment the ratio between the surfactants may be 3:1, 2:1, 1:1, such as in the range from 10:1 to 1:10, such as 5:1 to 1:5, or 3:1 to 1:3. In a preferred embodiment the ratio is 2:1. The chelating agent may be present in the wash solution in a concentration of 0.1-10 mW such as 1-5 mW such as around 2 mM. In an embodiment the total surfactant concentration in the wash solution is from 0.1 to 15 mW such as 0.5-10 mM, in particular from 1-5 mM, especially around 2 mM. In the wash solution linear alkylbenzene sulfonate (LAS) may be present in a concentration of 0.1-10 mW such 1-5 mW such as around 2 mM. In the wash solution alcohol ethoxylate (AEO) may be present in a concentration of 0.05-5 mM, such 0.5-3 mM, such as around 1 mM. According to the invention the lipase activity in the wash solution is increased in comparison to the parent lipase, in particular SEQ ID NO: 1 (LIPOLASE™) (see Example 4). In an embodiment, the wash solution may have a degree of hardness from about 0° dH to about 30° dH, such as between 0 and 15° dH, such as between 0 and 10° dH, such as between 3 and 20° dH, such as between 10 and 20° dH, or such as above 20° dH. In a preferred embodiment the composition comprises one of the following set of substitutions using SEQ ID NO: 1 for numbering:

| |
|---|
| E1C + E210T + N233C |
| E1C + E210N + N233C |
| E1C + E56R + N233C |
| E1C + D96L + N233C |
| E1C + N233C + D254S |
| E1C + E56K + N233C |
| E1C + E210A + N233C |
| E1C + E210Q + N233C |
| E1C + E210R + N233C |
| E1C + E210K + N233C |
| E1C + D27R + F51I + E56R + K98E + T231R + N233C |
| E1C + D27R + F51I + E56R + K98E + T231R + N233C + D254S |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

Detergent composition G. In an embodiment the composition of the invention comprises a lipase variant of the invention and linear alkylbenzene sulfonate (LAS) and alcohol ethoxylate (AEO). In an embodiment the ratio between the surfactants may be 3:1, 2:1, 1:1, such as in the range from 10:1 to 1:10, such as 5:1 to 1:5, or 3:1 to 1:3. In a preferred embodiment the ratio is 2:1. In the wash solution the total surfactant concentration may be from 0.1 to 15 mM, such as 0.5-10 mM, in particular from 1-5 mM, especially around 2 mM. In the wash solution linear alkylbenzene sulfonate (LAS) may be present in a concentration of 0.1-10 mM, such 1-5 mM, such as around 2 mM. In the wash solution alcohol ethoxylate (AEO) may be present in a concentration of 0.05-5 mM, such 0.5-3 mM, such as around 1 mM. According to the invention the lipase activity in the wash solution is increased in comparison to the parent lipase, in particular SEQ ID NO: 1 (LIPOLASE™) (see Example 4). In a preferred embodiment the composition comprises one of the following set of substitutions using SEQ ID NO: 1 for numbering:

| |
|---|
| E1C + H198Y + N233C |
| E1C + H198T + N233C |
| E1C + H198G + N233C |
| E1C + H198S + N233C |
| E1C + H198L + N233C |
| E1C + H198G + N233C |

Additional Enzymes

In one embodiment, the composition further comprises at least one additional enzyme, such as an amylase, protease, cellulase, another lipase, beta-glucanase, and/or mannanase.

The term "additional enzymes" as used herein, refers to a set of enzymes, that may be further included in the detergent composition of the present invention. Such enzymes may any enzyme that is believed to be useful in the detergent composition of the present invention.

In one embodiment, the at least one additional enzyme is an alpha-amylase variant comprising an modification in one or more positions corresponding to positions H1, N54, V56, K72, G109, F113, R116, T134, W140, W159, W167, Q169, Q172, L173, A174, R181, G182, D183, G184, W189, E194, N195, V206, G255, N260, F262, A265, W284, F289, G304, G305, W347, K391, Q395, W439, W469, R444, F473, G476, and G477 of SEQ ID NO: 1, wherein said alpha-amylase variant has a sequence identity of at least 75% but less than 100% to SEQ ID NO: 2 and wherein said alpha-amylase variant has alpha-amylase activity.

It may be advantageous to include additional enzymes to the composition according to the present invention. Such additional enzymes may be selected from enzyme variants selected based on their stability in a composition comprising a surfactant as such additional enzymes may be sensitive towards surfactants. In a particular embodiment, the at least one alpha-amylase variant comprises at two, three, four, five, six, seven, eight, nine, ten, eleven, twelfth, or thirteen of the following modifications H1*, H1A, N54S, V56T, K72R, G109A, F113Q, R116Q, R116H, T134E, W140Y, W140F, W140H, W159Y, W159F, W159H, W167Y, W167H, W167F, Q169E, Q172K, Q172G, Q172N, L173P, A174*, A174S, R181*, G182*, D183*, G184*, G184T, W189Y, W189F, W189H, W189E, W189D, W189Q, W189N, E194D, E194N, E194S, N195F, V206L, V206F, V206Y, G255A, N260G, N260P, N260A, N260G, N260P, N260A, A265G, W284G, W284H, F289H, G304K, G304R, G304Q, G304E, G305K, G305R, G305Q, G305E, W347Y, W347F, W347H, K391A, Q395P, W439N, W439Q, W439T, R444Q, W469T, W469N, F473R, G476R, G476Q, G476E, G476K G477K, G477R, G477Q, and G477E, wherein numbering of the positions is according to SEQ ID NO: 2, and wherein the alpha-amylase variant is an alpha-amylase variant of a parent alpha-amylase which has at least 70%, such as at least 71%, at least 72%, at least 73%, at least 74%, such as at least 75%, e.g., such as at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95%, at least 96%, at least 97%, at least 98%, at least 99% e. g. at least 99.1%, at least 99.2%, at least 99.3%, at least 99.4%, at least 99.5%, at least 99.6, or 100% sequence identity to SEQ ID NO: 2.

In a preferred embodiment, the at least one alpha-amylase variant comprises a deletion and/or a substitution at two or more positions corresponding to positions 181, 182, 183, and 184 of SEQ ID NO: 2, wherein the alpha-amylase variant has at least 75% sequence identity to SEQ ID NO: 1, such as at least 71%, at least 72%, at least 73%, at least 74%, at least 75%, at least 80%, at least 85%, at least 90%, at least 95%, at least 96%, at least 97%, at least 98%, or at least 99%, e. g. at least 99.1%, at least 99.2%, at least 99.3%, at least 99.4%, at least 99.5%, at least 99.6, but less than 100%.

Thus, in one embodiment, the at least one alpha-amylase variant comprises a deletion in the positions corresponding to R181+G182; R181+D183; R181+G184; G182+D183; G182+G184; or D183+G184 of SEQ ID NO: 2.

In a particular embodiment, the at least one alpha-amylase variant comprises a one or more of the following modifications: H1*, H1A, N54S, V56T, K72R, G109A, F113Q, R116Q, R116H, T134E, W140Y, W140F, W140H, W159Y, W159F, W159H, W167Y, W167H, W167F, Q169E, Q172K, Q172G, Q172N, L173P, A174*, A174S, R181*, G182*, D183*, G184*, G184T, W189Y, W189F, W189H, W189E, W189D, W189Q, W189N, E194D, E194N, E194S, N195F, V206L, V206F, V206Y, G255A, N260G, N260P, N260A, N260G, N260P, N260A, A265G, W284G, W284H, F289H, G304K, G304R, G304Q, G304E, G305K, G305R, G305Q, G305E, W347Y, W347F, W347H, K391A, Q395P, W439N, W439Q, W439T, R444Q, W469T, W469N, F473R, G476R, G476Q, G476E, G476K G477K, G477R, G477Q, and G477E and one of the pairwise deletions of R181+G182; R181+D183; R181+G184; G182+D183; G182+G184; or D183+G184; (numbering according to SEQ ID NO: 2), wherein the alpha-amylase variant is an alpha-amylase variant of a parent alpha-amylase which has at least 70%, such as at least 71%, at least 72%, at least 73%, at least 74%, such as at least 75%, e.g., such as at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95%, at least 96%, at least 97%, at least 98%, at least 99% e. g. at least 99.1%, at least 99.2%, at least 99.3%, at least 99.4%, at least 99.5%, at least 99.6, or 100% sequence identity to SEQ ID NO: 2.

Thus, in one embodiment, the alpha-amylase variant is selected from the group consisting of:

H1*+N54S+V56T+G109A+Q169E+Q172K+A174*+G182*+D183*+N195F+V206L+K391A+G476K;

H1*+N54S+V56T+G109A+R116H+A174S+G182*+D183*+N195F+V206L+K391A+G476K;

H1*+N54S+V56T+K72R+G109A+F113Q+R116Q+W167F+Q172G+A174S+G182*+D183*+G184T+N195F+V206L+K391A+P473R+G476K;

H1*+N54S+V56T+G109A+F113Q+R116Q+Q172N+A174S+G182*+D183*+N195F+V206L+A265G+K391A+P473R+G476K;

H1*+N54S+V56T+K72R+G109A+F113Q+W167F+Q172R+A174S+G182*+D183*+N195F+V206L+K391A+G476K;

H1*+N54S+V56T+K72R+G109A+R116H+T134E+W167F+Q172G+L173V+A174S+G182*+D183*+N195F+V206L+G255A+K391A+G476K;

H1*+N54S+V56T+K72R+G109A+R116H+T134E+W167F+Q172G+L173V+A174S+G182*+D183*+N195F+V206L+G255A+K391A+Q395P+T444Q+P473R+G476K;

H1*+N54S+V56T+G109A+T134E+A174S+G182*+D183*+N195F+V206L+K391A+G476K;

H1*+N54S+V56T+K72R+G109A+A174S+G182*+D183*+N195F+V206L+G255A+K391A+G476K; and

H1*+N54S+V56T+G109A+W167F+Q172E+L173P+A174K+G182*+D183*+N195F+V206L+K391A+G476K, wherein numbering is according to SEQ ID NO: 2, and wherein said alpha-amylase variant shares at least 80%, such as at least 85%, such as at least 90%, such as at least 93%, such as at least 94%, such as at least 95%, such as at least 96%, such as at least 97%, such as at least 98%, but less than 100% sequence identity with the polypeptide of SEQ ID NO: 2, and wherein said alpha-amylase variant has alpha-amylase activity.

In another or further embodiment, the additional enzyme is a protease. Accordingly, in one embodiment, the at least one additional enzyme is a protease having protease activity, wherein said protease is selected from the group of:

(a) a protease having a sequence identity of at least 70%, such as at least 75%, such as at least 80%, such as at least 85%, such as at least 90%, such as at least 95%, such as at least 98%, such as at least 99%, such as 100%, to the sequences of SEQ ID NOs: 4, 5, or 6;

(b) a protease variant comprising a substitution at one or more positions corresponding to positions 171, 173, 175, 179, or 180 of SEQ ID NO: 7, wherein said protease variant has a sequence identity of at least 75% but less than 100% to SEQ ID NO: 7; and (c) a protease variant comprising an modification in one or more positions corresponding to positions 32, 33, 48, 49, 50, 51, 52, 53, 54, 58, 59, 60, 61, 62, 94, 95, 96, 97, 98, 99, 100, 101, 102, 103, 104, 105, 106, 107, 116, 123, 124, 125, 126, 127, 128, 129, 130, 131, 132, 133, 150, 152, 153, 154, 155, 156, 158, 159, 160, 161, 164, 169, 175, 176, 177, 178, 179, 180, 181, 182, 183, 184, 185, 186, 197, 198, 203, 204, 205, 206, 207, 208, 209, 210, 211, 212, 213, 214, 215, and 216 as compared with the protease in SEQ ID NO:3, wherein said protease variant has at least 75% sequence identity to SEQ ID NO: 4.

In a particular embodiment, the protease is that of (a).

In another particular embodiment, the protease is that of (b). In one embodiment, the protease is the variant in (b) comprising a substitution in at least one position corresponding to positions 171, 173, 175, 179, or 180, and wherein the amino acid in the position corresponding to position 171 of SEQ ID NO: 7 is selected from the group consisting of W, K, E, D and N; and/or the amino acid in the position corresponding to position 173 of SEQ ID NO: 7 is P; and/or the amino acid in the position corresponding to position 175 of SEQ ID NO: 7 is selected from the group consisting of A, V, and P; and/or the amino acid in the position corresponding to position 179 of SEQ ID NO: 7 is selected from the group consisting of C, V, Q, S, T, E, H, K, M, N, Y, and A; and/or the amino acid in the position corresponding to position 180 of SEQ ID NO: 7 is Y.

In one embodiment, the composition comprises at least one protease variant which is a Savinase (SEQ ID NO: 4) variant. The Savinase variant is a variant of a parent protease having a sequence identity of at least 70%, such as at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94% at least 95% identity, at least 96%, at least 97%, at least 98%, or at least 99%, e. g. at least 99.1%, at least 99.2%, at least 99.3%, at least 99.4%, at least 99.5%, at least 99.6, but less than 100%, sequence identity to SEQ ID NO: 4.

Thus, in one embodiment, the protease is a protease variant comprising an modification in one or more positions corresponding to positions 32, 33, 48, 49, 50, 51, 52, 53, 54, 58, 59, 60, 61, 62, 94, 95, 96, 97, 98, 99, 100, 101, 102, 103, 104, 105, 106, 107, 116, 123, 124, 125, 126, 127, 128, 129, 130, 131, 132, 133, 150, 152, 153, 154, 155, 156, 158, 159, 160, 161, 164, 169, 175, 176, 177, 178, 179, 180, 181, 182, 183, 184, 185, 186, 197, 198, 203, 204, 205, 206, 207, 208, 209, 210, 211, 212, 213, 214, 215, and 216 as compared with the protease in SEQ ID NO:3, wherein said protease variant has at least 75% sequence identity to SEQ ID NO: 4.

In a particular embodiment, the modification in at least one position in said protease variant in (c) is selected from the group consisting of: 9, 15, 27, 42, 52, 55, 56, 59, 60, 66, 74, 85, 97, 99, 101, 102, 104, 116, 118, 154, 156, 157, 158, 161, 164, 176, 179, 182, 185, 188, 198, 199, 200, 203, 206, 210, 211, 212, 216, 230, 232, 239, 242, 250, 253, 255, 256, and 269, wherein numbering is according to SEQ ID NO: 4.

In a preferred embodiment, the protease variant comprises one or more of the following substitutions; S9E, S9R, A15T, K27R, N42R, G52S, S55P, T56P, G59D, G59E, N60D, N60E, V66A, N74D, S85N, S85R, S97A, S97E, S97D, S99E, S99D, S99G, S99N, S99H, S99M, S101A, V1021, V102N, S104A G116V, G116R, S154D, A156E, G157S, G157D, G157P, S158E, Y161A, R164S, Q176E, N179E, S182E, Q185N, A188P, N198D, V1991, Q200L, Y203W, S206G, S210V, L211D, L211Q, L211E, N212D, N212E, N212S, M216S, M216A, Q230H, Q239R, N242D, S250D, S253D, N255W, N255D, N255E, L256E, L256D, and R269H, wherein numbering is according to SEQ ID NO: 4.

In a further preferred embodiment, the protease variant has protease activity and comprises one or more of the following substitutions: S9R, A15T, V68A, N218D, or Q245R (numbering according to SEQ ID NO: 4), wherein the protease variant is a protease variant of a parent protease which has at least 70%, such as at least 71%, at least 72%, at least 73%, at least 74%, such as at least 75%, e.g., such as at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95%, at least 96%, at least 97%, at least 98%, at least 99% e.g. at least 99.1%, at least 99.2%, at least 99.3%, at least 99.4%, at least 99.5%, at least 99.6, or 100% sequence identity to SEQ ID NO: 4.

Thus, in another particular embodiment, the protease is that of (c). In one embodiment, the protease is the variant in (c) comprises one or more of the following substitutions; S9E, S9R, A15T, K27R, N42R, G52S, S55P, T56P, G59D, G59E, N60D, N60E, V66A, N74D, S85N, S85R, S97A, S97E, S97D, S99E, S99D, S99G, S99N, S99H, S99M, S101A, V1021, V102N, S104A G116V, G116R, S154D, A156E, G157S, G157D, G157P, S158E, Y161A, R164S, Q176E, N179E, S182E, Q185N, A188P, N198D, V1991, Q200L, Y203W, S206G, S210V, L211D, L211Q, L211E, N212D, N212E, N212S, M216S, M216A, Q230H, Q239R, N242D, S250D, S253D, N255W, N255D, N255E, L256E, L256D, and R269H, wherein numbering is according to SEQ ID NO: 4.

In a further or alternative embodiment, is the additional enzyme a lipase, such as a lipase variant. However, the set of enzymes (or termed "the additional enzymes") may be different variants of proteases, amylases or any other enzyme class.

In another embodiment, the detergent composition comprises more than one additional enzyme, such as two, three, four, five, six, seven, eight, nine, or ten additional enzymes.

In one embodiment, the composition according to the invention comprises two or more enzymes, such as at least three enzymes, more preferred at least four or five enzymes. Preferably, the enzymes have different substrate specificity, e.g., proteolytic activity, amylolytic activity, lipolytic activity, hemicellulytic activity or pectolytic activity.

The composition according to the invention may comprise one or more additional enzymes such as carbohydrate-active enzymes like carbohydrase, pectinase, mannanase, amylase, cellulase, arabinase, galactanase, xylanase, or protease, lipase, a, cutinase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Suitable additional proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellulomonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V41, S9R, A15T, K27R, *36D, V68A, N76D, N87S,R, *97E, A98S, S99G,D,A, S99AD, S101G,M,R S103A, V1041,Y,N, S106A, G118V,R, H120D,N, N123S, S128L, P129Q, S130A, G160D, Y167A, R170S, A194P, G195E, V199M, V2051, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Eraser®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces lipases* (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO 11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Suitable additional amylases which can be used together with the variants of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+1201F+A209V+Q264S.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, 1203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K

E187P+I203Y+R458N+T459S+D460T+G476K wherein the variants optionally further comprises a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions: N21D+D97N+V128I, wherein the variants optionally further comprises a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Plus™, Natalase™, Liquozyme X and BAN™ (from Novozymes A/S), and Rapidase™ Purastar™/Effectenz™, Powerase, Preferenz S1000, Preferenz S2000, Preferenz S100 and Preferenz S110 (from Genencor International Inc./DuPont).

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

A detergent composition according to the invention may also comprise additional enzymes such as pectate lyases e.g. Pectawash™, chlorophyllases etc.

The detergent enzyme(s) may be included in the detergent composition according to the invention by adding separate additives containing one or more enzymes, or by adding a combined additive comprising all of these enzymes. A detergent additive, i.e., a separate additive or a combined additive, may be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

In one embodiment, the number of modifications in the lipase variant is 1 to 30, e.g. 1 to 20, 1 to 10 and 1 to 5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 modifications.

In one embodiment, the number of modifications in the lipase variant is 1 to 20, e.g. 1 to 10 and 1 to 5, such as 1, 2, 3, 4, 5, 6, 7, 8, 9, or 10 modifications.

Essential amino acids in a polypeptide may be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In the context of the present invention, any variant, i.e. a lipase, an alpha-amylase, or a protease variant, have been prepared from a parent enzyme. Such a parent enzyme is defined as a polypeptide comprising or consisting of the amino acid sequences listed as SEQ ID NO: 1, 2, 3, 4, 5, 6. Thus, the variants have been prepared from a parent enzyme. A parent enzyme may be identified by sequence homology. The homology between two amino acid sequences is in this context described by the parameter "identity" for purposes of the present invention, the degree of identity between two amino acid sequences is determined using the Needleman-Wunsch algorithm as described above. The output from the routine is besides the amino acid alignment the calculation of the "Percent Identity" between the two sequences.

Based on this description it is routine for a person skilled in the art to identify suitable homologous alpha-amylases, proteases, and lipases, which may be modified as described herein.

Substantially homologous parent variants may have one or more (several) amino acid substitutions, deletions and/or insertions, in the present context the term "one or more" is used interchangeably with the term "several". These changes are preferably of a minor nature, that is conservative amino acid substitutions as described above and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, *EMBO J.* 4: 1075; Nilsson et al., 1991, *Methods Enzymol.* 198: 3. See, also, in general, Ford et al., 1991, *Protein Expression and Purification* 2: 95-107.

Although the changes described above preferably are of a minor nature, such changes may also be of a substantive nature such as fusion of larger polypeptides of up to 300 amino acids or more both as amino- or carboxyl-terminal extensions.

The parent enzyme may be (a) a polypeptide having at least 70% sequence identity to the mature polypeptide of SEQ ID NO: 1, 2, 3, 4, 5, or 6.

Accordingly, the parent lipase has a sequence identity to the polypeptide with SEQ ID NO: 1 of at least 70%, such as at least 71%, at least 72%, at least 73%, at least 74%, at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, e.g. at least 99.1%, at least 99.2%, at least 99.3%, at least 99.4%, at least 99.5%, at least 99.6, or 100%, which have lipase activity.

Accordingly, the parent alpha-amylase has a sequence identity to the polypeptide with SEQ ID NO: 2 of at least 70%, such as at least 71%, at least 72%, at least 73%, at least 74%, at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, e.g. at least 99.1%, at least 99.2%, at least 99.3%, at least 99.4%, at least 99.5%, at least 99.6, or 100%, which have alpha-amylase activity.

Accordingly, the parent protease has a sequence identity to the polypeptide with SEQ ID NO: 2, 3, 4, 5, or 6 of at least 70%, such as at least 71%, at least 72%, at least 73%, at least 74%, at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, e.g. at least 99.1%, at least 99.2%, at least 99.3%, at least 99.4%, at least 99.5%, at least 99.6, or 100%, which have protease activity.

The parent enzymes may be a hybrid polypeptide in which a region of one polypeptide is fused at the N-terminus or the C-terminus of a region of another polypeptide and thereby providing the fusion parent enzyme. The terms "fusion" and "hybrid" may be used interchangeably herein but constitute the same meaning and purpose, and should not be understood in any limiting manner.

A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide may further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent enzyme may be obtained from organisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

Variants present in the composition according to the invention may be prepared by a method for obtaining a variant having the specific enzymatic activity, wherein the method comprises the steps of: (a) introducing into a parent enzyme a modification at one or more (e.g., several) positions as specified herein; and (b) recovering the variant.

The skilled person would know how to prepare a variant. However, variants may be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure may be used in the present invention. There are many commercial kits available that may be used to prepare variants.

Synthetic gene construction entails in vitro synthesis of a designed polynucleotide molecule to encode a polypeptide of interest. Gene synthesis may be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions may be made and tested using known methods of mutagenesis, recombination, and/or shuffling, followed by a relevant screening procedure, such as those disclosed by Reidhaar-Olson and Sauer, 1988, *Science* 241:

53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, DNA 7: 127).

Mutagenesis/shuffling methods may be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Besides enzymes the compositions according to the invention may comprise additional components. Accordingly, in one embodiment, the composition further comprises at least one chelating agent; and/or at least one surfactant; and/or at least one polymer; and/or at least one hydrotrope; and/or at least one builder and/or co-builder; and/or at least one perfume; and/or at least one kind of bleaching system.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

The lipase variant, or any other enzyme variant, may be added to a composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquid.

The lipase variant may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per gram detergent composition.

The lipase variant may be stabilized using stabilizing agents, which may be selected from the group containing propylene glycol, glycerol, a sugar, a sugar alcohol, lactic acid, boric acid, borate and phenyl boronic acid derivates, such as those where the residue R in the phenyl boronic acid derivative is a C1-C6 alkyl group and among these, more preferably, $CH_3$, $CH_3CH_2$ or $CH_3CH_2CH_2$. The residue R in the phenyl boronic acid derivative may also be hydrogen. One example of a phenyl boronic acid derivative is 4-formylphenylboronic acid (4-FPBA) with the following formula:

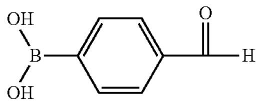 [SMILES: O=Cc1ccc(B(O)O)cc1]

Phenyl boronic acid derivatives may furthermore have other chemical modifications on the phenyl ring, and in particular they can contain one or more methyl, amino, nitro, chloro, fluoro, bromo, hydroxyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, 2,2,5,7,8-pentamethylchroman-6-sulfonyl residues or groups or combinations thereof. All stabilizing agents may be present in the detergent composition of the present invention in all protonated or deprotonated forms. Furthermore, all such compounds, in particular their deprotonated forms, can be associated with cations. Preferred cations in this respect are monovalent or polyvalent, in particular divalent, cations, in particular Na ions ($Na^+$), K ions ($K^+$), Li ions ($Li^+$), Ca ions ($Ca^{2+}$), Mg ions ($Mg^{2+}$), Mn ions ($Mn^{2+}$) and Zn ions ($Zn^{2+}$). The compositions of the present invention may comprise two or more stabilizing agents e.g. such as those selected from the group consisting of propylene glycol, glycerol, 4-formylphenyl boronic acid and borate. One example is a composition of the present invention comprising 4-formylphenyl boronic acid and/or borate. The phenyl boronic acid derivative may be contained in the detergent composition in a quantity of from 0.00001 to 5.0 wt %, preferably from 0.0001 to 3.0 wt %, from 0.001 to 2.0 wt %, from 0.005 to 1.0 wt %, from 0.01 to 0.5 wt %, from 0.02 to 0.3 wt %. Preferably, the boric acid/borate is contained in a quantity of from 0.001 to 5.5 wt. % and increasingly preferably of from 0.01 to 4.5 wt. %, from 0.05 to 3.5 and from 0.1 to 3, 0.4 bis 2.49, 0.5 bis 1.5 wt. % in the composition. Addition of a combination of borate and 4-formylphenyl boronic acid has been found to be particularly effective, leading to a high increase in enzyme stability in compositions. Preferably, the boric acid/borate is contained in a quantity of from 0.001 to 5.5 wt. % and increasingly preferably from 0.075 to 4.5 wt. %, from 0.09 to 3.5 and from 0.1 to 2.49 wt. %, and the phenyl boronic acid derivative is contained in a quantity of from 0.001 to 0.08 wt. % and increasingly preferably from 0.003 to 0.06 wt. %, from 0.005 to 0.05 wt. %, from 0.007 to 0.03 wt. % and from 0.009 to 0.01 wt. % in a detergent composition. Particularly preferred is the addition of 4-formylphenyl boronic acid in an amount of 1.0 to 2.0 wt % in combination with 1.0 wt % borate.

The composition according to the invention may comprise lipase variants which may also be stabilized using peptide aldehydes or ketones such as described in WO 2005/105826 and WO 2009/118375. Another example of compositions according to the invention relates to a detergent composition comprising lipase variant as described herein, wherein the detergent formulation is as disclosed in WO 97/07202, which is hereby incorporated by reference.

The composition according to the invention may also comprise further surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the composition will usually comprise from about 1% to about 40% by weight of a cationic surfactant. Non-limiting examples of cationic surfactants include alklydimethylehanolamine quat (ADMEAQ), cetyltrimethylammonium bromide (CTAB), dimethyldistearylammonium chloride (DSDMAC), and alkylbenzyldimethylammonium, and combinations thereof, Alkyl quaternary ammonium compounds, Alkoxylated quaternary ammonium (AQA), When included therein the composition will usually comprise from about 1% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the composition will usually comprise from about 1% to about 40% by weight of a zwitterionic surfactant. Non-limiting examples of zwitterionic surfactants include betaine, alkyldimethylbetaine, and sulfobetaine, and combinations thereof.

Yet another component of the composition according to the present invention is hydrotropes.

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

Thus, the composition according to the present invention may comprise 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Another component of a composition may be builders and/or co-builders. The term "builder" may be classified by the test described by M. K. Nagaraja et al., JAOCS, Vol. 61, no. 9 (September 1984), pp. 1475-1478 to determine the minimum builder level required to lower the water hardness at pH 8 from 2.0 mM (as $CaCO_3$) to 0.10 mM in a solution. The builder may particularly be a chelating agent that forms water-soluble complexes with e.g. calcium and magnesium ions. The term "chelating agents" or "chelators" as used herein, refers to chemicals that form molecules with certain metal ions, inactivating the ions so that they cannot react with other elements thus a binding agent that suppresses chemical activity by forming chelates. Chelation is the formation or presence of two or more separate bindings between a ligand and a single central atom. The ligand may be any organic compound, a silicate or a phosphate. Thus, in one embodiment, the composition according to the present invention may comprise about 0-65% by weight, such as about 5% to about 50% of a detergent builder or co-builder, or a mixture thereof. The builder and/or co-builder may particularly be a chelating agent that forms water-soluble complexes with Ca and Mg. Any builder and/or co-builder known in the art for use in laundry, ADW and hard surfaces cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The composition according to the present invention may also comprise 0-65% by weight, such as about 5% to about 40%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly (acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediaminetetrakis(methylene)tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), $\alpha$-alanine-N,N-diacetic acid ($\alpha$-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Yet another component of the composition may be bleaching systems. Thus, in one embodiment, the detergent composition according to the present invention may comprise 0-10% by weight, such as about 1% to about 5%, of a bleaching system. Any bleaching system known in the art for use in laundry, ADW and hard surfaces cleaning detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. By bleach activator is meant herein a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetyl athylene diamine (TAED), sodium 3,5,5 trimethyl hexanoyloxybenzene sulphonat, diperoxy dodecanoic acid, 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxy)benzenesulfonate (ISONOBS), tetraacetylethylenediamine (TAED) and 4-(nonanoyloxy) benzenesulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like Triacin has the advantage that it is environmental friendly as it eventually degrades into citric acid and alcohol. Furthermore acethyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthaloylamino)percapronic acid (PAP). The bleaching system may also include a bleach catalyst. In some embodiments the bleach component may be an organic catalyst selected from the group consisting of organic catalysts having the following formulae:

(i)

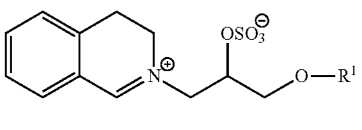

-continued (ii)

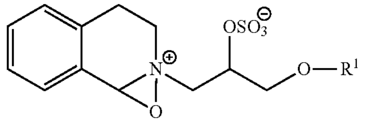

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO2007/087258, WO2007/087244, WO2007/087259, WO2007/087242.

Suitable photobleaches may for example be sulfonated zinc phthalocyanine Another component of a composition is polymers. Thus, in one embodiment, the composition according to the invention comprise a polymer.

Accordingly, the composition according to the present invention may comprise 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly (ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of polyethylene terephthalate and polyoxyethene terephthalate (PET-POET), PVP, poly(vinylimidazole) (PVI), poly(vinylpyridin-N-oxide) (PVPO or PVPNO) and polyvinylpyrrolidone-vinylimidazole (PVPVI). Further exemplary polymers include polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Yet another component of compositions may be fabric hueing agents. Thus, in one embodiment, the detergent composition according to the invention comprises a fabric hueing agent.

The detergent composition according to the present invention may also comprise fabric hueing agents such as dyes or pigments which when formulated in detergent compositions can deposit onto a fabric when said fabric is contacted with a wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). A detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized.

The choice of such ingredients is well within the skill of the artisan. The composition according to the invention may also comprise dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc. The detergent composition according to the invention may also comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition. A detergent composition according to the invention may preferably also comprise additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2,2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

The composition according to the invention may also comprise one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof. The detergent composition according to the invention may also comprise one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

Thus, in one particular embodiment, the composition further comprises at least one chelating agent; and/or at least one surfactant; and/or at least one polymer; and/or at least one hydrotrope; and/or at least one builder and/or co-builder; and/or at least one perfume; and/or at least one kind of bleaching system.

Formulation of the Composition

The composition according to the invention may be in any convenient form, e.g., a bar, a homogenous tablet, a tablet having two or more layers, a regular or compact powder, a granule, a paste, a gel, or a regular, compact or concentrated liquid. Accordingly, in one embodiment, the composition is a detergent composition or an adjunct composition. In one embodiment, the ancillary composition is a pre-treatment composition. In another embodiment, the composition is a soaking composition. In yet another embodiment, the composition is a boosting composition. In any of the adjunct compositions the composition may be formulated in any form, such as a liquid, a gel, a powder or granulate.

In one embodiment, the detergent composition according to the present invention, is a liquid laundry detergent composition or a powder laundry detergent composition.

The term "liquid laundry detergent composition" as used herein refers to a detergent composition which is in a stabilized liquid form and used in a method for laundering a fabric. Thus, the detergent composition has been formulated to be in fluid form.

The term "powder laundry detergent composition" as used herein refers to a detergent composition which is in a solid form, such as a granulate, non-dusting granulate or powder, which is used in a method for laundering a fabric.

Detergent formulation forms: Layers (same or different phases), Pouches, versus forms for Machine dosing unit.

Pouches may be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients may be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Methods and Uses

In one aspect the invention relates to use of the composition as described herein in laundry. Accordingly, the present invention relates to use of a composition comprising (i) at least one surfactant and (ii) a lipase variant of a parent lipase, wherein said variant (a) comprises a modification in at least one position corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1;

(b) has a sequence identity of at least 75% but less than 100% to SEQ ID NO: 1;

(c) has lipase activity; and has an improved activity as compared to the parent lipase in laundry.

In one embodiment, the use of the composition as described herein, is in laundry.

A composition according to the invention may be formulated, e.g., as a hand or machine laundry detergent composition including a laundry additive composition suitable for pre-treatment of stained fabrics and a rinse added fabric softener composition, or be formulated as a detergent composition for use in general household hard surface cleaning operations. Thus, in one embodiment, the composition is a liquid laundry detergent composition or a powder laundry detergent composition.

A cleaning process or the textile care process may for example be a laundry process, a household hard surface cleaning operation is considered to encompass cleaning of hard surfaces, such as bathroom tiles, floors, table tops, drains, sinks and washbasins. Laundry processes can for example be household laundering, but it may also be industrial laundering. A process for laundering of fabrics and/or garments may be a process comprises treating fabrics with a washing solution containing a detergent composition, and at least one protease variant. A cleaning process or a textile care process can for example be carried out in a machine washing process or in a manual washing process. The washing solution can for example be an aqueous washing solution containing a detergent composition.

The fabrics and/or garments subjected to a washing, cleaning or textile care process may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabbit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

Typical detergent compositions include various components in addition to the enzymes, these components have different effects, some components like the surfactants lower the surface tension in the detergent, which allows the stain being cleaned to be lifted and dispersed and then washed away, other components like bleach systems remove discolor often by oxidation and many bleaches also have strong bactericidal properties, and are used for disinfecting and sterilizing. Yet other components like builder and chelator softens, e.g., the wash water by removing the metal ions form the liquid.

The enzyme compositions may further comprise at least one or more of the following: a surfactant, a builder, a chelator or chelating agent, bleach system or bleach component in laundry.

The amount of a surfactant, a builder, a chelator or chelating agent, bleach system and/or bleach component may be reduced compared to amount of surfactant, builder, chelator or chelating agent, bleach system and/or bleach component used without the added lipase variant of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of lipase variants of the invention, such as a conventional amount of such component. Detergent compositions may also be composition which is free of at least one component which is a builder, a chelator or chelating agent, bleach system or bleach component and/or polymer.

In one embodiment, the use is in laundry at low temperature, such as less than 50°, such as less than 45° C., such as less than 40° C., such as less than 35° C., such as less than 30° C., such as less than 25° C., such as less than 20° C., such as less than 15° C.

The term "low temperature" as used herein, refers to is a temperature of 5-50° C., such as 5-45° C., preferably 5-40° C., more preferably 5-30° C., more preferably 5-20° C., most preferably 5-15° C., and in particular 5-10° C.

In one embodiment, the use of the composition is in laundry at low temperature, such as less than 50°, such as less than 45° C., such as less than 40° C., such as less than 35° C., such as less than 30° C., such as less than 25° C., such as less than 20° C., such as less than 15° C.

Washing Method

The composition according to the invention is ideally suited for use in laundry applications. Thus, in one aspect, the present invention relates to a method of laundering, comprising laundering a garment with a composition as described herein, preferably at a temperature of 50° C. or less, such as 40° C. or less, or more preferably at a temperature of 30° C. or less, or even more preferably at a temperature of 20° C. or less. Accordingly, the method of laundering comprises laundering a fabric with a composition comprising (i) at least one surfactant and (ii) a lipase variant of a parent lipase, wherein said variant a) comprises a modification in at least one position corresponding to positions E1, V2, N33, F51, E56, L69, K98, V176, H198, E210, Y220, and L227 of SEQ ID NO: 1; and optionally further comprises a modification in at least one position corresponding to positions D27, G38, D96, D111, G163, T231, N233, D254, and P256 of SEQ ID NO: 1;

b) has a sequence identity of at least 75% but less than 100% to SEQ ID NO: 1;

c) has lipase activity; and has an improved activity as compared to the parent lipase preferably at a temperature of 50° C. or less, preferably at a temperature of 40° C. or less, or more preferably at a temperature of 30° C. or less, or even more preferably at a temperature of 20° C. or less.

In one embodiment, the concentration of said surfactant during said laundry process is at least 0.005 g/L wash water, such as at least 0.007 g/L, such as at least 0.01 g/L, or such as at least 0.1 g/L.

In one embodiment, the concentration of said surfactant during said laundry process is at least 1 g/L wash water, such as at least 2 g/L, such as at least 3 g/L, or such as 4.

In one embodiment, the concentration of said surfactant during said laundry process is in the range from between 0.05-10 g/L wash water, such as between 0.1-8 g/L, such as between 0.1-6 g/L, or such as between 0.2-6 g/L wash water.

These methods include a method for laundering a fabric. The method comprises the steps of contacting a fabric to be laundered with a cleaning laundry solution comprising a detergent composition. The fabric may comprise any fabric capable of being laundered in normal consumer use conditions. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH from about 5.0 to about 11.5, or from about 6 to about 10.5, about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5 to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, about 8 to about 11, about 8 to about 10, about 8 to about 9, about 9 to about 11, about 9 to about 10, about 10 to about 11, preferably about 5.5 to about 11.5.

Water hardness in a cleaning process is determined by the water hardness in the water and/or by the presence of chelating agents in the detergent composition.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 16° dH, under typical US wash conditions about 6° dH, and under typical Asian wash conditions, about 3° dH, however, the wash conditions may vary locally depending on the source of water.

In one embodiment, the composition according to the invention is for use is in a laundry process where the resulting water hardness is between 0 and 30° dH, such as between 0 and 15° dH, such as between 0 and 10° dH, such as between 3 and 20° dH, such as between 10 and 20° dH, or such as above 20° dH.

In particular embodiments, the washing process is conducted over a certain period of time, from 10 minutes to more than 400 minutes. Thus, in one embodiment, the use is in a laundry process where the wash cycle is less than 360 minutes, such as less than 280 minutes, such as less than 150 minutes, such as less than 100 minutes, such as less than 50 minutes, such as less than 30 minutes, such as less than 15 minutes, or such as less than 10 minutes.

In one embodiment, the method is a method of pre-treating a fabric with a composition according to the invention, comprising the steps of adding said composition to said fabric, and leaving the composition on the fabric for a period of time, and rinsing off said composition from said fabric.

The compositions for use in the methods described above may further comprises at least one additional enzyme as set forth in the section above, such as an enzyme selected from the group of hydrolases such as proteases, lipases and cutinases, carbohydrases such as amylases, cellulases, hemicellulases, xylanases, and pectinase or a combination hereof.

The Invention is Described in the Following Numbered Paragraphs:

1. A lipase variant of a parent lipase, wherein said variant
   (a) comprises a modification in at least one position corresponding to positions E1, V2, N33, F51, E56, L69, K98, V176, H198, E210, Y220, L227, and K237 of SEQ ID NO: 1; and optionally further comprises a modification in at least one position corresponding to positions D27, G38, D96, D111, G163, T231, N233, D254, and P256 of SEQ ID NO: 1;
   (b) has a sequence identity of at least 75% but less than 100% to SEQ ID NO: 1;
   (c) has lipase activity.
2. The variant according to paragraph 1, wherein said lipase variant comprises a modification in at least one of the following positions: E1, V2, D27, N33, G38, F51, E56, L69, D96, K98, D111, G163, V176, H198, E210, Y220, L227, T231, N233, K237, D254, and P256, wherein numbering is according to SEQ ID NO: 1.
3. The variant according to paragraph 1 or 2, wherein said lipase variant comprises at least one of the following modifications; E1C, V2Y, D27R, N33K, N33Q, G38A, F51V, E56K, L69R, D96E, D96L, K98I, K98Q, D123A, G163K, V176L, H198S, E21K, Y220F, L227G, T231R, N233R, N233C, K237C, D254S, and P256T, wherein numbering is according to SEQ ID NO: 1.
4. The variant according to any one of paragraphs 1-3, wherein said lipase variant further comprises one of the substitutions selected from the group of: S54T, S83T, G91A, A150G, I255A, and E239C.
5. The variant according to any one of paragraphs 1-4, wherein said lipase variant has at least 75%, such as at least 75%, such as at least 80%, such as at least 85%, such as at least 90%, such as at least 95%, such as at least 96%, such as at least 97%, such as at least 98%, such as at least 99%, but less than 100% sequence identity to the amino acid sequence of SEQ ID NO: 1.
6. The variant according to any one of paragraphs 1-5, wherein said parent lipase is a lipase having at least 70%, such as at least 75%, such as at least 80%, such as at least 85%, such as at least 90%, such as at least 95%, such as at least 96%, such as at least 97%, such as at least 98%, such as at least 99%, such as at least 100% sequence identity to the amino acid sequence of SEQ ID NO: 1.
7. The variant according to any of paragraphs 1-6, wherein the lipase variant comprises substitutions E1C+N233C and one or more additional substitutions.
8. The variant according to any of paragraphs 1-7, wherein the variant comprises or consists of one of the following set of substitutions using SEQ ID NO: 1 for numbering:

| |
|---|
| E1C + H198L + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + H198Y + N233C |
| E1C + H198T + N233C |
| E1C + H198G + N233C |
| E1C + L227F + N233C |
| E1C + L227R + N233C |
| E1C + E210T + N233C |
| E1C + E210N + N233C |
| E1C + V176M + N233C |

-continued

| |
|---|
| E1C + K98T + N233C |
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |
| E1C + V2I + N233C |
| E1C + V2N + N233C |
| E1C + V2K + N233C |
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + T231R + N233C |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + E210A + N233C |
| E1C + E210Q + N233C |
| E1C + E210R + N233C |
| E1C + H198D + N233C |
| E1C + K98R + N233C |
| E1C + K98V + N233C |
| E1C + F51L + N233C |
| E1C + F51I + N233C |
| E1C + K237C |
| E1C + L227G + N233C |
| E1C + E210K + N233C |
| E1C + V176L + N233C |
| E1C + K98Q + N233C |
| E1C + E56K + N233C |
| E1C + L147S + N233C + D254S |
| E1C + Y220F + N233C |
| E1C + K98I + N233C |
| E1C + N233C |
| E1C + D27R + F51I + E56R + K98E + T231R + N233C |
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + F51L + D96E + K98I + D111A + G163S + H198S + Y220F + T231R + N233C + P256T |
| E1C + D27R + F51L + D96E + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + P256T |
| E1C + D27R + F51V + D96E + K98I + D111A + G163K + H198S + Y220F + T231R + N233C + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96E + K98I + D111A + G163S + H198S + Y220F + T231R + N233C + P256T |
| E1C + F51L + D96E + K98I + D111A + G163K + H198S + Y220F + T231R + N233C + D254S + P256T |
| E1C + G38A + F51V + D96E + K98I + D111A + G163K + H198S + Y220F + T231R + N233C + P256T |
| E1C + F51V + D96E + K98I + D111A + G163K + H198S + Y220F + T231R + N233C + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + D27R + N33K + G38A + F51V + D96E + K98I + D111A + G163K + H198S + Y220F + T231R + N233C |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

9. The variant of any one of paragraphs 1-8, wherein the variant has lipase activity, such as increased relative activity, compare to the parent lipase, in particular the lipase shown as SEQ ID NO: 1.
10. A composition comprising (i) at least one surfactant and (ii) a lipase variant of a parent lipase, wherein said variant
(a) comprises a modification in at least one position corresponding to positions E1, V2, N33, F51, E56, L69, K98, V176, H198, E210, Y220, L227, and K237 of SEQ ID NO: 1; and optionally further comprises a modification in at least one position corresponding to positions D27, G38, D96, D111, G163, T231, N233, D254, and P256 of SEQ ID NO: 1;
(b) has a sequence identity of at least 75% but less than 100% to SEQ ID NO: 1;
(c) has lipase activity; and
(d) has an improved activity as compared to the parent lipase.
11. The composition of paragraph 10, comprising a lipase variant of any one of paragraphs 1-9.
12. The composition according to paragraph 10 or 11, wherein the concentration of said surfactant is at least 3 wt %, such as at least 4 wt %, such as at least 5 wt %, such as at least 6 wt %, such as at least 7 wt %, such as at least 8 wt %, of said composition.
13. The composition according to any one of paragraphs 10-12, wherein said at least one surfactant comprises an anionic surfactant, such as linear alkylbenzene sulfonate (LAS) or alcohol ether sulfate (AEOS).
14. The composition according to any one of paragraphs 10-13, wherein said at least one surfactant is a mix of two or more surfactants.
15. The composition according to any one of paragraphs 10-14, wherein said at least one surfactant is a mix of a first surfactant and a second surfactant.
16. The composition according to any one of paragraphs 10-15, wherein said first surfactant is a first anionic surfactant and said second surfactant is a second anionic surfactant.
17. The composition according to any one of paragraphs 10-16, wherein said first anionic surfactant is linear alkylbenzene sulfonate (LAS) and said second anionic surfactant is alcohol ethersulfate (AEOS).
18. The composition according to any one of paragraphs 10-17, wherein said first surfactant is an anionic surfactant and said second surfactant is a non-ionic surfactant.
19. The composition according to paragraph 18, wherein said anionic surfactant is linear alkylbenzene sulfonate (LAS) or alcohol ether sulfate (AEOS) and said non-ionic surfactant is alcohol ethoxylate (AEO).
20. The composition according to any one of paragraphs 10-19, wherein the total surfactant concentration during cleaning is between from 0.1 to 15 mM, such as 0.5-10 mM, in particular from 1-5 mM. concentration is between 0.01 and 10 mM.
21. The composition according to any one of paragraphs 10-20, wherein said first surfactant and said second surfactant is present in said composition in a ratio of 3:1, 2:1, 1:1, such as in the range from 10:1 to 1:10, such as 5:1 to 1:5, or 3:1 to 1:3.
22. The composition according to any one of paragraphs 10-21, wherein said lipase variant comprises a modification in at least one of the following positions: E1, V2, D27, N33, G38, F51, E56, L69, D96, K98, D111, G163, V176, H198, E210, Y220, L227, T231, N233, K237, D254, and P256, wherein numbering is according to SEQ ID NO: 1.
23. The composition according to any one of paragraphs 10-22, wherein said lipase variant comprises at least one of the following modifications; E1C, V2Y, D27R, N33K, N33Q, G38A, F51V, E56K, L69R, D96E, D96L, K98I, K98Q, D111A, G163K, V176L, H198S, E210K, Y220F, L227G, T231R, N233R, N233C, K237C, D254S, and P256T, wherein numbering is according to SEQ ID NO: 1.
24. The composition according to any one of paragraphs 10-23, wherein the lipase variant comprises substitutions E1C+N233C and one or more additional substitutions.
25. The composition according to any one of paragraphs 10-24, wherein said lipase variant further comprises one of the substitutions selected from the group of: S54T, S83T, G91A, A150G, I255A, and E239C.
26. The composition according to any one of paragraphs 10-25, wherein said lipase variant has at least 75%, such as at least 75%, such as at least 80%, such as at least 85%, such as at least 90%, such as at least 95%, such as at least 96%, such as at least 97%, such as at least 98%, such as at least 99%, but less than 100% sequence identity to the amino acid sequence of SEQ ID NO: 1.
27. The composition according to any one of paragraphs 10-26, wherein said parent lipase is a lipase having at least 70%, such as at least 75%, such as at least 80%, such as at least 85%, such as at least 90%, such as at least 95%, such as at least 96%, such as at least 97%, such as at least 98%, such as at least 99%, such as 100% sequence identity to the amino acid sequence of SEQ ID NO: 1.
28. The composition according to any one of paragraphs 10-27, comprising linear alkylbenzene sulfonate (LAS) and a lipase variant of any one of paragraphs 1-9, in particular a lipase variant comprising one of the following set of substitutions using SEQ ID NO: 1 for numbering:

| |
|---|
| E1C + H198T + N233C |
| E1C + H198G + N233C |
| E1C + L227F + N233C |
| E1C + E210T + N233C |
| E1C + E210N + N233C |
| E1C + V176M + N233C |
| E1C + K98T + N233C |
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |

-continued

| |
|---|
| E1C + V2I + N233C |
| E1C + V2N + N233C |
| E1C + V2K + N233C |
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + V176L + N233C |
| E1C + E56K + N233C |
| E1C + E210A + N233C |
| E1C + E210Q + N233C |
| E1C + E210R + N233C |
| E1C + K98R + N233C |
| E1C + K98V + N233C |
| E1C + F51L + N233C |
| E1C + F51I + N233C |
| E1C + L227G + N233C |
| E1C + E210K + N233C |
| E1C + K98Q + N233C |
| E1C + Y220F + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + K237C |
| E1C + K98I + N233C |
| E1C + D27R + F51I + E56R + K98E + T231R + N233C |
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |

29. The composition according to any one of paragraphs 10-27, comprising alcohol ether sulfate (AEOS) and a lipase variant of any one of paragraphs 1-9, in particular a lipase variant comprising one of the following set of substitutions using SEQ ID NO: 1 for numbering:

| |
|---|
| E1C + H198Y + N233C |
| E1C + H198T + N233C |
| E1C + H198G + N233C |
| E1C + H198S + N233C |

-continued

| |
|---|
| E1C + H198L + N233C |
| E1C + H198G + N233C |

30. The composition according to any one of paragraphs 10-27, comprising linear alkylbenzene sulfonate (LAS) and alcohol ethoxylate (AEO) and a lipase variant of any one of paragraphs 1-9, in particular a lipase variant comprising one of the following set of substitutions using SEQ ID NO: 1 for numbering:

| |
|---|
| E1C + H198Y + N233C |
| E1C + H198T + N233C |
| E1C + H198G + N233C |
| E1C + L227F + N233C |
| E1C + L227R + N233C |
| E1C + E210T + N233C |
| E1C + E210N + N233C |
| E1C + V176M + N233C |
| E1C + K98T + N233C |
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |
| E1C + V2I + N233C |
| E1C + V2N + N233C |
| E1C + V2K + N233C |
| E1C + V2A + N233C |
| E1C + D96L + N233C |

-continued

| |
|---|
| E1C + L69R + N233C |
| E1C + V2Y + N233C |
| E1C + N233C + P256T |
| E1C + N233C + D254S |
| E1C + T231R + N233C |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + V176L + N233C |
| E1C + E56K + N233C |
| E1C + E210A + N233C |
| E1C + E210Q + N233C |
| E1C + E210R + N233C |
| E1C + H198D + N233C |
| E1C + K98R + N233C |
| E1C + K98V + N233C |
| E1C + F51L + N233C |
| E1C + F51I + N233C |
| E1C + L227G + N233C |
| E1C + E210K + N233C |
| E1C + K98Q + N233C |
| E1C + Y220F + N233C |
| E1C + H198L + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + K237C |
| E1C + K98I + N233C |
| E1C + D27R + F51I + E56R + K98E + T231R + N233C |
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + F51L + D96E + K98I + D111A + G163S + H198S + Y220F + T231R + N233C + P256T |
| E1C + D27R + F51L + D96E + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + P256T |
| E1C + D27R + F51V + D96E + K98I + D111A + G163K + H198S + Y220F + T231R + N233C + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96E + K98I + D111A + G163S + H198S + Y220F + T231R + N233C + P256T |
| E1C + G38A + F51V + D96E + K98I + D111A + G163K + H198S + Y220F + T231R + N233C + P256T |
| E1C + F51V + D96E + K98I + D111A + G163K + H198S + Y220F + T231R + N233C + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + D27R + N33K + G38A + F51V + D96E + K98I + D111A + G163K + H198S + Y220F + T231R + N233C |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

31. The composition according to any one of paragraphs 10-27, comprising linear alkylbenzene sulfonate (LAS) and alcohol ethoxylate (AEO) and a lipase variant of any one of paragraphs 1-9, in particular a lipase variant comprising one of the following set of substitutions using SEQ ID NO: 1 for numbering:

| |
|---|
| E1C + H198Y + N233C |
| E1C + H198T + N233C |
| E1C + H198G + N233C |
| E1C + L227F + N233C |
| E1C + E210T + N233C |
| E1C + E210N + N233C |
| E1C + V176M + N233C |
| E1C + K98T + N233C |

-continued

| |
|---|
| E1C + K98E + N233C |
| E1C + E56S + N233C |
| E1C + E56Q + N233C |
| E1C + E56R + N233C |
| E1C + F51M + N233C |
| E1C + D27R + F51Y + N233C |
| E1C + V2I + N233C |
| E1C + V2N + N233C |
| E1C + V2K + N233C |
| E1C + V2A + N233C |
| E1C + D96L + N233C |
| E1C + L69R + N233C |
| E1C + V2Y + N233C |
| E1C + N233C + P256T |
| E1C + N233C + D254S |
| E1C + T231R + N233C |
| E1C + H198S + N233C |
| E1C + D111A + N233C |
| E1C + D96E + N233C |
| E1C + G38A + N233C |
| E1C + N33Q + N233C |
| E1C + N33K + N233C |
| E1C + V176L + N233C |
| E1C + E56K + N233C |
| E1C + E210A + N233C |
| E1C + E210Q + N233C |
| E1C + E210R + N233C |
| E1C + K98R + N233C |
| E1C + K98V + N233C |
| E1C + F51L + N233C |
| E1C + F51I + N233C |
| E1C + L227G + N233C |
| E1C + E210K + N233C |
| E1C + K98Q + N233C |
| E1C + Y220F + N233C |
| E1C + H198L + N233C |
| E1C + H198G + N233C |
| E1C + L69V + N233C |
| E1C + L69T + N233C |
| E1C + L69S + N233C |
| E1C + L69H + N233C |
| E1C + L69F + N233C |
| E1C + L69C + N233C |
| E1C + K237C |
| E1C + K98I + N233C |
| E1C + D27R + F51I + E56R + K98E + T231R + N233C |
| E1C + D27R + F51I + E56R + K98E + T231R + N233C + D254S |
| E1C + D27R + G38A + F51L + K98I + D111A + G163S + H198S + Y220F + T231R + N233C + P256T |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + F51L + D96E + K98I + D111A + G163S + H198S + Y220F + T231R + N233C + P256T |
| E1C + D27R + F51L + D96E + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + P256T |
| E1C + D27R + F51V + D96E + K98I + D111A + G163K + H198S + Y220F + T231R + N233C + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96E + K98I + D111A + G163S + H198S + Y220F + T231R + N233C + P256T |
| E1C + G38A + F51V + D96E + K98I + D111A + G163K + H198S + Y220F + T231R + N233C + P256T |
| E1C + F51V + D96E + K98I + D111A + G163K + H198S + Y220F + T231R + N233C + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + D27R + N33K + G38A + F51V + D96E + K98I + D111A + G163K + H198S + Y220F + T231R + N233C |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

32. The composition according to any one of paragraphs 10-27, comprising linear alkylbenzene sulfonate (LAS) and alcohol ethoxylate (AEO) and a lipase variant of any one of paragraphs 1-9, in particular a lipase variant comprising one of the following set of substitutions using SEQ ID NO: 1 for numbering:

E1C + H198Y + N233C
E1C + L227F + N233C
E1C + E210T + N233C
E1C + E210N + N233C
E1C + V176M + N233C
E1C + K98T + N233C
E1C + K98E + N233C
E1C + E56S + N233C
E1C + E56Q + N233C
E1C + E56R + N233C
E1C + F51M + N233C
E1C + D27R + F51Y + N233C
E1C + V2I + N233C
E1C + V2N + N233C
E1C + V2K + N233C
E1C + V2A + N233C
E1C + D96L + N233C
E1C + L69R + N233C
E1C + V2Y + N233C
E1C + N233C + P256T
E1C + N233C + D254S
E1C + T231R + N233C
E1C + D111A + N233C
E1C + G38A + N233C
E1C + N33Q + N233C
E1C + N33K + N233C
E1C + V176L + N233C
E1C + E56K + N233C
E1C + E210A + N233C
E1C + E210Q + N233C
E1C + E210R + N233C
E1C + K98R + N233C
E1C + K98V + N233C
E1C + F51L + N233C
E1C + F51I + N233C
E1C + E210K + N233C
E1C + K98Q + N233C
E1C + Y220F + N233C
E1C + H198L + N233C
E1C + L69V + N233C
E1C + L69T + N233C
E1C + L69S + N233C
E1C + L69H + N233C
E1C + L69F + N233C
E1C + L69C + N233C
E1C + K237C
E1C + K98I + N233C
E1C + D27R + F51I + E56R + K98E + T231R + N233C
E1C + D27R + F51I + E56R + K98E + T231R + N233C + D254S
E1C + D27R + G38A + F51L + K98I + D111A + G163S + H198S + Y220F + T231R + N233C + P256T
E1C + D27R + G38A + F51L + D96E + K98I + D111A + G163K + H198S + Y220F + T231R + N233C + D254S + P256T
E1C + D27R + G38R + F51L + D96E + K98I + D111A + G163K + H198S + Y220F + T231R + N233C + D254S + P256T
E1C + D27R + F51L + D96I + K98I + D111A + G163K + H198S + Y220F + T231R + N233C + P256T
E1C + D27R + F51L + D96E + K98I + D111A + G163S + H198S + Y220F + T231R + N233C + P256T
E1C + D27R + F51L + D96E + K98I + D111A + G163K + H198S + Y220F + T231R + N233C + P256T
E1C + D27R + G38A + F51I + D96E + K98I + D111A + G163K + H198S + Y220F + T231R + N233C + D254S + P256T
E1C + D27R + G38A + F51V + D96E + K98I + D111A + G163K + H198S + Y220F + T231R + N233C + P256T
E1C + D27R + F51V + D96E + K98I + D111A + G163K + H198S + Y220F + T231R + N233C + P256T
E1C + D27R + F51V + D96E + K98I + D111A + G163S + H198S + Y220F + T231R + N233C + D254S + P256T
E1C + D27R + F51V + D96I + K98I + D111A + G163K + H198S + Y220F + T231R + N233C + D254S + P256T
E1C + D27R + F51V + K98I + D111A + G163K + H198S + Y220F + T231R + N233C + D254S + P256T
E1C D27R F51V D96E K98I D111A G163K H198S Y220F T231R N233C D254S P256T
E1C + D27R G38A F51V D96E K98I D111A G163K H198S Y220F T231R N233C D254S P256T
E1C + F51V D96E K98I D111A G163S H198S Y220F T231R N233C P256T
E1C + G38A + F51V + D96E + K98I + D111A + G163K + H198S + Y220F + T231R + N233C + P256T
E1C + F51V + D96E + K98I + D111A + G163K + H198S + Y220F + T231R + N233C + P256T
E1C + F51V + D96I + K98I + D111A + G163K + H198S + Y220F + T231R + N233C + D254S + P256T
E1C + F51V + K98I + D111A + G163K + H198S + Y220F + T231R + N233C + D254S + P256T
E1C + F51I + D96E + K98I + D111A + G163K + H198S + Y220F + T231R + N233C + D254S + P256T
E1C + D27R + F51L + D96E + K98I + D111A + G163K + H198S + Y220F + T231R + N233C + D254S + P256T
E1C + D27R + N33K + G38A + F51V + D96E + K98I + D111A + G163K + H198S + Y220F + T231R + N233C
E1C + G38R + F51V + D96E + K98I + D111A + G163K + H198S + Y220F + T231R + N233C + D254S + P256T
E1C + F51V + D96E + K98I + D111A + G163K + H198S + Y220F + T231R + N233C + D254S + P256T
E1C + G38A + F51V + D96E + K98I + D111A + G163K + H198S + Y220F + T231R + N233C + D254S + P256T
E1C + D27R + G38R + F51V + D96E + K98I + D111A + G163K + H198S + Y220F + T231R + N233C + D254S + P256T

33. The composition according to any one of paragraphs 10-32 further comprising a builder, in particular a chelating agent, such as EDTA, in particular in a concentration between 0.001 and 100 mW such as between 0.01 and 10 mW such as 0.1-5 mM.

34. The composition according to paragraphs 33 for use is in cleaning where the resulting water hardness is between 0 and 30° dH, such as between 0 and 15° dH, such as between 0 and 10° dH, such as between 3 and 20° dH, such as between 10 and 20° dH, or such as above 20° dH.

35. The composition according to paragraphs 33 or 34, comprising linear alkylbenzene sulfonate (LAS), alcohol ethoxylate (AEO) and a chelating agent, such as EDTA, and a lipase variant of any one of paragraphs 1-9, in particular a lipase variant comprising one of the following set of substitutions using SEQ ID NO: 1 for numbering:

| |
|---|
| E1C + E210T + N233C |
| E1C + E210N + N233C |
| E1C + E56R + N233C |
| E1C + D96L + N233C |
| E1C + N233C + D254S |
| E1C + E56K + N233C |
| E1C + E210A + N233C |
| E1C + E210Q + N233C |
| E1C + E210R + N233C |
| E1C + E210K + N233C |
| E1C + D27R + F51I + E56R + K98E + T231R + N233C |
| E1C + D27R + F51I + E56R + K98E + T231R + N233C + D254S |
| E1C + D27R + G38A + F51L + D96E + K98I + D111A + G163K + H198S + Y220F + T231R + N233C + D254S + P256T |
| E1C + D27R + G38R + F51L + D96E + K98I + D111A + G163K + H198S + Y220F + T231R + N233C + D254S + P256T |
| E1C + D27R + F51L + D96I + K98I + D111A + G163K + H198S + Y220F + T231R + N233C + P256T |
| E1C + D27R + G38A + F51I + D96E + K98I + D111A + G163K + H198S + Y220F + T231R + N233C + D254S + P256T |
| E1C + D27R + F51V + D96E + K98I + D111A + G163S + H198S + Y220F + T231R + N233C + D254S + P256T |
| E1C + D27R + F51V + D96I + K98I + D111A + G163K + H198S + Y220F + T231R + N233C + D254S + P256T |
| E1C + D27R + F51V + K98I + D111A + G163K + H198S + Y220F + T231R + N233C + D254S + P256T |
| E1C + D27R + F51V + D96E + K98I + D111A + G163K + H198S + Y220F + T231R + N233C + D254S + P256T |
| E1C + D27R + G38A + F51V + D96E + K98I + D111A + G163K + H198S + Y220F + T231R + N233C + D254S + P256T |
| E1C + F51V + D96I + K98I + D111A + G163K + H198S + Y220F + T231R + N233C + D254S + P256T |
| E1C + F51V + K98I + D111A + G163K + H198S + Y220F + T231R + N233C + D254S + P256T |
| E1C + F51I + D96E + K98I + D111A + G163K + H198S + Y220F + T231R + N233C + D254S + P256T |
| E1C + D27R + F51L + D96E + K98I + D111A + G163K + H198S + Y220F + T231R + N233C + D254S + P256T |
| E1C + G38R + F51V + D96E + K98I + D111A + G163K + H198S + Y220F + T231R + N233C + D254S + P256T |
| E1C + F51V + D96E + K98I + D111A + G163K + H198S + Y220F + T231R + N233C + D254S + P256T |
| E1C + G38A + F51V + D96E + K98I + D111A + G163K + H198S + Y220F + T231R + N233C + D254S + P256T |
| E1C + D27R + G38R + F51V + D96E + K98I + D111A + G163K + H198S + Y220F + T231R + N233C + D254S + P256T |

36. The composition according to any one of paragraphs 10-35, comprising linear alkylbenzene sulfonate (LAS) and alcohol ethoxylate (AEO) and a lipase variant of any one of paragraphs 1-9, in particular a lipase variant comprising one of the following set of substitutions using SEQ ID NO: 1 for numbering:

| |
|---|
| E1C + H198Y + N233C |
| E1C + H198T + N233C |
| E1C + H198G + N233C |
| E1C + H198S + N233C |
| E1C + H198L + N233C |
| E1C + H198G + N233C |

37. The composition according to any one of paragraphs 10-36, wherein said composition further comprises at least one additional enzyme, such as an amylase, protease, cellulase, another lipase, beta-glucanase, and/or mannanase.

38. The composition according to paragraph 37, wherein said at least one additional enzyme is an alpha-amylase variant comprising an modification in one or more positions corresponding to positions H1, N54, V56, K72, G109, F113, R116, T134, W140, W159, W167, Q169, Q172, L173, A174, R181, G182, 0183, G184, W189, E194, N195, V206, G255, N260, F262, A265, W284, F289, G304, G305, W347, K391, Q395, W439, W469, R444, F473, G476, and G477 of SEQ ID NO: 1, wherein said alpha-amylase variant has a sequence identity of at least 75% but less than 100% to SEQ ID NO: 2 and wherein said alpha-amylase variant has alpha-amylase activity.

39. The composition according to paragraph 38, wherein said alpha-amylase variant is selected from the group consisting of:

H1*+N54S+V56T+G109A+Q169E+Q172K+A174*+G182*+D183*+N195F+V206L+K391A+G476K;

H1*+N54S+V56T+G109A+R116H+A174S+G182*+D183*+N195F+V206L+K391A+G476K;

H1*+N54S+V56T+K72R+G109A+F113Q+R116Q+W167F+Q172G+A174S+G182*+D183*+G184T+N195F+V206L+K391A+P473R+G476K;

H1*+N54S+V56T+G109A+F113Q+R116Q+Q172N+A174S+G182*+D183*+N195F+V206L+A265G+K391A+P473R+G476K;

H1*+N54S+V56T+K72R+G109A+F113Q+W167F+Q172R+A174S+G182*+D183*+N195F+V206L+K391A+G476K;

H1*+N54S+V56T+K72R+G109A+R116H+T134E+W167F+Q172G+L173V+A174S+G182*+D183*+N195F+V206L+G255A+K391A+G476K;

H1*+N54S+V56T+K72R+G109A+R116H+T134E+W167F+Q172G+L173V+A174S+G182*+D183*+N195F+V206L+G255A+K391A+Q395P+T444Q+P473R+G476K;

H1*+N54S+V56T+G109A+T134E+A174S+G182*+D183*+N195F+V206L+K391A+G476K;

H1*+N54S+V56T+K72R+G109A+A174S+G182*+D183*+N195F+V206L+G255A+K391A+G476K; and

H1*+N54S+V56T+G109A+W167F+Q172E+L173P+A174K+G182*+D183*+N195F+V206L+K391A+G476K.

40. The composition according to paragraph 37, wherein said at least one additional enzyme is a protease having protease activity, wherein said protease is selected from the group of:
a) a protease having a sequence identity of at least 70%, such as at least 75%, such as at least 80%, such as at least 85%, such as at least 90%, such as at least 95%, such as at least 98%, such as at least 99%, such as 100%, to the sequences of SEQ ID NOs: 4, 5, or 6;
b) a protease variant comprising a substitution at one or more positions corresponding to positions 171, 173, 175, 179, or 180 of SEQ ID NO: 7, wherein said protease variant has a sequence identity of at least 75% but less than 100% to SEQ ID NO: 7; and
c) a protease variant comprising a modification in one or more positions corresponding to positions 32, 33, 48, 49, 50, 51, 52, 53, 54, 58, 59, 60, 61, 62, 94, 95, 96, 97, 98, 99, 100, 101, 102, 103, 104, 105, 106, 107, 116, 123, 124, 125, 126, 127, 128, 129, 130, 131, 132, 133, 150, 152, 153, 154, 155, 156, 158, 159, 160, 161, 164, 169, 175, 176, 177, 178, 179, 180, 181, 182, 183, 184, 185, 186, 197, 198, 203, 204, 205, 206, 207, 208, 209, 210, 211, 212, 213, 214, 215, and 216 as compared with the protease in SEQ ID NO:3, wherein said protease variant has at least 75% sequence identity to SEQ ID NO: 4.
41. The composition according to paragraph 40, wherein said protease is that of (a).
42. The composition according to paragraph 40, wherein said protease is that of (b).
43. The composition according to any one of paragraphs 37 or 39, wherein said protease is said variant in (b) comprising a substitution in at least one position corresponding to positions 171, 173, 175, 179, or 180, and wherein the amino acid in the position corresponding to position 171 of SEQ ID NO: 7 is selected from the group consisting of W, K, E, D and N; and/or the amino acid in the position corresponding to position 173 of SEQ ID NO: 7 is P; and/or the amino acid in the position corresponding to position 175 of SEQ ID NO: 7 is selected from the group consisting of A, V, and P; and/or the amino acid in the position corresponding to position 179 of SEQ ID NO: 7 is selected from the group consisting of C, V, Q, S, T, E, H, K, M, N, Y, and A; and/or the amino acid in the position corresponding to position 180 of SEQ ID NO: 7 is Y.
44. The composition according to paragraph 40, wherein said protease is that of (c).
45. The composition according to any one of paragraph 37 or 40, wherein said protease is said variant in (c) comprises one or more of the following substitutions; S9E, S9R, A15T, K27R, N42R, G52S, S55P, T56P, G59D, G59E, N60D, N60E, V66A, N74D, S85N, S85R, S97A, S97E, S97D, S99E, S99D, S99G, S99N, S99H, S99M, S101A, V1021, V102N, S104A G116V, G116R, S154D, A156E, G157S, G157D, G157P, S158E, Y161A, R164S, Q176E, N179E, S182E, Q185N, A188P, N198D, V1991, Q200L, Y203W, S206G, S210V, L211D, L211Q, L211E, N212D, N212E, N212S, M216S, M216A, Q230H, Q239R, N242D, S250D, S253D, N255W, N255D, N255E, L256E, L256D, and R269H, wherein numbering is according to SEQ ID NO: 4.
46. The composition according to any one of paragraphs 10-45, wherein the number of modifications in said lipase variant is 1 to 20, e.g., 1 to 10, such as 1, 2, 3, 4, 5, 6, 7, 8, 9, or 10 modifications.
47. The composition according to any one of paragraphs 10-46, wherein said composition further comprises at least one chelating agent; and/or at least one polymer; and/or at least one hydrotrope; and/or at least one builder and/or co-builder; and/or at least one perfume; and/or at least one kind of bleaching system.
48. The composition according to any one of paragraphs 10-47, wherein said composition is a detergent composition or an adjunct composition.
49. The composition according to paragraph 48, wherein said detergent composition is a liquid laundry detergent composition or a powder laundry detergent composition.
50. The composition according to paragraph 49, wherein said adjunct composition is a pre-treatment composition, a soaking composition, or a boosting composition.
51. Use of the composition according to any one of paragraphs 10-50 in laundry or industrial cleaning.
52. Use of the composition according to any one of paragraphs 10 to 51, wherein said use is in a laundry process where the resulting water hardness is between 0 and 30° dH, such as between 0 and 15° dH, such as between 0 and 10° dH, such as between 3 and 20° dH, such as between 10 and 20° dH, or such as above 20° dH.
53. Use of the composition according to any one of paragraphs 10-52, wherein said use is in a laundry process where the wash cycle is less than 360 minutes, such as less than 280 minutes, such as less than 150 minutes, such as less than 100 minutes, such as less than 50 minutes, such as less than 30 minutes, such as less than 15 minutes, or such as less than 10 minutes.
54. Use of the composition according to paragraph 53, wherein the concentration of said surfactant during said laundry process is at least 0.005 g/L wash water, such as at least 0.007 g/L, such as at least 0.01 g/L, or such as at least 0.1 g/L, or such as least 1 g/L, such as at least 2 g/L, such as at least 3 g/L, or such as 4 g/L wash water, or in the range from between 0.05-10 g/L wash water, such as between 0.1-8 g/L, such as between 0.1-6 g/L, or such as between 0.2-6 g/L wash water.
55. A method of laundering, comprising laundering a fabric with a composition according to any one of paragraphs 10-50, preferably at a temperature of 50° C. or less, or more preferably at a temperature of 40° C. or less, or more preferably at a temperature of 30° C. or less, or even more preferably at a temperature of 20° C. or less.
56. A method of pre-treating a fabric with a composition according to any one of paragraphs 10-50, comprising the steps of adding said composition to said fabric, and leaving the composition on the fabric for a period of time, and rinsing off said composition from said fabric.

The present invention is further described by the following examples that should not be construed as limiting the scope of the invention.

EXAMPLES

Example 1—Assays p-Nitrophenyl (PNP) Assay (General Lipase Activity Assay):

The hydrolytic activity of a lipase may be determined by a kinetic assay using p-nitrophenyl acyl esters as substrate.

A 100 mM stock solution in DMSO of the substrates: p-Nitrophenyl butyrate (C4), p-Nitrophenyl caproate (C6), p-Nitrophenyl caprate (C10), p-Nitrophenyl laurate (C12) and p-Nitrophenyl palmitate (C16) (all from Sigma-Aldrich Danmark A/S, Kirkebjerg Allé 84, 2605 Brøndby; Cat. no.: C4:N-9876, C6: N-0502, C10: N-0252, C12: N-2002, C16: N-2752) may be diluted to a final concentration of 1 mM 25 into assay buffer (50 mM Tris; pH 7.7; 0.4% TritonX-100).

The lipase of the invention, the parent lipase and appropriate controls e.g. Buffer (negative), Lipolase™ & Lipex™ (positive) in 50 mM Hepes; pH 8.0; 10 ppm TritonX-100; +/−20 mM $CaCl_2$ may be added to the substrate solution in the following final concentrations: 0.01 mg/ml; 5×10−3 mg/ml; 2.5×10−4 mg/ml; and 1.25×10−4 mg/ml in 96-well NUNC plates (Cat. No: 260836, Kamstrupvej 90, DK-4000, Roskilde). Release of p-nitrophenol by hydrolysis of p-nitrophenyl acyl may be monitored at 405 nm for 5 minutes in 10 second intervals on a Spectra max 190 (Molecular Devices GmbH, Bismarckring 39, 88400 Biberach an der Riss, GERMANY). The hydrolytic activity towards one or more substrates of a variant may be compared to that of the parent lipase.

Relative Wash Performance (RP(Wash))

Washing experiments may be performed using Automatic Mechanical Stress Assay (AMSA) in order to assess the wash performance in laundry. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO02/42740 especially the paragraph Special method embodiments (at page 23-24.

The laundry experiments are conducted under the experimental conditions specified below:

TABLE 1

| Experimental conditions | |
|---|---|
| Detergent: | 3.3 g/L Detergent B |
| Test solution volume: | 160 uL |
| Wash time: | 20 minutes |
| Temperature: | 30° C. |
| Lipase dosage: | 0 ppm or 0.35 ppm |
| Test material: | Cream Annatto stained EMPA221 cotton textile prepared as described in WO06/125437 except to exchanging turmeric with annatto (Annatto: A-320-WS, Chr. Hansen A/S, Boege Allé 10-12, DK-2970, Hoersholm, Denmark & EMPA221: EMPA, Lerchenfeldstrasse 5, CH-9014, St. Gallen, Switzerland) |

Water hardness is adjusted to 15° dH by addition of $CaCl_2$, $MgCl_2$ and $NaHCO_3$ ($Ca^{2+}$:$Mg^{2+}$:$HCO_3^-$ = 4:1:7.5).

TABLE 2

| Model detergent B | |
|---|---|
| Composition Detergent B | wt % |
| NaOH, pellets (>99%) | 1.05 |
| Linear alkylbenzene sulfonic acid (LAS) (97%) | 7.20 |
| Sodium laureth sulfate (SLES) (28%) | 10.58 |
| Soy fatty acid (>90%) | 2.75 |
| Coco fatty acid (>99%) | 2.75 |
| Alcohol ethoxylate (AEO) with 8 mol EO; Lutensol TO 8 (~100%) | 6.60 |
| Triethanol amine (100%) | 3.33 |
| Na-citrate, dihydrate (100%) | 2.00 |

TABLE 2-continued

| Model detergent B | |
|---|---|
| Composition Detergent B | wt % |
| DTMPA; diethylenetriaminepentakis(methylene)pentakis(phosphonic acid), heptasodium salt (Dequest 2066 C) (~42% as Na7 salt) | 0.48 |
| MPG (>98%) | 6.00 |
| EtOH, propan-2-ol (90/10%) | 3.00 |
| Glycerol (>99.5) | 1.71 |
| Sodium formate (>95%) | 1.00 |
| PCA (40% as sodium salt) | 0.46 |
| Water up to | 100 |

TABLE 3

| Model detergent A | |
|---|---|
| Compound | Content of active compound (% w/w) |
| LAS | 12.0 |
| AEOS, SLES | 6.6 |
| Soy fatty acid | 2.6 |
| Coco fatty acid | 2.6 |
| AEO | 10.3 |
| Sodium hydroxide | 1.9 |
| Ethanol/Propan-2-ol | 2.5/0.3 |
| MPG | 11.9 |
| Glycerol | 1.9 |
| TEA | 2.8 |
| Sodium formate | 0.9 |
| Sodium citrate | 1.9 |
| DTMPA (as $Na_7$-salt) | 0.06 |
| PCA (as Na-salt) | 0.17 |
| Ion exchanged water | 38.1 |

Water hardness may be adjusted to 15° dH by addition of CaCl2, MgCl2 and NaHCO3 ($Ca^{2+}$:$Mg^{2+}$:$HCO3^-$ = 4:1:7.5) to the test system.
After washing the textiles are flushed in tap water and dried.

TABLE 4

| Model detergent X | | |
|---|---|---|
| Compound | Content of compound (% w/w) | Active component (% w/w) |
| LAS | 16.5 | 91 |
| AEO* | 2 | 99.5 |
| Sodium carbonate | 20 | 100 |
| Sodium (di)silicate | 12 | 82.5 |
| Zeolite A | 15 | 80 |
| Sodium sulfate | 33.5 | 100 |
| PCA | 1 | 100 |

*Model detergent X is mixed without AEO. AEO is added separately before wash.
Water hardness may be adjusted to 12 °dH by addition of CaCl2, MgCl2, and NaHCO3 ($Ca^{2+}$:$Mg^{2+}$:$HCO3^-$ = 2:1:4.5) to the test system. After washing the textiles are flushed in tap water and dried.

TABLE 5

| Model detergent Z | | |
|---|---|---|
| Compound | Content of compound (% w/w) | % active component (% w/w) |
| LAS | 7.0 | 85.3 |
| Soap | 1.1 | 93 |
| AEO* | 1.5 | 99.5 |
| Soda ash | 20.1 | 99.5 |
| Hydrous sodium silicate | 10.0 | 80.1 |
| Zeolite A | 5.0 | 80 |
| Sodium citrate | 2.0 | 100 |

TABLE 5-continued

| Model detergent Z | | |
|---|---|---|
| Compound | Content of compound (% w/w) | % active component (% w/w) |
| $HEDP-Na_4$ | 0.2 | 84 |
| Polyacrylate | 1.1 | 92 |
| Sodium sulfate | 52.0 | 100 |

*Model detergent Z is mixed without AEO. AEO is added separately before wash.
Water hardness may be adjusted to 15° dH by addition of CaCl2, MgCl2, and NaHCO3 ($Ca^{2+}$:$Mg^{2+}$:$HCO3^-$ = 4:1:7.5) to the test system.
After washing the textiles are flushed in tap water and dried.
pH was adjusted with 4M NaOH.

TABLE 6

| Model detergent Z with bleach | | |
|---|---|---|
| Compound | Content of compound (% w/w) | % active component (% w/w) |
| LAS | 7.0 | 85.3 |
| Soap | 1.1 | 93 |
| AEO* | 1.5 | 99.5 |
| Soda ash | 20.1 | 99.5 |
| Hydrous sodium silicate | 10.0 | 80.1 |
| Zeolite A | 5.0 | 80 |
| Sodium citrate | 2.0 | 100 |
| $HEDP-Na_4$ | 0.2 | 84 |
| Polyacrylate | 1.1 | 92 |
| Sodium percarbonate | 9.3 | 86 |
| TEAD | 1.1 | 91.8 |
| Sodium sulfate | 41.6 | 100 |

*Model detergent Z is mixed without AEO. AEO is added separately before wash.

TABLE 7

| Model detergent A' | |
|---|---|
| Compound | Content of active compound (% w/w) |
| LAS | 11.6 |
| AEOS, SLES | 4.9 |
| Soy fatty acid | 2.7 |
| Coco fatty acid | 2.8 |
| AEO | 11 |
| Sodium hydroxide | 1.8 |
| Ethanol/Propan-2-ol | 2.7/0.3 |
| MPG | 6 |
| Glycerol | 1.7 |
| TEA | 3.3 |
| Sodium formate | 1 |
| Sodium citrate | 2 |
| DTMPA (as $Na_7$-salt) | 0.2 |
| PCA (as Na-salt) | 0.18 |
| Ion exchanged water | 33.6 |

Water hardness may be adjusted to 15° dH by addition of CaCl2, MgCl2, and NaHCO3 ($Ca^{2+}$:$Mg^{2+}$:$HCO3^-$ = 4:1:7.5) to the test system.
After washing the textiles are flushed in tap water and dried.

After washing the textiles are flushed in tap water and excess water was removed from the textiles using filter paper and immediately thereafter the textiles are dried at 100° C. for 15 minutes.

The wash performance is measured as the color change of the washed soiled textile. The soil may be cream mixed with annatto. Annatto contains the colorant norbixin, which function as a pH indicator by having pH dependent color change. Lipase activity leads to release of free fatty acids from the cream acylglycerols and this leads to pH decrease and thereby color change of the norbixin pH indicator. Lipase wash performance can therefore be expressed as the extent of color change of light reflected-emitted from the washed soiled textile when illuminated with white light.

Color measurements are made with a professional flatbed scanner (EPSON EXPRESSION 10000XL, Atea A/S, Lautrupvang 6, 2750 Ballerup, Denmark), which is used to capture an image of the washed soiled textile. To extract a value for the light intensity from the scanned images, 24-bit pixel values from the image were converted into values for red, green and blue (RGB).

Color change due to lipase activity was measured as the change in the reflection-emitting of green light (G) relative to the light intensity value (Int) calculated as:

$$Int=\sqrt{R^2+G^2+B^2}$$

The relative wash performance (RP(Wash)) of a lipase relative to a reference lipase was calculated as:

$$RP(Wash)=(G/Int(variant)-G/Int(no\ enzyme))/(G/Int(lipase\ ref.)-G/Int(no\ enzyme)).$$

A lipase is considered to exhibit improved wash performance, if it performs better than the reference (RP (Wash)>1). In the context of the present invention the reference enzyme is a lipase having a single amino acid substitution relative to the tested lipase.

Odor Detection by Solid Phase Micro Extraction Gas Chromatograph Measurements.

The butyric acid release (odor) from the lipase washed swatches are measured by Solid Phase Micro Extraction Gas Chromatography (SPME-GC) using the following method.

Cream Annatto stained EMPA221 cotton textile is washed as specified above and after wash, excess water is removed from the textile using filter paper and the textile is thereafter dried at 25° C. for 2 h. Each SPME-GC measurement was performed with four pieces of the washed and dried textile (5 mm in diameter), which are transferred to a Gas Chromatograph (GC) vial and the vial was closed. The samples are incubated at 30° C. for 24 hours and subsequently heated to 140° C. for 30 minutes and stored at 20° C.-25° C. for at least 4 hours before analysis. The analyses are performed on a Varian 3800 GC equipped with a Stabilwax-DA w/Integra-Guard column (30m, 0.32 mm ID and 0.25 um df) and a Carboxen PDMS SPME fiber (85 micro-m). Sampling from each GC vial is done at 50° C. for 8 minutes with the SPME fiber in the head-space over the textile pieces and the sampled compounds are subsequently injected onto the column (injector temperature=250° C.). Column flow=2 ml helium/minute. Column oven temperature gradient: 0 minute=50° C., 2 minutes=50° C., 6 minutes 45 seconds=240° C., 11 minutes 45 seconds=240° C. Detection is done using a Flame Ionization Detector (FID) and the retention time for butyric acid is identified using an authentic standard.

The relative odor release (RP(Odor)) of a lipase is the ratio between the amount butyric acid released (peak area) from a lipase washed swatch and the amount butyric acid released (peak area) from a reference lipase washed swatch, after both values will be corrected for the amount of butyric acid released (peak area) from a non-lipase washed swatch (blank). The reference lipase is a polypeptide having a single amino acid substitution relative to the tested lipase. The relative odor performance (RP(Odor)) of the polypeptide is calculated in accordance with the below formula:

$$RP(Odor)=(odor(variant)-odor(no\ enzyme))/(odor(lipase\ ref.)-odor(no\ enzyme))$$

Where odor is the measured butyric acid (peak area) released from the textile surface.

Alpha-Amylase Activity Assay—pNP-G7 Assay

The alpha-amylase activity may be determined by a method employing the G7-pNP substrate. G7-pNP which is an abbreviation for 4,6-ethylidene($G_7$)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm.). Kits containing G7-pNP substrate and alpha-Glucosidase is manufactured by Roche/Hitachi (cat. No. 11876473).

Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use. Dilution buffer: 50 mM MOPS, 0.05% (w/v) Triton X100 (polyethylene glycol p-(1,1,3,3-tetramethylbutyl)-phenyl ether ($C_{14}H_{22}O(C_2H4O)_n$ (n=9-10))), 1 mM $CaCl_2$, pH8.0.

Procedure:

The amylase sample to be analyzed is diluted in dilution buffer to ensure the pH in the diluted sample is 7. The assay is performed by transferring 20 μl diluted enzyme samples to 96 well microtiter plate and adding 80 μl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Alpha-Amylase Activity Assay—Phadebas Activity Assay

The alpha-amylase activity may also be determined by a method using the Phadebas substrate (from for example Magle Life Sciences, Lund, Sweden). A Phadebas tablet includes interlinked starch polymers that are in the form of globular microspheres that are insoluble in water. A blue dye is covalently bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The concentration of blue is proportional to the alpha-amylase activity in the sample.

The alpha-amylase sample to be analyzed is diluted in activity buffer with the desired pH. Two substrate tablets are suspended in 5 mL activity buffer and mixed on magnetic stirrer. During mixing of substrate transfer 150 μl to microtiter plate (MTP) or PCR-MTP. Add 30 μl diluted amylase sample to 150 μl substrate and mix. Incubate for 15 minutes at 37° C. The reaction is stopped by adding 30 μl 1M NaOH and mix. Centrifuge MTP for 5 minutes at 4000×g. Transfer 100 μl to new MTP and measure absorbance at 620 nm.

The alpha-amylase sample should be diluted so that the absorbance at 620 nm is between 0 and 2.2, and is within the linear range of the activity assay.

Alpha-Amylase Activity Assay—Amylazyme Activity Assay

The alpha-amylase activity may also be determined by a method using the Amylazyme substrate (Megazyme® Amylazyme Test, supplied by Megazyme for the assay of cereal and bacterial amylases) comprising AZCL-amylose, which has been mixed with lactose and magnesium stearate and tabletted. A blue dye is covalently bound to these microspheres. The interlinked amylose polymers in the microsphere are degraded at a speed that is proportional to the alpha-amylase activity. When the alpha-amylase degrades the starch polymers, the released blue dye is water soluble and concentration of dye may be determined by measuring absorbance at 590 nm. The concentration of blue is proportional to the alpha-amylase activity in the sample.

The alpha-amylase sample to be analyzed is diluted in activity buffer with the desired pH. Two substrate tablets are suspended in 5 mL activity buffer and mixed on magnetic stirrer. During mixing of substrate 150 μl is transferred to a microtiter plate (MTP) or PCR-MTP. Next, 25 μl diluted amylase sample is added to 150 μl substrate and mixed. The mixture is incubated for 10 minutes at 37° C. The reaction is stopped by adding 25 μl 1M NaOH and mixed. MTP is centrifuged for 5 minutes at 4000×g, followed by transferring 100 μl to a new MTP and absorbance is measured at 590 nm.

Protease Activity Assays:

1) Suc-AAPF-pNA Activity Assay:

The proteolytic activity can be determined by a method employing the Suc-AAPF-PNA substrate. Suc-AAPF-PNA is an abbreviation for N-Succinyl-Alanine-Alanine-Proline-Phenylalanine-p-Nitroanilide, and it is a blocked peptide which can be cleaved by endo-proteases. Following cleavage a free PNA molecule is liberated and it has a yellow colour and thus can be measured by visible spectrophotometry at wavelength 405 nm. The Suc-AAPF-PNA substrate is manufactured by Bachem (cat. no. L1400, dissolved in DMSO).

The protease sample to be analyzed was diluted in residual activity buffer (100 mM Tris pH8.6). The assay was performed by transferring 60 μl of diluted enzyme samples to 96 well microtiter plate and adding 140 μl substrate working solution (0.72 mg/ml in 100 mM Tris pH8.6). The solution was mixed at room temperature and absorption is measured every 20 sec. over 5 minutes at OD 405 nm.

The slope (absorbance per minute) of the time dependent absorption-curve is directly proportional to the specific activity (activity per mg enzyme) of the protease in question under the given set of conditions. The protease sample should be diluted to a level where the slope is linear.

Assay for Measurement of Free Calcium Ions

The following assay may be used for the measurement of free calcium ions in solution, and thus for the determination of chelating agents (chelants) ability to reduce the concentration of free calcium ions ($Ca^{2+}$) from e.g. 2.0 mM to 0.10 mM at pH 8.

Assay Principle:

Various amounts of chelants are added to a solution of 2.0 mM $Ca^{2+}$ and the free $Ca^{2+}$ concentration is determined by using a Calcium Ion Selective Electrode at fixed pH and temperature. The concentration of chelant necessary to reduce the concentration of free calcium from 2.0 mM to 0.10 mM can be determined from a plot of the free calcium concentration measured versus the concentration of chelant.

In the present assay the concentration of chelant necessary to reduce the concentration of free calcium from 2.0 mM to 0.10 mM is measured at pH 8, at 21° C., in potassium chloride and 49 mM EPPS.

Solutions:

Electrolyte solution: 4 M potassium chloride in ultrapure water (Milli-Q water). pH 8 buffer: 50 mM EPPS (4-(2-Hydroxyethyl)piperazine-1-propanesulfonic acid) adjusted to pH 8.0 using minimum amounts of 1 N sodium hydroxide.

Calcium stock solution: 25 mM $Ca^{2+}$ in pH 8 buffer, made from $CaCl_2.2H_2O$.

Chelant stock solution: 15 mM chelant (on a 100% dry chelator basis) in pH 8 buffer, re-adjusted to pH 8.0 using minimum amounts of 1 M NaOH or 1 M HCl.

Ultra pure water (Milli Q water) is used for preparation of all buffers and solutions.

Equipment:

Calcium Ion Selective Electrode from Thermo Scientific (cat. No. 9720BNWP) calibrated against a Calcium chloride standard solution. The electrode is calibrated as described by the guidelines following the electrode.

Procedure:

A series of vials are prepared, each containing 4 mL of the calcium stock solution (final concentration 2.0 mM), 1 mL electrolyte solution (final concentration 80 mM potassium chloride), chelant stock solution in various amounts (0-45 mL) and using the pH 8 buffer for adjusting the total volume to 50 mL. The final concentration of EPPS in the assay is 49 mM. ° mM free calcium ions to a value below 0.10 mM or the final chelant concentration in the assay is higher than 10.0 mM. A suitable number of data points are 8 or more. The chelant concentration required to lower the initial 2.0 mM free calcium ions to 0.10 mM is obtained from a plot of the measured free calcium ion concentration versus chelator concentration by interpolation.

The solutions are equilibrated to the desired temperature, which in the present assay is 21° C.

Example 2

Fermentation of *Aspergillus Oryzae* Transformants Expressing *Thermomyces Lanuginosus* Lipase Variants of the Invention Shake flasks containing 200 ml MDU2 (see WO 1995017513 A1) were inoculate with the desired transformants. The shake flasks were grown for 150 hours shaking at 200 RPM at 30° C. The culture broths were passed on for testing.

Example 3

Flocculation and Centrifugation of Culture Broth Prior to Lipase Activity Testing Aliquots of 40 mL culture broths were flocculated with 0.8 mL Aluminium chlorohydrate solution (Magnasol 4710 G from BASF, 30-60%), followed by centrifugation for 10 minutes at 13,000 rpm at 5° C. The supernatants were filtered through 0.45 µm sterile filter (Minisart NML, hydrophile from Sartorius) and stored at −20° C. until use.

Example 4

Lipase Activity Assay with pNP-Acyl Ester Substrate

This experiment was carried out to determine the lipase activity of lipase variants in the presence of one or more surfactants and other agents (see 'Surfactant solutions" table below) as a model for wash relevant conditions.

Principle: Enzyme samples were incubated with pNP-acyl ester (pNP-palmitate or -valerate) in detergent solution of desired composition and water hardness at pH 8.0. The hydrolysis the substrate by the lipase generated p-nitrophenol, the formation of which was be followed spectrophotometrically at 405 nm. The rate of formation of p-nitrophenol is a measure of the lipase activity after correction for blank.

Lipase reference: *Thermomyces lanuginosus* lipase shown as SEQ ID NO: 1 (LIPOLASE™)

Chemicals:

- HEPES (2-[4-(2-hydroxyethyl)-1-piperazinyl]-ethanesulfonic acid),
- pNP-palmitate
- pNP-valerate
- AEO: alcohol ethoxylate, Bio-soft N25-7 from Stepan (average Mw 516 g/mol)
- LAS: Sodium alkylbenzene sulfonate; Thonyl P 85 from Unger Fabrikker, Norway (average Mw 286 g/mol)
- AEOS: Sodium lauryl ether sulfate, SLES 28 from Danlind/Linds (Denmark), (average Mw 385 g/mol)
- EDTA: ethylenediaminetetraacetic acid (or 2,2',2",2'"-(Ethane-1,2-diyldinitrilo)tetraacetic acid), Titriplex III
- $CaCl_2·2H_2O$
- NaOH: sodium hydroxide
- Ethanol: ≥99.5% ethylalcohol Reagents:

- HEPES buffer: 56 mM HEPES prepared with ultrapure water (Milli-Q water), adjusted to pH 8.5 with 1 M NaOH
- pNP-palmitate stock solution: 10 mM pNP-palmitate in ethanol
- pNP-palmitate working solution: 0.33 mM pNP-palmitate in Surfactant solution
- pNP-valerate stock solution: 62.7 mM in ethanol
- pNP-valerate working solution: 0.33 mM in Surfactant solution
- Lipase dilution solution: 0.1 mM AEO
- LAS stock solution: 50 mM LAS
- AEOS stock solution: 50 mM AEOS
- AEO stock solution: 50 mM AEO
- EDTA stock solution: 100 mM
- Surfactant solutions Surfactant solutions

| Assay type | LAS 1.91 mM | AEOS 1.96 mM | LAS:AEO 1.9 mM | LAS:AEO 0.49 mM | LAS:AEO 0.19 mM | LAS:AEO 1.9 mM EDTA | LAS:AEO 1.9 mM |
|---|---|---|---|---|---|---|---|
| Surfactant solution name | A | B | C | D | E | F | G |
| Substrate | pNP-palmitate | pNP-valerate | pNP-palmitate | pNP-palmitate | pNP-palmitate | pNP-palmitate | pNP-valerate |
| Detergent 1 | LAS | AEOS | LAS | LAS | LAS | LAS | LAS |
| Detergent 2 | | | AEO | AEO | AEO | AEO | AEO |

-continued

| Surfactant solutions | | | | | | | |
|---|---|---|---|---|---|---|---|
| Assay type | LAS 1.91 mM | AEOS 1.96 mM | LAS:AEO 1.9 mM | LAS:AEO 0.49 mM | LAS:AEO 0.19 mM | LAS:AEO 1.9 mM EDTA | LAS:AEO 1.9 mM |
| Detergent conc 1 | 1.91 mM | 1.96 mM | 1.28 mM | 0.32 mM | 0.13 mM | 1.28 mM | 1.28 mM |
| Detergent conc 2 | | | 0.64 mM | 0.17 mM | 0.06 mM | 0.64 mM | 0.64 mM |
| Ca2+ | 1 mM | 1 mM | 1 mM | 1 mM | 1 mM | | 1 mM |
| EDTA | | | | | | 2 mM | |
| Water hardness equivalents | 5.6° dH | 5.6° dH | 5.6° dH | 5.6° dH | 5.6° dH | 0° dH | 5.6° dH |
| pH | 8.5 | 8.5 | 8.5 | 8.5 | 8.5 | 8.5 | 8.5 |
| Temp | RT | RT | RT | RT | RT | RT | RT |
| Buffer | 50 mM | 50 mM | 50 mM | 50 mM | 50 mM | 50 mM | 50 mM |
| Measuring time | 0-120 sec | 300 sec | 0-120 sec | 0-120 sec | 0-120 sec | 0-120 sec | 300 sec |

Procedure

1) Enzyme samples were diluted to 0.2 ppm with Lipase dilution solution.
2) Substrate working solution was prepared from pNP-palmitate or pNP-valerate stock solution and Surfactant solution
3) 20 μL diluted enzyme sample (from (1)) was transferred to 96 well microtiter plate 4) 180 μL Substrate working solution (from (2)) was added
5) Immediately after addition of Substrate working solution, the absorbance was measured at 405 nm every 20 seconds for up to 300 seconds at room temperature (25° C.), with 10 second shaking before first reading. The absorbance was measured on a SpectraMax M2 from Molecular Devices.

For blanks, diluted enzyme was replaced by 20 μL Lipase dilution solution.

Each sample was run in triplicates on each plate, which also includes 3 blanks, reference in triplicate in same concentration as enzyme sample, as well as a standard curve made from 0.1, 0.2, 0.4, and 0.6 ppm lipase (SEQ ID NO: 1—LIPOLASE™).

Activity was calculated as the slope of the plot of OD405 nm versus time and then corrected by subtracting blank. The activities are given relative to the activity of the reference.

| Relative lipase activity in composition comprising surfactant solution A compared to SEQ ID NO: 1<br>1.91 mM LAS (pNP-palmitate)<br>0.02 ppm lipase variant | | |
|---|---|---|
| Sample ID | Substitutions | Relative activity to SEQ ID NO: 1 |
| LP-1 | SEQ ID NO: 1 | 1.00 |
| LP-4 | E1C + H198T + N233C | 3.08 |
| LP-5 | E1C + H198G + N233C | 1.77 |
| LP-6 | E1C + L227F + N233C | 2.65 |
| LP-8 | E1C + E210T + N233C | 2.31 |
| LP-9 | E1C + E210N + N233C | 2.33 |
| LP-10 | E1C + V176M + N233C | 1.88 |
| LP-11 | E1C + K98T + N233C | 1.88 |
| LP-12 | E1C + K98E + N233C | 2.09 |
| LP-13 | E1C + E56S + N233C | 1.94 |
| LP-14 | E1C + E56Q + N233C | 2.50 |
| LP-15 | E1C + E56R + N233C | 2.38 |
| LP-16 | E1C + F51M + N233C | 2.63 |
| LP-17 | E1C + D27R + F51Y + N233C | 2.82 |
| LP-18 | E1C + V2I + N233C | 2.38 |
| LP-19 | E1C + V2N + N233C | 1.16 |
| LP-20 | E1C + V2K + N233C | 1.33 |
| LP-21 | E1C + V2A + N233C | 1.89 |
| LP-22 | E1C + D96L + N233C | 1.68 |
| LP-23 | E1C + L69R + N233C | 2.17 |
| LP-24 | E1C + V2Y + N233C | 1.16 |
| LP-25 | E1C + N233C + P256T | 2.11 |
| LP-26 | E1C + N233C + D254S | 2.41 |
| LP-28 | E1C + H198S + N233C | 2.18 |
| LP-29 | E1C + D111A + N233C | 2.06 |
| LP-30 | E1C + D96E + N233C | 2.15 |
| LP-31 | E1C + G38A + N233C | 3.39 |
| LP-32 | E1C + N33Q + N233C | 3.21 |
| LP-33 | E1C + N33K + N233C | 3.62 |
| LP-34 | E1C + V176L + N233C | 3.61 |
| LP-35 | E1C + E56K + N233C | 3.03 |
| LP-36 | E1C + E210A + N233C | 2.81 |

-continued

| Relative lipase activity in composition comprising surfactant solution A compared to SEQ ID NO: 1<br>1.91 mM LAS (pNP-palmitate)<br>0.02 ppm lipase variant | | |
|---|---|---|
| Sample ID | Substitutions | Relative activity to SEQ ID NO: 1 |
| LP-37 | E1C + E210Q + N233C | 2.93 |
| LP-38 | E1C + E210R + N233C | 2.99 |
| LP-40 | E1C + K98R + N233C | 2.97 |
| LP-41 | E1C + K98V + N233C | 3.17 |
| LP-42 | E1C + F51L + N233C | 3.45 |
| LP-43 | E1C + F51I + N233C | 3.16 |
| LP-44 | E1C + L227G + N233C | 3.82 |
| LP-45 | E1C + E210K + N233C | 2.70 |
| LP-46 | E1C + K98Q + N233C | 3.36 |
| LP-47 | E1C + Y220F + N233C | 2.75 |
| LP-49 | E1C + H198G + N233C | 2.68 |
| LP-50 | E1C + L69V + N233C | 3.10 |
| LP-51 | E1C + L69T + N233C | 3.09 |
| LP-52 | E1C + L69S + N233C | 3.20 |
| LP-53 | E1C + L69H + N233C | 3.24 |
| LP-54 | E1C + L69F + N233C | 3.57 |
| LP-55 | E1C + L69C + N233C | 2.83 |
| LP-56 | E1C + K237C | 4.59 |
| LP-58 | E1C + K98I + N233C | 3.46 |
| LP-61 | E1C + D27R + F51I + E56R + K98E + T231R + N233C | 1.11 |
| LP-62 | E1C + D27R + F51I + E56R + K98E + T231R + N233C + D254S | 1.69 |
| LP-63 | E1C + D27R + G38A + F51L + K98I + D111A + G163S + H198S + Y220F + T231R + N233C + P256T | 1.89 |
| LP-64 | E1C + D27R + G38A + F51L + D96E + K98I + D111A + G163K + H198S + Y220F + T231R + N233C + D254S + P256T | 2.16 |

| Relative lipase activity in composition comprising surfactant solution B compared to SEQ ID NO: 1<br>1.96 mM AEOS (pNP-valerate)<br>0.02 ppm lipase variant | | |
|---|---|---|
| Sample No | Substitutions | Relative activity to SEQ ID NO: 1 |
| LP-1 | SEQ ID NO: 1 | 1.00 |
| LP-3 | E1C + H198Y + N233C | 1.67 |
| LP-4 | E1C + H198T + N233C | 1.26 |
| LP-5 | E1C + H198G + N233C | 1.24 |
| LP-28 | E1C + H198S + N233C | 1.48 |

-continued

| Relative lipase activity in composition comprising surfactant solution B compared to SEQ ID NO: 1<br>1.96 mM AEOS (pNP-valerate)<br>0.02 ppm lipase variant | | |
|---|---|---|
| Sample No | Substitutions | Relative activity to SEQ ID NO: 1 |
| LP-48 | E1C + H198L + N233C | 1.97 |
| LP-49 | E1C + H198G + N233C | 1.40 |

| Relative lipase activity in composition comprising surfactant solution C compared to SEQ ID NO: 1<br>LAS:AEO 2:1, 2 mM Ca2+, 1.9 mM detergent (pNP-palmitate)<br>0.02 ppm lipase variant | | |
|---|---|---|
| Sample No | Substitutions | Relative activity to SEQ ID NO: 1 |
| LP-1 | SEQ ID NO: 1 | 1.00 |
| LP-3 | E1C + H198Y + N233C | 6.75 |
| LP-4 | E1C + H198T + N233C | 5.90 |
| LP-5 | E1C + H198G + N233C | 5.30 |
| LP-6 | E1C + L227F + N233C | 6.52 |
| LP-7 | E1C + L227R + N233C | 1.80 |
| LP-8 | E1C + E210T + N233C | 8.47 |
| LP-9 | E1C + E210N + N233C | 7.56 |
| LP-10 | E1C + V176M + N233C | 4.52 |
| LP-11 | E1C + K98T + N233C | 5.01 |
| LP-12 | E1C + K98E + N233C | 5.10 |
| LP-13 | E1C + E56S + N233C | 6.02 |
| LP-14 | E1C + E56Q + N233C | 6.36 |
| LP-15 | E1C + E56R + N233C | 5.90 |
| LP-16 | E1C + F51M + N233C | 6.46 |
| LP-17 | E1C + D27R + F51Y + N233C | 6.19 |
| LP-18 | E1C + V2I + N233C | 6.18 |
| LP-19 | E1C + V2N + N233C | 2.75 |
| LP-20 | E1C + V2K + N233C | 2.46 |
| LP-21 | E1C + V2A + N233C | 5.84 |

-continued

| Relative lipase activity in composition comprising surfactant solution C compared to SEQ ID NO: 1 LAS:AEO 2:1, 2 mM Ca2+, 1.9 mM detergent (pNP-palmitate) 0.02 ppm lipase variant | | |
|---|---|---|
| Sample No | Substitutions | Relative activity to SEQ ID NO: 1 |
| LP-22 | E1C + D96L + N233C | 6.73 |
| LP-23 | E1C + L69R + N233C | 5.81 |
| LP-24 | E1C + V2Y + N233C | 2.99 |
| LP-25 | E1C + N233C + P256T | 5.54 |
| LP-26 | E1C + N233C + D254S | 5.54 |
| LP-27 | E1C + T231R + N233C | 2.62 |
| LP-28 | E1C + H198S + N233C | 7.10 |
| LP-29 | E1C + D111A + N233C | 4.75 |
| LP-30 | E1C + D96E + N233C | 4.28 |
| LP-31 | E1C + G38A + N233C | 5.83 |
| LP-32 | E1C + N33Q + N233C | 5.90 |
| LP-33 | E1C + N33K + N233C | 5.96 |
| LP-34 | E1C + V176L + N233C | 6.48 |
| LP-35 | E1C + E56K + N233C | 5.65 |
| LP-36 | E1C + E210A + N233C | 7.84 |
| LP-37 | E1C + E210Q + N233C | 8.01 |
| LP-38 | E1C + E210R + N233C | 7.51 |
| LP-39 | E1C + H198D + N233C | 2.54 |
| LP-40 | E1C + K98R + N233C | 6.10 |
| LP-41 | E1C + K98V + N233C | 5.38 |
| LP-42 | E1C + F51L + N233C | 7.00 |
| LP-43 | E1C + F51I + N233C | 5.16 |
| LP-44 | E1C + L227G + N233C | 4.79 |
| LP-45 | E1C + E210K + N233C | 6.65 |
| LP-46 | E1C + K98Q + N233C | 6.02 |
| LP-47 | E1C + Y220F + N233C | 5.25 |
| LP-48 | E1C + H198L + N233C | 5.77 |
| LP-49 | E1C + H198G + N233C | 5.18 |
| LP-50 | E1C + L69V + N233C | 5.37 |
| LP-51 | E1C + L69T + N233C | 5.74 |
| LP-52 | E1C + L69S + N233C | 5.56 |
| LP-53 | E1C + L69H + N233C | 5.39 |
| LP-54 | E1C + L69F + N233C | 6.58 |
| LP-55 | E1C + L69C + N233C | 4.73 |
| LP-56 | E1C + K237C | 3.15 |
| LP-58 | E1C + K98I + N233C | 5.30 |
| LP-61 | E1C + D27R + F51I + E56R + K98E + T231R + N233C | 3.00 |
| LP-62 | E1C + D27R + F51I + E56R + K98E + T231R + N233C + D254S | 3.34 |
| LP-63 | E1C + D27R + G38A + F51L + K98I + D111A + G163S + H198S + Y220F + T231R + N233C + P256T | 4.37 |
| LP-64 | E1C + D27R + G38A + F51L + D96E + K98I + D111A + G163K + H198S + Y220F + T231R + N233C + D254S + P256T | 5.06 |
| LP-65 | E1C + D27R + G38R + F51L + D96E + K98I + D111A + G163K + H198S + Y220F + T231R + N233C + D254S + P256T | 4.79 |
| LP-66 | E1C + D27R + F51L + D96I + K98I + D111A + G163K + H198S + Y220F + T231R + N233C + P256T | 5.70 |
| LP-67 | E1C + D27R + F51L + D96E + K98I + D111A + G163S + H198S + Y220F + T231R + N233C + P256T | 4.98 |
| LP-68 | E1C + D27R + F51L + D96E + K98I + D111A + G163K + H198S + Y220F + T231R + N233C + P256T | 4.12 |
| LP-69 | E1C + D27R + G38A + F51I + D96E + K98I + D111A + G163K + H198S + Y220F + T231R + N233C + D254S + P256T | 4.98 |
| LP-70 | E1C + D27R + G38A + F51V + D96E + K98I + D111A + G163K + H198S + Y220F + T231R + N233C + P256T | 4.22 |
| LP-71 | E1C + D27R + F51V + D96E + K98I + D111A + G163K + H198S + Y220F + T231R + N233C + P256T | 3.81 |
| LP-72 | E1C + D27R + F51V + D96E + K98I + D111A + G163S + H198S + Y220F + T231R + N233C + D254S + P256T | 5.33 |
| LP-73 | E1C + D27R + F51V + D96I + K98I + D111A + G163K + H198S + Y220F + T231R + N233C + D254S + P256T | 4.68 |
| LP-74 | E1C + D27R + F51V + K98I + D111A + G163K + H198S + Y220F + T231R + N233C + D254S + P256T | 4.73 |
| LP-75 | E1C + D27R + F51V + D96E + K98I + D111A + G163K + H198S + Y220F + T231R + N233C + D254S + P256T | 5.43 |
| LP-76 | E1C + D27R + G38A + F51V + D96E + K98I + D111A + G163K + H198S + Y220F + T231R + N233C + D254S + P256T | 5.07 |
| LP-77 | E1C + F51V + D96E + K98I + D111A + G163S + H198S + Y220F + T231R + N233C + P256T | 3.99 |
| LP-79 | E1C + G38A + F51V + D96E + K98I + D111A + G163K + H198S + Y220F + T231R + N233C + P256T | 3.96 |
| LP-80 | E1C + F51V + D96E + K98I + D111A + G163K + H198S + Y220F + T231R + N233C + P256T | 4.33 |

-continued

Relative lipase activity in composition comprising surfactant solution C compared to SEQ ID NO: 1
LAS:AEO 2:1, 2 mM Ca2+, 1.9 mM detergent (pNP-palmitate)
0.02 ppm lipase variant

| Sample No | Substitutions | Relative activity to SEQ ID NO: 1 |
|---|---|---|
| LP-81 | E1C + F51V + D96I + K98I + D111A + G163K + H198S + Y220F + T231R + N233C + D254S + P256T | 6.32 |
| LP-82 | E1C + F51V + K98I + D111A + G163K + H198S + Y220F + T231R + N233C + D254S + P256T | 4.65 |
| LP-83 | E1C + F51I + D96E + K98I + D111A + G163K + H198S + Y220F + T231R + N233C + D254S + P256T | 5.16 |
| LP-84 | E1C + D27R + F51L + D96E + K98I + D111A + G163K + H198S + Y220F + T231R + N233C + D254S + P256T | 4.78 |
| LP-85 | E1C + D27R + N33K + G38A + F51V + D96E + K98I + D111A + G163K + H198S + Y220F + T231R + N233C | 4.39 |
| LP-86 | E1C + G38R + F51V + D96E + K98I + D111A + G163K + H198S + Y220F + T231R + N233C + D254S + P256T | 4.34 |
| LP-87 | E1C + F51V + D96E + K98I + D111A + G163K + H198S + Y220F + T231R + N233C + D254S + P256T | 5.70 |
| LP-88 | E1C + G38A + F51V + D96E + K98I + D111A + G163K + H198S + Y220F + T231R + N233C + D254S + P256T | 5.66 |
| LP-89 | E1C + D27R + G38R + F51V + D96E + K98I + D111A + G163K + H198S + Y220F + T231R + N233C + D254S + P256T | 5.25 |

Relative lipase + activity in composition comprising surfactant solution D compared to SEQ + ID NO: 1
LAS:AEO 2:1, 2 mM Ca2+, 0.49 mM detergent (pNP-palmitate)
0.02 ppm lipase variant

| Sample No | Substitutions | Relative activity to SEQ ID NO: 1 |
|---|---|---|
| LP-1 | SEQ + ID + NO: +1 | 1.00 |
| LP-3 | E1C + H198Y + N233C | 5.17 |
| LP-4 | E1C + H198T + N233C | 1.71 |
| LP-5 | E1C + H198G + N233C | 1.97 |
| LP-6 | E1C + L227F + N233C | 3.75 |
| LP-8 | E1C + E210T + N233C | 9.96 |
| LP-9 | E1C + E210N + N233C | 8.37 |
| LP-10 | E1C + V176M + N233C | 2.59 |
| LP-11 | E1C + K98T + N233C | 2.99 |
| LP-12 | E1C + K98E + N233C | 3.13 |
| LP-13 | E1C + E56S + N233C | 3.20 |
| LP-14 | E1C + E56Q + N233C | 2.89 |
| LP-15 | E1C + E56R + N233C | 3.92 |
| LP-16 | E1C + F51M + N233C | 3.38 |
| LP-17 | E1C + D27R + F51Y + N233C | 4.63 |
| LP-18 | E1C + V2I + N233C | 3.59 |
| LP-19 | E1C + V2N + N233C | 2.46 |
| LP-20 | E1C + V2K + N233C | 2.80 |
| LP-21 | E1C + V2A + N233C | 3.56 |
| LP-22 | E1C + D96L + N233C | 3.48 |
| LP-23 | E1C + L69R + N233C | 2.66 |
| LP-24 | E1C + V2Y + N233C | 2.47 |
| LP-25 | E1C + N233C + P256T | 3.25 |
| LP-26 | E1C + N233C + D254S | 3.76 |
| LP-27 | E1C + T231R + N233C | 5.84 |
| LP-28 | E1C + H198S + N233C | 2.70 |
| LP-29 | E1C + D111A + N233C | 1.91 |
| LP-30 | E1C + D96E + N233C | 1.68 |
| LP-31 | E1C + G38A + N233C | 2.30 |
| LP-32 | E1C + N33Q + N233C | 2.71 |
| LP-33 | E1C + N33K + N233C | 2.38 |
| LP-34 | E1C + V176L + N233C | 2.79 |
| LP-35 | E1C + E56K + N233C | 2.31 |
| LP-36 | E1C + E210A + N233C | 9.68 |
| LP-37 | E1C + E210Q + N233C | 7.17 |
| LP-38 | E1C + E210R + N233C | 7.78 |
| LP-40 | E1C + K98R + N233C | 2.94 |
| LP-41 | E1C + K98V + N233C | 2.18 |
| LP-42 | E1C + F51L + N233C | 2.30 |
| LP-43 | E1C + F51I + N233C | 2.50 |
| LP-44 | E1C + L227G + N233C | 1.33 |
| LP-45 | E1C + E210K + N233C | 6.71 |
| LP-46 | E1C + K98Q + N233C | 2.93 |

-continued

Relative lipase + activity in composition comprising surfactant solution D compared to SEQ + ID NO: 1
LAS:AEO 2:1, 2 mM Ca2+, 0.49 mM detergent (pNP-palmitate)
0.02 ppm lipase variant

| Sample No | Substitutions | Relative activity to SEQ ID NO: 1 |
|---|---|---|
| LP-47 | E1C + Y220F + N233C | 2.74 |
| LP-48 | E1C + H198L + N233C | 2.58 |
| LP-49 | E1C + H198G + N233C | 1.41 |
| LP-50 | E1C + L69V + N233C | 2.07 |
| LP-51 | E1C + L69T + N233C | 2.50 |
| LP-52 | E1C + L69S + N233C | 2.33 |
| LP-53 | E1C + L69H + N233C | 2.45 |
| LP-54 | E1C + L69F + N233C | 3.04 |
| LP-55 | E1C + L69C + N233C | 2.27 |
| LP-56 | E1C + K237C | 1.49 |
| LP-58 | E1C + K98I + N233C | 2.16 |
| LP-61 | E1C + D27R + F51I + E56R + K98E + T231R + N233C | 6.57 |
| LP-62 | E1C + D27R + F51I + E56R + K98E + T231R + N233C + D254S | 11.24 |
| LP-63 | E1C + D27R + G38A + F51L + K98I + D111A + G163S + H198S + Y220F + T231R + N233C + P256T | 2.83 |
| LP-64 | E1C + D27R + G38A + F51L + D96E + K98I + D111A + G163K + H198S + Y220F + T231R + N233C + D254S + P256T | 3.33 |
| LP-65 | E1C + D27R + G38R + F51L + D96E + K98I + D111A + G163K + H198S + Y220F + T231R + N233C + D254S + P256T | 3.51 |
| LP-66 | E1C + D27R + F51L + D96I + K98I + D111A + G163K + H198S + Y220F + T231R + N233C + P256T | 9.11 |
| LP-67 | E1C + D27R + F51L + D96E + K98I + D111A + G163S + H198S + Y220F + T231R + N233C + P256T | 5.19 |
| LP-68 | E1C + D27R + F51L + D96E + K98I + D111A + G163K + H198S + Y220F + T231R + N233C + P256T | 4.86 |
| LP-69 | E1C + D27R + G38A + F51I + D96E + K98I + D111A + G163K + H198S + Y220F + T231R + N233C + D254S + P256T | 4.22 |
| LP-70 | E1C + D27R + G38A + F51V + D96E + K98I + D111A + G163K + H198S + Y220F + T231R + N233C + P256T | 3.72 |
| LP-71 | E1C + D27R + F51V + D96E + K98I + D111A + G163K + H198S + Y220F + T231R + N233C + P256T | 4.51 |
| LP-72 | E1C + D27R + F51V + D96E + K98I + D111A + G163S + H198S + Y220F + T231R + N233C + D254S + P256T | 4.67 |
| LP-73 | E1C + D27R + F51V + D96I + K98I + D111A + G163K + H198S + Y220F + T231R + N233C + D254S + P256T | 5.65 |
| LP-74 | E1C + D27R + F51V + K98I + D111A + G163K + H198S + Y220F + T231R + N233C + D254S + P256T | 4.26 |
| LP-75 | E1C + D27R + F51V + D96E + K98I + D111A + G163K + H198S + Y220F + T231R + N233C + D254S + P256T | 4.40 |
| LP-76 | E1C + D27R + G38A + F51V + D96E + K98I + D111A + G163K + H198S + Y220F + T231R + N233C + D254S + P256T | 3.93 |
| LP-77 | E1C + F51V + D96E + K98I + D111A + G163S + H198S + Y220F + T231R + N233C + P256T | 2.97 |
| LP-79 | E1C + G38A + F51V + D96E + K98I + D111A + G163K + H198S + Y220F + T231R + N233C + P256T | 2.26 |
| LP-80 | E1C + F51V + D96E + K98I + D111A + G163K + H198S + Y220F + T231R + N233C + P256T | 2.93 |
| LP-81 | E1C + F51V + D96I + K98I + D111A + G163K + H198S + Y220F + T231R + N233C + D254S + P256T | 5.14 |
| LP-82 | E1C + F51V + K98I + D111A + G163K + H198S + Y220F + T231R + N233C + D254S + P256T | 3.63 |
| LP-83 | E1C + F51I + D96E + K98I + D111A + G163K + H198S + Y220F + T231R + N233C + D254S + P256T | 3.94 |
| LP-84 | E1C + D27R + F51L + D96E + K98I + D111A + G163K + H198S + Y220F + T231R + N233C + D254S + P256T | 3.83 |
| LP-85 | E1C + D27R + N33K + G38A + F51V + D96E + K98I + D111A + G163K + H198S + Y220F + T231R + N233C | 2.80 |
| LP-86 | E1C + G38R + F51V + D96E + K98I + D111A + G163K + H198S + Y220F + T231R + N233C + D254S + P256T | 3.31 |
| LP-87 | E1C + F51V + D96E + K98I + D111A + G163K + H198S + Y220F + T231R + N233C + D254S + P256T | 3.57 |
| LP-88 | E1C + G38A + F51V + D96E + K98I + D111A + G163K + H198S + Y220F + T231R + N233C + D254S + P256T | 3.08 |
| LP-89 | E1C + D27R + G38R + F51V + D96E + K98I + D111A + G163K + H198S + Y220F + T231R + N233C + D254S + P256T | 3.45 |

Relative activity in composition comprising surfactant solution E compared to SEQ ID NO: 1
LAS:AEO 2:1, 2 mM Ca2+, 0.19 mM detergent (pNP-palmitate)
0.02 ppm lipase variant

| Sample No | Substitutions | Relative activity to SEQ ID NO: 1 |
|---|---|---|
| LP-1 | SEQ ID NO: 1 | 1.00 |
| LP-3 | E1C + H198Y + N233C | 1.28 |
| LP-6 | E1C + L227F + N233C | 2.74 |
| LP-8 | E1C + E210T + N233C | 18.73 |
| LP-9 | E1C + E210N + N233C | 14.28 |
| LP-10 | E1C + V176M + N233C | 1.49 |
| LP-11 | E1C + K98T + N233C | 1.20 |
| LP-12 | E1C + K98E + N233C | 1.69 |
| LP-13 | E1C + E56S + N233C | 1.59 |
| LP-14 | E1C + E56Q + N233C | 2.13 |
| LP-15 | E1C + E56R + N233C | 2.74 |
| LP-16 | E1C + F51M + N233C | 2.12 |
| LP-17 | E1C + D27R + F51Y + N233C | 3.26 |
| LP-18 | E1C + V2I + N233C | 2.62 |
| LP-19 | E1C + V2N + N233C | 1.66 |
| LP-20 | E1C + V2K + N233C | 2.44 |
| LP-21 | E1C + V2A + N233C | 2.34 |
| LP-22 | E1C + D96L + N233C | 3.97 |
| LP-23 | E1C + L69R + N233C | 2.17 |
| LP-24 | E1C + V2Y + N233C | 1.87 |
| LP-25 | E1C + N233C + P256T | 2.15 |
| LP-26 | E1C + N233C + D254S | 5.97 |
| LP-27 | E1C + T231R + N233C | 10.45 |
| LP-29 | E1C + D111A + N233C | 1.34 |
| LP-31 | E1C + G38A + N233C | 1.88 |
| LP-32 | E1C + N33Q + N233C | 2.46 |
| LP-33 | E1C + N33K + N233C | 2.20 |
| LP-34 | E1C + V176L + N233C | 2.61 |
| LP-35 | E1C + E56K + N233C | 2.61 |
| LP-36 | E1C + E210A + N233C | 25.77 |
| LP-37 | E1C + E210Q + N233C | 16.45 |
| LP-38 | E1C + E210R + N233C | 20.99 |
| LP-40 | E1C + K98R + N233C | 2.25 |
| LP-41 | E1C + K98V + N233C | 1.73 |
| LP-42 | E1C + F51L + N233C | 1.29 |
| LP-43 | E1C + F51I + N233C | 1.63 |
| LP-45 | E1C + E210K + N233C | 18.03 |
| LP-46 | E1C + K98Q + N233C | 2.25 |
| LP-47 | E1C + Y220F + N233C | 2.51 |
| LP-48 | E1C + H198L + N233C | 1.85 |
| LP-50 | E1C + L69V + N233C | 2.17 |
| LP-51 | E1C + L69T + N233C | 2.12 |
| LP-52 | E1C + L69S + N233C | 2.29 |
| LP-53 | E1C + L69H + N233C | 2.42 |
| LP-54 | E1C + L69F + N233C | 2.85 |
| LP-55 | E1C + L69C + N233C | 2.06 |
| LP-56 | E1C + K237C | 1.71 |
| LP-58 | E1C + K98I + N233C | 1.68 |
| LP-61 | E1C + D27R + F51I + E56R + K98E + T231R + N233C | 25.40 |
| LP-62 | E1C + D27R + F51I + E56R + K98E + T231R + N233C + D254S | 25.76 |
| LP-63 | E1C + D27R + G38A + F51L + K98I + D111A + G163S + H198S + Y220F + T231R + N233C + P256T | 2.95 |
| LP-64 | E1C + D27R + G38A + F51L + D96E + K98I + D111A + G163K + H198S + Y220F + T231R + N233C + D254S + P256T | 5.55 |
| LP-65 | E1C + D27R + G38R + F51L + D96E + K98I + D111A + G163K + H198S + Y220F + T231R + N233C + D254S + P256T | 7.93 |
| LP-66 | E1C + D27R + F51L + D96I + K98I + D111A + G163K + H198S + Y220F + T231R + N233C + P256T | 22.39 |
| LP-67 | E1C + D27R + F51L + D96E + K98I + D111A + G163S + H198S + Y220F + T231R + N233C + P256T | 8.12 |
| LP-68 | E1C + D27R + F51L + D96E + K98I + D111A + G163K + H198S + Y220F + T231R + N233C + P256T | 6.23 |
| LP-69 | E1C + D27R + G38A + F51I + D96E + K98I + D111A + G163K + H198S + Y220F + T231R + N233C + D254S + P256T | 10.04 |
| LP-70 | E1C + D27R + G38A + F51V + D96E + K98I + D111A + G163K + H198S + Y220F + T231R + N233C + P256T | 3.71 |
| LP-71 | E1C + D27R + F51V + D96E + K98I + D111A + G163K + H198S + Y220F + T231R + N233C + P256T | 4.97 |
| LP-72 | E1C + D27R + F51V + D96E + K98I + D111A + G163S + H198S + Y220F + T231R + N233C + D254S + P256T | 10.36 |
| LP-73 | E1C + D27R + F51V + D96I + K98I + D111A + G163K + H198S + Y220F + T231R + N233C + D254S + P256T | 14.61 |
| LP-74 | E1C + D27R + F51V + K98I + D111A + G163K + H198S + Y220F + T231R + N233C + D254S + P256T | 10.71 |

-continued

| Relative activity in composition comprising surfactant solution E compared to SEQ ID NO: 1 LAS:AEO 2:1, 2 mM Ca2+, 0.19 mM detergent (pNP-palmitate) 0.02 ppm lipase variant | | |
|---|---|---|
| Sample No | Substitutions | Relative activity to SEQ ID NO: 1 |
| LP-75 | E1C + D27R + F51V + D96E + K98I + D111A + G163K + H198S + Y220F + T231R + N233C + D254S + P256T | 12.15 |
| LP-76 | E1C + D27R + G38A + F51V + D96E + K98I + D111A + G163K + H198S + Y220F + T231R + N233C + D254S + P256T | 9.77 |
| LP-77 | E1C + F51V + D96E + K98I + D111A + G163S + H198S + Y220F + T231R + N233C + P256T | 2.32 |
| LP-79 | E1C + G38A + F51V + D96E + K98I + D111A + G163K + H198S + Y220F + T231R + N233C + P256T | 1.32 |
| LP-80 | E1C + F51V + D96E + K98I + D111A + G163K + H198S + Y220F + T231R + N233C + P256T | 2.59 |
| LP-81 | E1C + F51V + D96I + K98I + D111A + G163K + H198S + Y220F + T231R + N233C + D254S + P256T | 20.02 |
| LP-82 | E1C + F51V + K98I + D111A + G163K + H198S + Y220F + T231R + N233C + D254S + P256T | 7.79 |
| LP-83 | E1C + F51I + D96E + K98I + D111A + G163K + H198S + Y220F + T231R + N233C + D254S + P256T | 9.43 |
| LP-84 | E1C + D27R + F51L + D96E + K98I + D111A + G163K + H198S + Y220F + T231R + N233C + D254S + P256T | 10.26 |
| LP-85 | E1C + D27R + N33K + G38A + F51V + D96E + K98I + D111A + G163K + H198S + Y220F + T231R + N233C | 2.51 |
| LP-86 | E1C + G38R + F51V + D96E + K98I + D111A + G163K + H198S + Y220F + T231R + N233C + D254S + P256T | 7.57 |
| LP-87 | E1C + F51V + D96E + K98I + D111A + G163K + H198S + Y220F + T231R + N233C + D254S + P256T | 6.53 |
| LP-88 | E1C + G38A + F51V + D96E + K98I + D111A + G163K + H198S + Y220F + T231R + N233C + D254S + P256T | 5.26 |
| LP-89 | E1C + D27R + G38R + F51V + D96E + K98I + D111A + G163K + H198S + Y220F + T231R + N233C + D254S + P256T | 6.84 |

| Relative activity in composition comprising surfactant solution F compared to SEQ ID NO: 1 LAS:AEO 2:1 EDTA 1.9 mM detergent (pNP-palmitate) 0.02 ppm Lipase variant | | |
|---|---|---|
| Sample No | Substitutions | Relative activity to SEQ ID NO: 1 |
| LP-1 | SEQ ID NO: 1 | 1.00 |
| LP-8 | E1C + E210T + N233C | 2.98 |
| LP-9 | E1C + E210N + N233C | 2.32 |
| LP-15 | E1C + E56R + N233C | 2.09 |
| LP-22 | E1C + D96L + N233C | 1.45 |
| LP-26 | E1C + N233C + D254S | 1.64 |
| LP-35 | E1C + E56K + N233C | 1.30 |
| LP-36 | E1C + E210A + N233C | 2.20 |
| LP-37 | E1C + E210Q + N233C | 1.77 |
| LP-38 | E1C + E210R + N233C | 2.26 |
| LP-45 | E1C + E210K + N233C | 2.13 |
| LP-61 | E1C + D27R + F51I + E56R + K98E + T231R + N233C | 2.45 |
| LP-62 | E1C + D27R + F51I + E56R + K98E + T231R + N233C + D254S | 2.29 |
| LP-64 | E1C + D27R + G38A + F51L + D96E + K98I + D111A + G163K + H198S + Y220F + T231R + N233C + D254S + P256T | 2.10 |
| LP-65 | E1C + D27R + G38R + F51L + D96E + K98I + D111A + G163K + H198S + Y220F + T231R + N233C + D254S + P256T | 4.21 |
| LP-66 | E1C + D27R + F51L + D96I + K98I + D111A + G163K + H198S + Y220F + T231R + N233C + P256T | 2.71 |
| LP-69 | E1C + D27R + G38A + F51I + D96E + K98I + D111A + G163K + H198S + Y220F + T231R + N233C + D254S + P256T | 3.86 |
| LP-72 | E1C + D27R + F51V + D96E + K98I + D111A + G163S + H198S + Y220F + T231R + N233C + D254S + P256T | 4.32 |
| LP-73 | E1C + D27R + F51V + D96I + K98I + D111A + G163K + H198S + Y220F + T231R + N233C + D254S + P256T | 4.54 |
| LP-74 | E1C + D27R + F51V + K98I + D111A + G163K + H198S + Y220F + T231R + N233C + D254S + P256T | 3.19 |
| LP-75 | E1C + D27R + F51V + D96E + K98I + D111A + G163K + H198S + Y220F + T231R + N233C + D254S + P256T | 4.45 |
| LP-76 | E1C + D27R + G38A + F51V + D96E + K98I + D111A + G163K + H198S + Y220F + T231R + N233C + D254S + P256T | 4.14 |
| LP-81 | E1C + F51V + D96I + K98I + D111A + G163K + H198S + Y220F + T231R + N233C + D254S + P256T | 7.01 |

-continued

| Relative activity in composition comprising surfactant solution F compared to SEQ ID NO: 1 LAS:AEO 2:1 EDTA 1.9 mM detergent (pNP-palmitate) 0.02 ppm Lipase variant | | |
|---|---|---|
| Sample No | Substitutions | Relative activity to SEQ ID NO: 1 |
| LP-82 | E1C + F51V + K98I + D111A + G163K + H198S + Y220F + T231R + N233C + D254S + P256T | 2.72 |
| LP-83 | E1C + F51I + D96E + K98I + D111A + G163K + H198S + Y220F + T231R + N233C + D254S + P256T | 4.07 |
| LP-84 | E1C + D27R + F51L + D96E + K98I + D111A + G163K + H198S + Y220F + T231R + N233C + D254S + P256T | 4.00 |
| LP-86 | E1C + G38R + F51V + D96E + K98I + D111A + G163K + H198S + Y220F + T231R + N233C + D254S + P256T | 3.90 |
| LP-87 | E1C + F51V + D96E + K98I + D111A + G163K + H198S + Y220F + T231R + N233C + D254S + P256T | 3.44 |
| LP-88 | E1C + G38A + F51V + D96E + K98I + D111A + G163K + H198S + Y220F + T231R + N233C + D254S + P256T | 3.41 |
| LP-89 | E1C + D27R + G38R + F51V + D96E + K98I + D111A + G163K + H198S + Y220F + T231R + N233C + D254S + P256T | 3.54 |

| Relative activity in composition comprising surfactant solution G compared to SEQ ID NO: 1 LAS:AEO 2:1 1.9 mM detergent (pNP-valerate) 0.02 ppm Lipase variant | | |
|---|---|---|
| Sample No | Substitutions | Relative activity to SEQ ID NO: 1 |
| LP-1 | SEQ ID NO: 1 | 1.00 |
| LP-3 | E1C + H198Y + N233C | 1.71 |
| LP-4 | E1C + H198T + N233C | 1.33 |
| LP-5 | E1C + H198G + N233C | 1.25 |
| LP-28 | E1C + H198S + N233C | 1.52 |

-continued

| Relative activity in composition comprising surfactant solution G compared to SEQ ID NO: 1 LAS:AEO 2:1 1.9 mM detergent (pNP-valerate) 0.02 ppm Lipase variant | | |
|---|---|---|
| Sample No | Substitutions | Relative activity to SEQ ID NO: 1 |
| LP-48 | E1C + H198L + N233C | 1.93 |
| LP-49 | E1C + H198G + N233C | 1.26 |

The invention claimed is:

1. A lipase variant of a parent lipase, which (a) comprises a substitution at each position corresponding to positions 1, 231, and 233 of SEQ ID NO: 1;

(b) has a sequence identity of at least 85% but less than 100% sequence identity to SEQ ID NO: 1; and (c) has lipase activity.

2. The lipase variant of claim 1, comprising E1C.

3. The lipase variant of claim 1, comprising T231R.

4. The lipase variant of claim 1, comprising N233C or N233R.

5. The lipase variant of claim 1, comprising E1C+T231R+N233C.

6. The lipase variant of claim 1, further comprising a modification in at least one of the following positions: G38, D96, D111, G163, D254, and P256 of SEQ ID NO: 1.

7. The lipase variant of claim 1, further comprising a modification in at least one of the following positions: V2, D27, N33, G38, F51, E56, L69, D96, K98, D111, G163, V176, H198, E210, Y220, L227, K237, D254, and P256 of SEQ ID NO: 1.

8. The lipase variant of claim 1, which has a sequence identity of at least 90% sequence identity to SEQ ID NO: 1.

9. The lipase variant of claim 1, which has a sequence identity of at least 95% sequence identity to SEQ ID NO: 1.

10. A composition comprising a lipase variant of claim 1 and a surfactant.

11. The composition of claim 10, further comprising at least one additional enzyme selected from the group consisting of amylase, cellulase, beta-glucanase, mannanase, and protease.

12. A method of laundering, comprising laundering a fabric with a composition according to claim 1 at a temperature of 50° C. or less.

13. A method of pre-treating a fabric with a composition according to claim 1, comprising the steps of adding said composition to said fabric, and leaving the composition on the fabric for a period of time, and rinsing off said composition from said fabric.

* * * * *